US006440681B1

(12) United States Patent
Elliott et al.

(10) Patent No.: US 6,440,681 B1
(45) Date of Patent: *Aug. 27, 2002

(54) METHODS FOR IDENTIFYING AGONISTS AND ANTAGONISTS FOR HUMAN NEURONAL NICOTINIC ACETYLCHOLINE RECEPTORS

(75) Inventors: Kathryn J. Elliott; Steven B. Ellis, both of San Diego; Michael M. Harpold, El Cajon, all of CA (US)

(73) Assignee: Merck & Co., Inc., Rahway, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 08/487,596

(22) Filed: Jun. 7, 1995

Related U.S. Application Data

(63) Continuation-in-part of application No. 08/149,503, filed on Nov. 8, 1993, now abandoned, and a continuation-in-part of application No. 08/028,031, filed on Mar. 8, 1993, now abandoned, and a continuation-in-part of application No. 07/938,154, filed on Nov. 30, 1992, now Pat. No. 5,981,193, which is a continuation-in-part of application No. 07/504,455, filed on Apr. 3, 1990, now Pat. No. 5,369,028.

(51) Int. Cl.$^7$ .............................................. C12N 15/00
(52) U.S. Cl. .................... 435/7.2; 435/69.1; 435/252.3; 435/320.1; 435/325; 435/70.1; 435/71.1; 536/23.5
(58) Field of Search ............................. 435/69.1, 70.1, 435/240.2, 252.3, 320.1, 71.1, 7.2; 536/23.5; 935/70

(56) References Cited

U.S. PATENT DOCUMENTS

| | | | |
|---|---|---|---|
| 4,837,148 A | 6/1989 | Cregg | 435/172 |
| 4,855,231 A | 8/1989 | Stroman et al. | 435/68 |
| 4,859,609 A | 8/1989 | Dull et al. | 436/501 |
| 4,882,279 A | 11/1989 | Cregg | 435/68 |
| 4,929,555 A | 5/1990 | Cregg et al. | 435/172 |
| 4,981,784 A | 1/1991 | Evans et al. | 435/6 |
| 5,024,939 A | 6/1991 | Gorman | 435/69 |
| 5,071,773 A | 12/1991 | Evans et al. | 436/501 |
| 5,091,518 A | 2/1992 | Sucov et al. | 536/27 |
| 5,369,028 A | 11/1994 | Harpold et al. | 435/252 |
| 5,371,188 A | * 12/1994 | Heinemann | 530/350 |
| 5,386,025 A | 1/1995 | Jay et al. | 536/24 |
| 5,401,629 A | 3/1995 | Harpold et al. | 435/6 |
| 5,436,128 A | 7/1995 | Harpold et al. | 436/6 |
| 5,449,606 A | * 9/1995 | Heinemann | 435/6 |
| 5,591,590 A | * 1/1997 | Heinemann et al. | 435/7.1 |
| 5,981,193 A | * 11/1999 | Harpold | 435/7.1 |

FOREIGN PATENT DOCUMENTS

| | | |
|---|---|---|
| EP | 0325849 | 8/1989 |
| WO | 8803168 | 5/1988 |
| WO | 8909834 | 10/1989 |
| WO | 9010648 | 9/1990 |
| WO | 9106677 | 5/1991 |
| WO | 9115602 | 10/1991 |
| WO | 9202639 | 2/1992 |
| WO | 9513299 | 5/1995 |

OTHER PUBLICATIONS

Sambrook et al, Molecular Cloning, 2nd ed, p. 16.3, 1989.*
Nash et al, Soc.Neurosc. Abstr. 16:9.10, 1990.*
Nash et al, FASEB 4(7) 2665, 1990.*
George et al., Chapter 12: Current methods in Sequence Comparison and Analysis in *Macromolecular Sequencing and Synthesis, Selected Methods and Applications,* Alan R. Liss, Inc., pp. 127–149 (1988).
Koyama et al., Isolation of 115 human chromosome 8–specific expressed–sequence tags by exon amplification, *Genomics* 26:245–253 (1995).
Grenningloh et al., Alpha subunit variants of the human glycine receptor: primary structures, functional expression and chromosomal localization of the corresponding genes, *EMBO J.* 9(3): 771–776 (1990).
Lamar et al., Amplification of genomic sequences identifies a new gene, alpha 6, in the niocotinic acetylcholine receptor gene family, *Abstracts 20th Annual Meeting For Society For Neuroscience 16:* 681 #285.2 (1990).
Lin et al., Differential fluorescent staining of human chromosomes with daunomycin and adriamycin—the D–bands, *Science* 190: 61–63 (1975).
EMBL Databank, Accession No. X68275 (Sep. 22, 1992), P. Tarroni.
PIR 38 Databank, Accession No. S27274 (Tarroni et al.).
GeneSeq 12 Databank, Accession No. 006086 (WO 90/10648).
Whiting, P.J. and Lindstrom, J.M., "Characterization of Bovine and Human Neuronal Nicotinic Acetylcholine Receptors Using Monoclonal Antibodies", *J. Neurosci.,* 8(9):3395–3404, (1988).
Akong et al., Characterization of nicotinic acetylcholine receptors in a human neuroblastoma cell line, *FASEB J.* 4(3):A737 (1990).
Alam et al.,Reporter genes: Application to the study of mammalian gene transcription, *Anal. Biochem.* 188:245–254 (1990).
Albuquerque et al., Neuronal nicotinic receptors: Function, modulation and structure, *Seminars in the Neurosciences* 7:91–101 (1995).

(List continued on next page.)

*Primary Examiner*—Lorraine Spector
*Assistant Examiner*—Eliane Lazar-Wesley
(74) *Attorney, Agent, or Firm*—Vineet Kohli; Joanne M. Giesser

(57) ABSTRACT

Methods for identifying compounds which modulate the activity of human neuronal nicotinic acetylcholine receptors are provided. Invention methods employ DNAs encoding alpha and beta subunits of human neuronal nicotinic acetylcholine receptors, and the polypeptides encoded thereby. Test cells useful for conducting invention assays include mammalian and amphibian cells containing said DNA. Various combinations of subunits (i.e., one or more $\alpha_2$, $\alpha_3$, $\alpha_4$, $\alpha_5$, $\alpha_6$ and $\alpha_7$ subunits in combination with $\beta_2$, $\beta_3$ and/or $\beta_4$ subunits) can be employed for the invention assays.

168 Claims, 1 Drawing Sheet

OTHER PUBLICATIONS

Allard, et al., Sequence of the gene encoding the human M1 muscarinic acetylcholine receptor, *Nucl. Acids Res.* 15:10604 (1987).

Alton and Vapnek, Nucleotide sequence analysis of the chloramphenicol resistance transposon Tn9, *Nature* 282:864–869 (1979).

Anand et al., Nucleotide sequence of the human nicotinic acetylcholine receptor $\beta_2$ subunit gene, *Nucleic Acids Res.* 18(14):4272 (1990).

Anand et al., Neuronal nicotinic acetylcholine receptors expressed in Xenopus oocytes have a pentameric quaternary structure, *J. Biol. Chem.* 266(17):11192–11198 (1991).

Baldwin et al., Cloning of the luciferase structural genes from *Vibrio harveyi* and expression of bioluminescence in *Escherichia coli*, *Biochemistry* 23:3663–3667 (1984).

Ballivet et al., Electrophysiology of a chick neuronal nicotinic acetylcholine receptor expressed in Xenopus oocytes after cDNA injection, *Neuron* 1:847–852 (1988).

Beeson et al., The human muscle nicotinic acetylcholine receptor α–subunit exists as two isoforms: a novel exon, *EMBO J.* 9(7):2101–2106 (1990).

Bertrand et al., Unconventional pharmacology of a neuronal nicotinic receptor mutated in the channel domain, *Proc. Natl. Acad. Sci. USA* 89:1261–1265 (1992).

Bertrand and Changeux, Nicotinic receptor: An allosteric protein specialized for intercellular communication, *Seminars in the Neurosciences* 7:75–90 (1995).

BIOSIS abstract #87125524, Bartel et al., Growth factors and membrane depolarization activate distinct programs of early response gene expression dissociation of fos and jun induction, *Genes Dev.* 3(3):304–313 (1989).

BIOSIS abstract #88119253, Levy et al., Cytoplasmic activation of ISGF3 the positive regulator of interferon–alpha–stimulated transcription reconstituted in vitro, *Genes Dev.* 3(9):1362–1371 (1989).

BIOSIS abstract #88127139, Nishizuka et al., The family of protein kinase C for signal transduction, *J. Am. Med. Assoc.* 262(13):1826–1833 (1989).

Blackshear et al., Protein kinase C–dependent and –independent pathways of proto–oncogene induction in human astrocytoma cells, *J. Biol. Chem.* 262(16):7774–7781 (1987).

Blanchard et al.,The regulatory stategies of c–myc and c–fos proto–oncogenes share some common mechanisms, *Biochimie* 70:877–884 (1988).

Bonner et al., Cloning and expression of the human and rat m5 muscarinic acetylcholine receptor genes, *Neuron* 1:403–410 (1988).

Bonnieu et al., Requirements for c–fos mRNA down regulation in growth stimulated murine cells, *Oncogene* 4:881–888 (1989).

Bouche, Basic fibroblast growth factor enters the nucleolus and stimulates the transcription of ribosomal genes in ABAE cells undergoing $G_0$–$G_1$ transition, *Proc. Natl. Acad. Sci. USA* 84:6770–6774 (1987).

Boulter et al., Isolation of a cDNA clone coding for a possible neural nicotinic acetylcholine receptor α–subunit, *Nature* 319:368–374 (1986).

Boulter et al., Functional expression of two neuronal nicotinic acetylcholine receptors from cDNA clones identifies a gene family, *Proc. Natl. Acad. Sci. USA* 84:7763–7767 (1987).

Boulter et al., α3, α5, and β4: Three members of the rat neuronal nicotinic acetylcholine receptor–related gene family form a gene cluster, *J. Biol. Chem.* 265:4472–4482 (1990).

Boulter et al., Rat nicotinic acetylcholine receptor alpha 6 mRNA sequence, unpublished (1993) GENBANK Accession #L08227.

Briggs et al., Human α7 nicotinic acetylcholine receptor responses to novel ligands, *Neuropharmacology* 34:583–590 (1995).

Bunzow et al., Cloning and expression of a rat $D_2$ dopamine receptor cDNA, *Nature* 336:783–787 (1988).

Changelian et al., Structure of the NGFI–A gene and detection of upstream sequences responsible for its transcriptional induction by nerve growth factor, *Proc. Natl. Acad. Sci. USA* 86:377–381 (1989).

Chavez–Noriega et al., Characterization of recombinant human neuronal nicotinic ACH receptors expressed in HEK293 cells and Xenopus oocytes, *Soc. Neurosci. Abstr.* (1995).

Chini et al., Neuronal–type α–bungarotoxin receptors and the $\alpha_5$–nicotinic receptor subunit gene are expressed in neuronal and nonneuronal human cell lines, *Proc. Natl. Acad. Sci. USA* 89:1572–1576 (1992).

Chini et al., Molecular cloning and chromosomal localization of the human $\alpha_7$–nicotinic receptor subunit gene (CHRNA7), *Genomics* 19:379–381 (1994).

Choi et al., Labeling studies of photolabile philanthotoxins with nicotinic acetylcholine receptors: Mode of interaction between toxin and receptor, *Chemistry & Biology* 2:23–32 (1995).

Clarke, The fall and rise of neuronal α–bungarotoxin binding proteins, *Trends Pharmacol. Sci.* 13:407–413 (1992).

Claudio et al., Genetic reconstitution of functional acetylcholine receptor channels in mouse fibroblasts, *Science* 238:1688–1694 (1987).

Clementi et al., Pharmacological characterization of cholinergic receptors in a human neuroblastoma cell line, *J. Neurochem.* 47(1):291–297 (1986).

Cleveland et al., Number and evolutionary conservation of the α– and β–tubulin and cytoplasmic β– and γ–actin genes using specific cloned cDNA probes, *Cell* 20:95–105 (1980).

Cohen et al., Regions of β2 and β4 responsible for differences between the steady state dose–response relationships of the α3β2 and α3β4 neuronal nicotinic receptors, *J. Gen. Physiol.* 105:745–764 (1995).

Collins et al., cAMP stimulates transcription of the $\beta_2$–adrenergic receptor gene in response to short–term agonist exposure, *Proc. Natl. Acad. Sci. USA* 86:4853–4857 (1989).

Comb et al., A cyclic AMP–and phorbol ester–inducible DNA element, *Nature* 323:353–356 (1986).

Conroy et al., The α5 gene product assembles with multiple acetylcholine receptor subunits to form distinctive receptor subtypes in brain, *Neuron* 9:679–691 (1992).

Conroy and Berg, Neurons can maintain multiple classes of nicotinic acetylcholine receptors distinguished by different subunit compositions, *J. Biol. Chem.* 270(9):4424–4431 (1995).

Conti–Tronconi et al., Brain and muscle nicotinic acetylcholine receptors are different but homologous proteins, *Proc. Natl. Acad. Sci. USA* 82:5208–5212 (1985).

Cooper et al., Pentameric structure and subunit stoichiometry of a neuronal nicotinic acetylcholine receptor, *Nature* 350:235–238 (1991).

Cordon–Cardo et al., The trk tyrosine protein kinase mediates the mitogenic properties of nerve growth factor and neurotrophin–3, *Cell* 66:173–183 (1991).

Cotecchia et al., Multiple second messenger pathways of a α–adrenergic receptor subtypes expressed in eukaryotic cells, *J. Biol. Chem.* 265(1):63–69 (1990).

Couturier et al., A neuronal nicotinic acetylcholine receptor subunit (α7) is developmentally regulated and forms a homo–oligomeric channel blocked by α–BTX, *Neuron* 5:847–856 (1990).

Cross et al., Enhancement by 5–hydroxytryptamine and analogues of desensitization of neuronal and muscle nicotinic receptors expressed in Xenopus oocytes, *Br. J. Pharmacol.* 114:1636–1640 (1995).

Curran et al., Barium modulates c–fos expression and post–translational modification, *Proc. Natl. Acad. Sci. USA* 83:8521–8524 (1986).

Curran et al., FBJ murine osteosarcoma virus: Identification and molecular cloning of biologically active proviral DNA, *J. Virology* 44(2):674–682 (1982).

Dascal, The use of Xenopus oocytes for the study of ion channels, *CRC Crit. Rev. Biochem.* 22(4):317–387 (1987).

Deneris et al., Primary structure and expression of β2: A novel subunit of neuronal nicotinic acetylcholine receptors, *Neuron* 1:45–54 (1988).

Deneris et al., Pharmacological and functional diversity of neuronal nicotinic acetylcholine receptors, *Trends Pharmacol. Sci.* 12:34–40 (1991).

Deneris et al., $\beta_3$: A new member of nicotinic acetylcholine receptor gene family is expressed in brain, *J. Biol. Chem.* 264(11):6268–6272 (1989).

Denhardt, A membrane–filter technique for the detection of complementary DNA, *Biochem. Biophys. Res. Commun.* 23:641–646 (1966).

Deschamps et al., Identification of a transcriptional enhancer element upstream from the proto–oncogene fos, *Science* 230:1174–1177 (1985).

Devreotes, *Dictyostelium discoideum:* A model system for cell–cell interactions in development, *Science* 245:1054–1058 (1989).

deWet et al., Firefly luciferase gene: Structure and expression in mammalian cells, *Mol. Cell. Biol.* 7:725–737 (1987).

Didier et al., Characterization of nicotinic acetylcholine receptors expressed in primary cultures of cerebellar granule cells, *Mol. Brain Res.* 30:17–28 (1995).

Dixon et al., Cloning of the gene and cDNA for mammalian β–adrenergic receptor and homology with rhodopsin, *Nature* 321:75–79 (1986).

Doolittle, *Of URFS and ORFS. A Primer on How to Analyze Derived Amino Acid Sequences,* selected pages, University Science Books, Mill Valley, CA (1986).

Doucette–Stamm et al., Cloning and sequence of the human α7 nicotinic acetylcholine receptor, *Drug Development Research* 30:252–256 (1993).

Duvoisin et al., The functional diversity of the neuronal nicotinic acetylcholine receptors is increased by a novel subunit: β4, *Neuron* 3:487–496 (1989).

Elliott et al., Cloning and functional expression of human neuronal nicotinic acetylcholine receptor subunits α2, α3, α4, α7, β2 and β4, *Soc. Neurosci. Abstr.* 19(1–3):69 (1993).

Ellis et al., Replacement of insulin receptor tyrosine residues 1162 and 1163 compromises insulin–stimulated kinase activity and uptake of 2–deoxyglucose, *Cell* 45:721–732 (1986).

Ellis et al., Sequence and expression of mRNAs encoding the $\alpha_1$ and $\alpha_2$ subunits of a DHP–sensitive calcium channel, *Science* 241:1661–1664 (1988).

EMBASE abstract #87032747, Gonda et al., A molecular basis for growth regulation in normal and neoplastic hemopoiesis, *Cancer Rev. (Denmark)* 3:58–90 (1986).

EMBASE abstract #90361366, Roux et al., Nuclear localization of c–fos, but not v–fos proteins, is controlled by extracellular signals, *Cell* 63(2):341–351 (1990).

EMBASE abstract #90191445, Kouzarides et al., Behind the fos and jun leucine zipper, *Cancer Cells* 1(3):71–76 (1989).

Engebrecht and Silverman, Identification of genes and gene products necessary for bacterial bioluminescence, *Proc. Natl. Acad. Sci. USA* 1:4154–4158 (1984).

Fanger et al., Differential expression of sodium channels and nicotinic acetylcholine receptor channels in nnr variants of the PC12 pheochromocytoma cell line, *J. Membrane Biol.* 144:71–80 (1995).

Figl et al., Regions of β4•β2 subunit chimeras that contribute to the agonist selectivity of neuronal nicotinic receptors, *FEBS Lttrs.* 308(3):245–248 (1992).

Fink et al., The CGTCA sequence motif is essential for biological activity of the vasoactive intestinal peptide gene cAMP–regulated enhancer, *Proc. Natl. Acad. Sci. USA* 85:6662–6666 (1988).

Firtel et al., G protein linked signal transduction pathways in development: Dictyostelium as an experimental system, *Cell* 58:235–239 (1989).

Fornasari et al., Molecular cloning of human neuronal nicotinic receptor $\alpha_3$–subunit, *Neurosci. Lttrs.* 111:351–356 (1990).

Frielle et al., Cloning of the cDNA for the human $\beta_1$–adrenergic receptor, *Proc. Natl. Acad. Sci. USA* 84:7920–7924 (1987).

Galzi et al., Mutations in the channel domain of a neuronal nicotinic receptor convert ion selectivity from cationic to anionic, *Nature* 359:500–505 (1992).

Galzi and Changeux, Neuronal nicotinic receptors: Molecular organization and regulations, *Neuropharmacology* 34(6):563–582 (1995).

Gautam et al., A G protein gamma subunit shares homology with ras proteins, *Science* 244:971–974 (1989).

Gilman, G proteins: Transducers of receptor–generated signals, *Ann. Rev. Biochem.* 56:615–649 (1987).

Goldman et al. Members of a nicotinic acetylcholine receptor gene family are expressed in different regions of the mammalian central nervous system, *Cell* 48:965–973 (1987).

Gopalkrishnan et al., Stable expression and pharmacological properties of the human $\alpha_7$ nicotinic acetylcholine receptor, *Eur. J. Pharmacol.* 290:237–246 (1995).

Gorman et al., Recombinant genomes which express chloramphenicol acetyltransferase in mammalian cells, *Mol. Cell. Biol.* 2(9):1044–1051 (1982).

Gotti et al., Acetylcholine operated ion channel and α–bungarotoxin binding site in a human neuroblastoma cell line reside on different molecules, *Biochem. Biophys. Res. Commun.* 137(3):1141–1147 (1986).

Goyal, Muscarinic receptor subtypes, *N. Engl. J. Med.* 321(15):1022–1029 (1989).

Green berg et al., Stimulation of neuronal acetylcholine receptors induces rapid gene transcription, *Science* 234:80–83 (1986).

Groebe et al., α–connotoxins selectively inhibit one of the two accetylcholine binding sites of the nicotinic receptors, *Mol. Pharmacol. 48:*105–111 (1995).

Hall et al., Expression and regulation of *Escherichia coli* lacZ gene fusions in mammalian cells, *J. Molec. Appl. Genet. 2:*101–109 (1983).

Halvorsen et al., Affinity labeling of neuronal acetylcholine receptor subunits with an α–neurotoxin that blocks receptor function, *J. Neurosci. 7(8)*:2547–2555 (1987).

Hamill et al., Improved patch–clamp techniques for high–resolution current recording from cells and cell–free membrane patches, *Pflugers Arch. 391:*85–100 (1981).

Herschman, Extracellular signals, transcriptional responses and cellular specificity, *Trends Biochem. Sci. 14:*455–458 (1989).

Hollman et al., Cloning by functional expression of a member of the gluatmate receptor family, *Nature 342:*643–648 (1989).

Horwitz et al., Muscarinic receptor stimulation increases inositol–phospholipid metabolism and inhibits cyclic AMP accumulation in PC12 cells, *J. Neurochem. 53:*197–204 (1989).

Howard et al., Expression of nicotinic acetylcholine receptors and subunit mRNA transcripts in cultures of neural crest cells, *Dev. Biol. 170:*479–495 (1995).

Hussy et al., Agonist and antagonist effects of nicotine on chick neuronal nicotinic receptors are defined by α and β subunits, *J. Neurophysiol. 72(3)*:1317–1326 (1994).

Ishikawa et al., Acetylcholine receptors of human skeletal muscle: A species difference detected by snake neurotoxins, *Brain Res. 346:*82–88 (1985).

Jay et al., Primary structure of the γ subunit of the DHP–sensitive calcium channel from skeletal muscle, *Science 248:*490–492 (1990).

Johnson et al., Expression and structure of the human NGF receptor, *Cell 47:*545–554 (1986).

Julius et al., Molecular characterization of a functional cDNA encoding the serotonin 1c receptor, *Science 241:*558–564 (1988).

Julius et al., The 5HT2 receptor defines a family of structurally distinct but functionally conserved serotonin receptors, *Proc. Natl. Acad. Sci USA 87:*928–932 (1990).

Kayano et al., Primary structure of rat brain sodium channel III deduced from the cDNA sequence, *FEBS Lttrs. 228:*187–194 (1988).

Klein et al., A chemoattractant receptor controls development in *Dictyostelium discoideum*, *Science 241:*1467–1472 (1988).

Kobilka et al., Cloning, sequencing, and expression of the gene coding for the human platelet $\alpha_2$–adrenergic receptor, *Science 238:*650–656 (1987).

Kobilka et al., An intronless gene encoding a potential member of the family of receptors coupled to guanine nucleotide regulatory proteins, *Nature 329:*75–79 (1987).

Kurosaki et al., Functional properties of nicotinic acetylcholine receptor subunits expressed in various combinations, *FEBS Lttrs. 214(2)*:253–258 (1987).

Lamb et al., Demonstration in living cells of an intragenic negative regulatory element within the rodent c–fos gene, *Cell*, 61:485–496 (1990).

Lambert et al., Muscarinic receptor binding characteristics of a human neuroblastomas SK–N–SH and its clones SH–SY5Y and SH–EP1, *Eur. J. Pharmacol. 165:*71–77 (1988).

Larsson et al., In vitro binding of $^3$H–acetylcholine to nicotinic receptors in rodent and human brain, *J. Neural Transm. 69:*3–18 (1987).

Lathe, Synthetic oligonucleotide probes deduced from amino acid sequence data theoretical and practical considerations, *J. Mol. Biol. 183:*1–12 (1984).

Levitan et al., Structural and functional basis for $GABA_A$ receptor heterogeneity, *Nature 335:*76–79 (1988).

Listerud et al., Functional contribution of neuronal AChR subunits revealved by antisense oligonucleotides, *Science 254:*1518–1521 (1991).

Lloyd et al., SIB–1765F, a novel nicotinic agonist: Profile in models of extrapyramidal motor dysfunction, *Soc. Neurosci. Abstr.* (1995).

Lobron et al., Cellular distribution in the rat telencephalon of mRNAs encoding for the α3 and α4 subunits of the nicotinic acetylcholine receptor, *Mol. Brain Res. 30:*70–76 (1995).

London et al., In vivo labeling of nicotinic acetylcholine receptors in brain with [$^3$H]epibatidine, *Eur. J. Pharmacol. 278:*R1–R2 (1995).

Luetje et al., Both α– and β–subunits contribute to the agonist sensitivity of neuronal nicotinic acetylcholine receptors, *J. Neurosci. 11(3)*:837–845 (1991).

Lukas, Pharmacological distinctions between functional nicotinic acetylcholine receptors on the PC12 rat pheochromocytoma and the TE671 human medulloblastoma, *J. Pharmacol. Exp. Therap. 251(1)*:175–182 (1989).

Lukas et al., Characterization of nicotinic acetylcholine receptors expressed by cells of the SH–SY5Y human neuroblastoma clonal line, *Mol. Cell. Neurosci. 4(1)*:1–12 (1993).

Marshall et al., Sequence and functional expression of a single α subunit of an insect nicotinic acetylcholine receptor, *EMBO J. 9(13)*:4391–4398 (1990).

Marullo et al., Expression of human β1 and β2 adrenergic receptors in *E. coli* as a new tool for ligand screening, *Bio/Technology 7:*923–927 (1989).

Matter–Sadzinski et al., Neuronal specificity of the α7 nicotinic acetylcholine receptor promoter develops during morphogenesis of the central nervous system, *EMBO J. 11(12)*:4529–4538 (1992).

Mauron et al., Structure of chicken genes encoding the nicotinic acetylcholine receptor subunits and their variants, *Soc. Neurosci. Abstr. 17* (1991).

McAllister et al., Establishment of a human medulloblastoma cell line, *Int. J. Cancer 20:*206–212 (1977).

McKinnon, D., Isolation of a cDNA clone coding for a putative second potassium channel indicates the existence of a gene family, *J. Biol. Chem. 264:*8230–8236 (1989).

Mechti et al., Sequence requirements for premature transcription arrest within the first intron of the mouse c–fos gene, *Mol. Cell Biol. 11(5)*:2832–2841 (1991).

Menzaghi et al., SIB–1765F: A novel nicotinic agonist with locomotor stimulant properties in rats, *Soc. Neurosci. Abstr.* (1995).

Michel et al., PC12 phaeochromocytoma cells contain an atypical muscarinic receptor binding site, *Br. J. Pharmacol. 97:*914–920 (1989).

Monteggia et al., Cloning and transient expression of genes encoding the human α4 and β2 neuronal nicotinic acetylcholine receptor (nAChR) subunits, *Gene 155:*189–193 (1995).

Montminy et al., Identification of a cyclic–AMP–responsive element within the rat somatostatin gene, *Proc. Natl. Acad. Sci. USA 83:*6682–6686 (1986).

Morgan et al., Stimulus–transcription coupling in neurons: Role of cellular immediate–early genes, *Trends Neurosci,* 12(11):459–462 (1989).

Nash et al., Molecular cloning of human neuronal nicotinic acetylcholine receptor subunits, *Neurobiol. Neurochem.* 4(7):A2153 (1990).

Nash et al., Molecular cloning and expression of human neuronal nicotinic acetylcholine receptor subunits, *Soc. Neurosci. Abstr. 16:*10 (1990).

Nef et al., Genes expressed in the brain define three distinct neuronal nicotinic acetylcholine receptors, *EMBO J.* 7(3):595–601 (1988).

Nielsen et al., A highly sensitive, mixed–phase assay for chloramphenicol acetyltransferase activity in transfected cells, *Anal. Biochem. 179:*19–23 (1989).

Noda et al., Expression of functional sodium channels from cloned cDNA, *Nature 322:*826–828 (1986).

Noda et al., Existence of distinct sodium channel messenger RNAs in rat brain, *Nature 320:*188–192 (1986).

Nordeen, Luciferase reporter gene vectors for analysis of promoters and enhancers, *BioTechniques* 6(5):454–456 (1988).

Nutter and Adams, Monovalent and divalent cation permeability and block of neuronal nicotinic receptor channels in rat parasympathetic ganglia, *J. Gen. Physiol. 105:*701–723 (1995).

Ortells and Lunt, Evolutionary history of the ligand–gated ion–channel superfamily of receptors, *Trends Neurosci.* 18(3):121–127 (1995).

Ostermann et al., Cellular expression of α4 subunit mRNA of the nicotinic acetylcholine receptor in the developing rat telencephalon, *Neurosci. Lttrs. 192:*21–24 (1995).

Papke et al., The role of the $\beta_4$—subunit in determining the kinetic properties of rat neuronal nicotinic acetylcholine $\alpha_3$—receptors, *J. Physiol. 440:*95–112 (1991).

Patrick et al., Acetylcholine receptor metabolism in a nonfusing muscle cell line, *J. Biol. Chem.* 252(6):2143–2153 (1977).

Peng et al., Human α7 acetylcholine receptor: Cloning of the α7 subunit from the SH–SY5Y cell line and determination of pharmacological properties of native receptors and functional α7 homomers expressed in Xenopus oocytes, *Mol. Pharmacol. 46:*546–554 (1994) (GENBANK accession #X70297 submitted Feb. 4, 1993, publicly available Jun. 1, 1994).

Peralta et al., Distinct primary structures, ligand–binding properties and tissue–specific expression of four human muscarinic acetylcholine receptors, *EMBO J.* 6(13):3923–3929 (1987).

Peralta et al., Differential regulation of PI hydrolysis and adenylyl cyclase by mascarinic receptor subtypes, *Nature, 334:*434–437 (1988).

Picciotto et al., Abnormal avoidance learning in mice lacking functional high–affinity nicotine receptor in the brain, *Nature 374:*65–67 (1995).

Pritchett et al., Importance of a novel $GABA_A$ receptor subunit for benzodiazepine pharmacology, *Nature,* 338:582–585 (1989).

Quik et al., Neuronal nicotinic α–bungarotoxin site, *Can. J. Physiol. Pharmacol. 66:*971–979 (1988).

Quik et al., Neuronal nicotinic α–bungarotoxin site, *Can. J. Physiol. Pharmacol. 66:*971–979 (1988).

Receptor Genetics, Inc. (file of correspondence with SIBIA).

Revah et al., Mutations in the channel domain alter desensitization of a neuronal nicotinic receptor, *Nature 353:*846–849 (1991).

Riabowol et al., The catalytic subunit of cAMP–dependent protein kinase induces expression of genes contraining cAMP–responsive enhancer elements, *Nature 336:*83–86 (1988).

Ruth et al., Primary structure of the β subunit of the DHP–sensitive calcium channel from skeletal muscle, *Science,* 245:1115–1118 (1989).

Sacaan et al., Effect of (±)–epibatidine on the release of catecholamines: Biochemical and behavioral evidence in rats, *Soc. Neurosci. Abstr.* (1995).

Sambrook et al., *Molecular Cloning. A Laboratory Manual,* 2d. Ed., Cold Spring Harbor Laboratory Press (1989).

Sargent, The diversity of neuronal nicotinic acetylcholine receptors, *Annu. Rev. Neurosci. 16:*403–443 (1993).

Sassone–Corsi et al., Induction of proto–oncogene fos transcription through the adenylate cyclase pathway: characterization of a cAMP–responsive element, *Genes Dev.* 2:1529–1538 (1988).

Schilling et al., Regulation of a fos–lacZ fusion gene: A paradigm for quantitative analysis of stimulus–transcription coupling, *Proc. Natl. Acad. Sci. USA 88:*5665–5669 (1991).

Schoepfer et al., The human medulloblastoma cell line TE671 expresses a muscle–like acetylcholine receptor, *FEBS Lttrs.* 226(2):235–240 (1988).

Schoepfer et al., cDNA clones coding for the structural subunit of a chicken brain nicotinic acetylcholine receptor, *Neuron 1:*241–248 (1988).

Schoepfer et al., Brain α–bungarotoxin binding protein cDNAs and MAbs reveal subtypes of this branch of the ligand–gated ion channel gene superfamily, *Neuron 5:*35–48 (1990).

Schoepfer et al., *Molecular Biology of Neuroreceptors and Ion Channels* Maelicke, A. (Ed.), NATO–ASI Series, Springer Vergal, Heidelberg (1989).

Schofield et al., Sequence and functional expression of the $GABA_A$ receptor shows a ligand–gated receptor super–family, *Nature 328:*221–227 (1987).

Séguéla et al., Molecular cloning, functional properties, and distribution of rat brain $\alpha_7$:A nicotinic cation channel highly permeable to calcium, *J. Neurosci.* 13(2):596–604 (1993).

Serra et al., The intact human neuroblastoma cell (SH–SY5Y) exhibits high–affinity [$^3$H]pirenzepine binding associated with hydrolysis of a phosphatidylinositols, *J. Neurochem. 50:*1513–1521 (1988).

Serra et al., Phorbol esters alter muscarinic receptor binding and inhibit polyphosphoinositide breakdown in human neuroblastoma (SH–SY5Y) cells, *Biochem. Biophys. Res. Comm. 140:*160–166 (1988).

Sheng et al., The regulation and function of c–fos and other immediate early genes in the nervous system, *Neuron 4:*477–485 (1990).

Shivers, B.D., Two novel $GABA_A$ receptor subunits exist in distinct neuronal subpopulations, *Neuron 3:*327–337 (1989).

Short et al., Characterization of the phosphoenolpyruvate carboxykinase (GTP) promoter–regulatory region, *J. Biol. Chem. 261:*9721–9726 (1986).

Stauderman et al., Chacterization of recombinant human neuronal nicotinic acetylcholine receptor subtypes α4β4 and α2β4 stably expressed in HEK293 cells, *Soc. Neurosci. Abstr.* (1995).

Stillman et al., Replication and supercoiling of simian virus 40 DNA in cell extracts from human cells, *Mol. Cell.Biol.* 5:2051–2060 (1985).

Stormann et al., Molecular cloning and expression of a dopamine D2 receptor from human retina, *Molec. Pharm.* 37:1–6 (1990).

Strader et al., Structural basis of β–adrenergic receptor function, *FASEB J.* 3:1825–1832 (1989).

Stroud et al., Nicotinic acetylcholine receptor superfamily of ligand–gated ion channels, *Biochemistry* 29(50):11009–11023 (1990).

Stumpo et al., Induction of c–fos sequences involved in induction by insulin and phorbol esters, *J. Biol. Chem.* 263(4):1611–1614 (1988).

Subramani et al., Expression of the mouse dihydrofolate reductase complementary deoxyribonucleic acid in simian virus 40 vectors, *Mol. Cell Biol.* 1:854–864 (1981).

Sugaya et al., Nicotinic acetylcholine receptor subtypes in human frontal cortex: Changes in Alzheimer's disease, *J. Neurosci. Res.* 27:349–359 (1990).

Talib et al., Differential expression of human nicotinic acetylcholine receptor α subunit variants in muscle and non–muscle tissues, *Nucleic Acids Res.* 21(2):233–237 (1993).

Tanabe et al., Primary structure of the receptor for calcium channel blockers from skeletal muscle, *Nature* 328:313–318 (1987).

Tarroni et al., Neuronal–type nicotinic receptors in human neuroblastoma and small–cell lung carcinoma cell lines, *FEBS Lttrs.* 312(1):66–70 (1992) (EMBL Accession number submitted by P.Tarroni Sep. 22, 1992).

Tempel et al., Cloning of a probable potassium channel gene from mouse brain, *Nature* 332:837–839 (1988).

Toh et al., Isolation and characterization of a rat liver alkaline phosphatase gene, *Eur. J. Biochem.* 182:231–238 (1989).

Turchi et al., Effects of nicotinic acetylcholine receptor ligands on behavioral vigilance in rats, *Psychopharmacology* 118:195–205 (1995).

Urlaub et al., Effect of gamma rays at the dihydrofolate reductase locus: Deletions and inversions, *Somatic Cell. Molec. Genet.* 12(6):555–566 (1986).

Verma et al., Proto–oncogene fos: Complex but versatile regulation, *Cell* 51:513–514 (1987).

Vernallis et al., AChR gene products in chick ciliary ganglia: Transcripts, subunits, and receptor subtypes, *Soc. Neurosci. Abstr.* 17:23 (1991).

Vijayaraghavan et al., Nicotinic receptors that bind α–bungarotoxin on neurons raise intracellular free $Ca^{2+}$, *Neuron* 8:353–362 (1992).

Visvader et al., Two adjacent promoter elements mediate nerve growth factor activation of the c–fos gene and bind distinct nuclear complexes, *Proc. Natl. Acad. Sci. USA* 85:9474–9478 (1988).

Wackym et al., Expression of α4 and β2 nicotinic acetylcholine receptor subunit mRNA and localization of α–bungarotoxin binding proteins in the rat vestibular periphery, *Cell Biology International* 19(4):291–300 (1995).

Wada et al., Functional expression of a new pharmacological subtype of brain nicotinic acetylcholine receptor, *Science* 240:330–334 (1988).

Wada et al., Distribution of Alpha2, Alpha3, Alpha4, and Beta2 neuronal nicotinic receptor subunit mRNAs in the central nervous system: A hybridization histochemical study in the rat, *J. Comp. Neurol.* 284:314–335 (1989).

Whiting et al., Structurally different neuronal nicotinic acetylcholine receptor subtypes purified and characterized using monoclonal antibodies, *J. Neurosci.* 7(12):4005–4016 (1987).

Whiting et al., Purification and characterization of a nicotinic acetylcholine receptor from rat brain, *Proc. Natl. Acad. Sci. USA* 84:595–599 (1987).

Whiting et al., Affinity labelling of neuronal acetylcholine receptors localizes acetylcholine–binding sites to their β–subunits, *FEBS Lttrs.* 213(1):55–60 (1987).

Whiting et al., Neuronal nicotinic acetylcholine receptor β–subunit is coded for by the cDNA clone $α_4$, *FEBS Lttrs.* 213(1):459–463 (1987).

Whiting et al., Expression of nicotinic acetylcholine receptor subtypes in brain and retina, *Mol. Brain Res.* 10:61–70 (1991).

Whiting et al., Structural and pharmacological characterization of the major brain nicotinic acetylcholine receptor subtype stably expressed in mouse fibroblasts, *Mol. Pharmacol.* 40:463–472 (1991).

Wigler et al., DNA–mediated transfer of the adenine phosphoribosyltransferase locus into mammalian cells, *Proc. Natl. Acad. Sci. USA* 76:1373–1376 (1979).

Williams et al., Neuronal nicotinic actylcholine receptors, *Drug News & Perspectives* 7(4):205–223 (1995).

Willoughby et al., Molecular cloning of a human neuronal nicotinic acetylcholine receptor β3–like subunit, *Neurosci. Lttrs.* 155:136–139 (1993).

Wilson et al., Inhibitory action of nicotinic antagonists on transmitter release at the neuromuscular junction of the rat, *Neurosci. Lttrs.* 186:29–32 (1995).

Yeh et al., Ultrastructural localization of a platelet–derived growth factor/ v–sis–related protein(s) in cytoplasm and nucleus of simian sarcoma virus–transformed cells, *Proc. Natl. Acad. Sci. USA* 84:2317–2321 (1987).

Ymer et al., $GABA_A$ receptor β subunit heterogeneity: functional expression of cloned cDNAs, *EMBO J.* 8:1665–1670 (1989).

Young et al., Isolation and characterization of a new cellular oncogene encoding a protein with multiple potential transmembrane domains, *Cell* 45:711–719 (1986).

Zipser et al., Mapping functional domains in the promoter region of the herpes thymidine kinase gene, *Proc. Natl. Acad. Sci. USA* 78(10):6276–6280 (1981).

Zoli et al., Developmental regulation of nicotinic ACh receptor subunit mRNAs in the rat central and peripheral nervous systems, *J. Neurosci.* 15(3):1912–1939 (1995).

Zwart et al., Differential modulation of α3β2 and α3β4 neuronal nicotinic receptors expressed in Xenopus oocytes by flufenamic acid and niflumic acid, *J. Neurosci.* 15(3):2168–2178 (1995).

\* cited by examiner

SEQUENCE LISTING

```
(1) GENERAL INFORMATION:

(iii) NUMBER OF SEQUENCES: 18

(2) INFORMATION FOR SEQ ID NO:1:

(i) SEQUENCE CHARACTERISTICS:
        (A) LENGTH: 2277 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 166..1755
        (D) OTHER INFORMATION: /product= "ALPHA-2 SUBUNIT"

(xi) SEQUENCE DESCRIPTION: SEQ ID NO:1:

CAATGACCTG TTTTCTTCTG TAACCACAGG TTCGGTGGTG AGAGGAASCY TCGCAGAATC      60

CAGCAGAATC CTCACAGAAT CCAGCAGCAG CTCTGCTGGG ACATGGTCC ATGGTGCAAC     120

CCACAGCAAA GCCCTGACCT GACCTCCTGA TGCTCAGGAG AAGCCATGGG CCCCTCCTGT    180

CCTGTGTTCC TGTCCTTCAC AAAGCTCAGC CTGTGGTGGC TCCTTCTGAC CCCAGCAGGT    240

GGAGAGGAAG CTAAGCGCCC ACCTCCCAGG GCTCCTGGAG ACCCACTCTC CTCTCCCAGT    300

CCCACGGCAT TGCCGCAGGG AGGCTCGCAT ACCGAGACTG AGGACCGGCT CTTCAAACAC    360

CTCTTCCGGG GCTACAACCG CTGGGCGCGC CCGGTGCCCA ACACTTCAGA CGTGGTGATT    420

GTGCGCTTTG GACTGTCCAT CGCTCAGCTC ATCGATGTGG ATGAGAAGAA CCAAATGATG    480

ACCACCAACG TCTGGCTAAA ACAGGAGTGG AGCGACTACA AACTGCGCTG GAACCCCGCT    540

GATTTTGGCA ACATCACATC TCTCAGGGTC CCTTCTGAGA TGATCTGGAT CCCCGACATT    600

GTTCTCTACA ACAATGCAGA TGGGGAGTTT GCAGTGACCC ACATGACCAA GGCCCACCTC    660

TTCTCCACGG GCACTGTGCA CTGGGTGCCC CCGGCCATCT ACAAGAGCTC CTGCAGCATC    720

GACGTCACCT TCTTCCCCTT CGACCAGCAG AACTGCAAGA TGAAGTTTGG CTCCTGGACT    780

TATGACAAGG CCAAGATCGA CCTGGAGCAG ATGGAGCAGA CTGTGGACCT GAAGGACTAC    840

TGGGAGAGCG GCGAGTGGGC CATCGTCAAT GCCACGGGCA CCTACAACAG CAAGAAGTAC    900

GACTGCTGCG CCGAGATCTA CCCCGACGTC ACCTACGCCT TCGTCATCCG GCGGCTGCCG    960

CTCTTCTACA CCATCAACCT CATCATCCCC TGCCTGCTCA TCTCCTGCCT CACTGTGCTG   1020
```

-continued

```
GTCTTCTACC TGCCCTCCGA CTGCGGCGAG AAGATCACGC TGTGCATTTC GGTGCTGCTG    1080

TCACTCACCG TCTTCCTGCT GCTCATCACT GAGATCATCC CGTCCACCTC GCTGGTCATC    1140

CCGCTCATCG GCGAGTACCT GCTGTTCACC ATGATCTTCG TCACCCTGTC CATCGTCATC    1200

ACCGTCTTCG TGCTCAATGT GCACCACCGC TCCCCCAGCA CCCACACCAT GCCCCACTGG    1260

GTGCGGGGGG CCCTTCTGGG CTGTGTGCCC CGGTGGCTTC TGATGAACCG GCCCCCACCA    1320

CCCGTGGAGC TCTGCCACCC CCTACGCCTG AAGCTCAGCC CCTCTTATCA CTGGCTGGAG    1380

AGCAACGTGG ATGCCGAGGA GAGGGAGGTG GTGGTGGAGG AGGAGGACAG ATGGGCATGT    1440

GCAGGTCATG TGGCCCCCTC TGTGGGCACC CTCTGCAGCC ACGGCCACCT GCACTCTGGG    1500

GCCTCAGGTC CCAAGGCTGA GGCTCTGCTG CAGGAGGGTG AGCTGCTGCT ATCACCCCAC    1560

ATGCAGAAGG CACTGGAAGG TGTGCACTAC ATTGCCGACC ACCTGCGGTC TGAGGATGCT    1620

GACTCTTCGG TGAAGGAGGA CTGGAAGTAT GTTGCCATGG TCATCGACAG GATCTTCCTC    1680

TGGCTGTTTA TCATCGTCTG CTTCCTGGGG ACCATCGGCC TCTTTCTGCC TCCGTTCCTA    1740

GCTGGAATGA TCTGACTGCA CCTCCCTCGA GCTGGCTCCC AGGGCAAAGG GGAGGGTTCT    1800

TGGATGTGGA AGGGCTTTGA ACAATGTTTA GATTTGGAGA TGAGCCCAAA GTGCCAGGGA    1860

GAACAGCCAG GTGAGGTGGG AGGTTGGAGA GCCAGGTGAG GTCTCTCTAA GTCAGGCTGG    1920

GGTTGAAGTT TGGAGTCTGT CCGAGTTTGC AGGGTGCTGA GCTGTATGGT CCAGCAGGGG    1980

AGTAATAAGG GCTCTTCCGG AAGGGGAGGA AGCGGGAGGC AGGGCCTGCA CCTGATGTGG    2040

AGGTACAGGG CAGATCTTCC CTACCGGGGA GGGATGGATG GTTGGATACA GGTGGCTGGG    2100

CTATTCCATC CATCTGGAAG CACATTTGAG CCTCCAGGCT TCTCCTTGAC GTCATTCCTC    2160

TCCTTCCTTG CTCCAAAATG GCTCTGCACC AGCCGGCCCC CAGGAGGTCT GGCAGAGCTG    2220

AGAGCCATGG CCTGCAGGGG CTCCATATGT CCCTACGCGT GCAGCAGGCA AACAAGA       2277
```

(2) INFORMATION FOR SEQ ID NO:2:

(i) SEQUENCE CHARACTERISTICS:
        (A) LENGTH: 529 amino acids
        (B) TYPE: amino acid
        (D) TOPOLOGY: unknown (ii) MOLECULE TYPE: protein (xi) SEQUENCE DESCRIPTION: SEQ ID NO:2:

```
Met Gly Pro Ser Cys Pro Val Phe Leu Ser Phe Thr Lys Leu Ser Leu
1               5                   10                  15

Trp Trp Leu Leu Leu Thr Pro Ala Gly Gly Glu Glu Ala Lys Arg Pro
            20                  25                  30

Pro Pro Arg Ala Pro Gly Asp Pro Leu Ser Ser Pro Ser Pro Thr Ala
        35                  40                  45

Leu Pro Gln Gly Gly Ser His Thr Glu Thr Glu Asp Arg Leu Phe Lys
    50                  55                  60

His Leu Phe Arg Gly Tyr Asn Arg Trp Ala Arg Pro Val Pro Asn Thr
65                  70                  75                  80

Ser Asp Val Val Ile Val Arg Phe Gly Leu Ser Ile Ala Gln Leu Ile
                85                  90                  95

Asp Val Asp Glu Lys Asn Gln Met Met Thr Thr Asn Val Trp Leu Lys
            100                 105                 110

Gln Glu Trp Ser Asp Tyr Lys Leu Arg Trp Asn Pro Ala Asp Phe Gly
        115                 120                 125
```

```
Asn Ile Thr Ser Leu Arg Val Pro Ser Glu Met Ile Trp Ile Pro Asp
130                 135                 140

Ile Val Leu Tyr Asn Asn Ala Asp Gly Glu Phe Ala Val Thr His Met
145                 150                 155                 160

Thr Lys Ala His Leu Phe Ser Thr Gly Thr Val His Trp Val Pro Pro
                165                 170                 175

Ala Ile Tyr Lys Ser Ser Cys Ser Ile Asp Val Thr Phe Phe Pro Phe
            180                 185                 190

Asp Gln Gln Asn Cys Lys Met Lys Phe Gly Ser Trp Thr Tyr Asp Lys
        195                 200                 205

Ala Lys Ile Asp Leu Glu Gln Met Glu Gln Thr Val Asp Leu Lys Asp
210                 215                 220

Tyr Trp Glu Ser Gly Glu Trp Ala Ile Val Asn Ala Thr Gly Thr Tyr
225                 230                 235                 240

Asn Ser Lys Lys Tyr Asp Cys Cys Ala Glu Ile Tyr Pro Asp Val Thr
                245                 250                 255

Tyr Ala Phe Val Ile Arg Arg Leu Pro Leu Phe Tyr Thr Ile Asn Leu
            260                 265                 270

Ile Ile Pro Cys Leu Leu Ile Ser Cys Leu Thr Val Leu Val Phe Tyr
        275                 280                 285

Leu Pro Ser Asp Cys Gly Glu Lys Ile Thr Leu Cys Ile Ser Val Leu
290                 295                 300

Leu Ser Leu Thr Val Phe Leu Leu Leu Ile Thr Glu Ile Ile Pro Ser
305                 310                 315                 320

Thr Ser Leu Val Ile Pro Leu Ile Gly Glu Tyr Leu Leu Phe Thr Met
                325                 330                 335

Ile Phe Val Thr Leu Ser Ile Val Ile Thr Val Phe Val Leu Asn Val
            340                 345                 350

His His Arg Ser Pro Ser Thr His Thr Met Pro His Trp Val Arg Gly
        355                 360                 365

Ala Leu Leu Gly Cys Val Pro Arg Trp Leu Leu Met Asn Arg Pro Pro
370                 375                 380

Pro Pro Val Glu Leu Cys His Pro Leu Arg Leu Lys Leu Ser Pro Ser
385                 390                 395                 400

Tyr His Trp Leu Glu Ser Asn Val Asp Ala Glu Glu Arg Glu Val Val
                405                 410                 415

Val Glu Glu Glu Asp Arg Trp Ala Cys Ala Gly His Val Ala Pro Ser
            420                 425                 430

Val Gly Thr Leu Cys Ser His Gly His Leu His Ser Gly Ala Ser Gly
        435                 440                 445

Pro Lys Ala Glu Ala Leu Leu Gln Glu Gly Glu Leu Leu Leu Ser Pro
450                 455                 460

His Met Gln Lys Ala Leu Glu Gly Val His Tyr Ile Ala Asp His Leu
465                 470                 475                 480

Arg Ser Glu Asp Ala Asp Ser Ser Val Lys Glu Asp Trp Lys Tyr Val
                485                 490                 495

Ala Met Val Ile Asp Arg Ile Phe Leu Trp Leu Phe Ile Ile Val Cys
            500                 505                 510

Phe Leu Gly Thr Ile Gly Leu Phe Leu Pro Pro Phe Leu Ala Gly Met
        515                 520                 525

Ile
```

(2) INFORMATION FOR SEQ ID NO:3:

(i) SEQUENCE CHARACTERISTICS:
    (A) LENGTH: 1654 base pairs
    (B) TYPE: nucleic acid
    (C) STRANDEDNESS: both
    (D) TOPOLOGY: both (ii) MOLECULE TYPE: cDNA (ix) FEATURE:
    (A) NAME/KEY: CDS
    (B) LOCATION: 39..1553
    (D) OTHER INFORMATION: /product= "ALPHA-3 SUBUNIT"

(xi) SEQUENCE DESCRIPTION: SEQ ID NO:3:

```
CCGACCGTCC GGGTCCGCGG CCAGCCCGGC CACCAGCCAT GGGCTCTGGC CCGCTCTCGC      60
TGCCCCTGGC GCTGTCGCCG CCGCGGCTGC TGCTGCTGCT GCTGTCTCTG CTGCCAGTGG     120
CCAGGGCCTC AGAGGCTGAG CACCGTCTAT TTGAGCGGGT GTTTGAAGAT TACAATGAGA     180
TCATCCGGCC TGTAGCCAAC GTGTCTGACC CAGTCATCAT CCATTTCGAG GTGTCCATGT     240
CTCAGCTGGT GAAGGTGGAT GAAGTAAACC AGATCATGGA GACCAACCTG TGGCTCAAGC     300
AAATCTGGAA TGACTACAAG CTGAAGTGGA ACCCCTCTGA CTATGGTGGG GCAGAGTTCA     360
TGCGTGTCCC TGCACAGAAG ATCTGGAAGC AGACATTGT GCTGTATAAC AATGCTGTTG     420
GGGATTTCCA GGTGGACGAC AAGACCAAAG CCTTACTCAA GTACACTGGG GAGGTGACTT     480
GGATACCTCC GGCCATCTTT AAGAGCTCCT GTAAAATCGA CGTGACCTAC TTCCCGTTTG     540
ATTACCAAAA CTGTACCATG AAGTTCGGTT CCTGGTCCTA CGATAAGGCG AAAATCGATC     600
TGGTCCTGAT CGGCTCTTCC ATGAACCTCA AGGACTATTG GGAGAGCGGC GAGTGGGCCA     660
TCATCAAAGC CCCAGGCTAC AAACACGACA TCAAGTACAC CTGCTGCGAG GAGATCTACC     720
CCGACATCAC ATACTCGCTG WWCATCCGGC GGCTGTCGTT GTTCTACACC ATCAWCCTCA     780
TCATCCGCTG GCTGATCATC TCCTTCATCA CTGTGGTCGT CTCCTACCTG CCCTCCGACT     840
GCGGCGAGAA GGTGACCCTG TGYATTTCTG TCCTCCTCTC CCTGACGGTG TTTCTCCTGG     900
TGATCACTGA GACCATCCCT TCCACCTCGC TGGTCATCCC CCTGATTGGA GAGTACCTCC     960
TGWWCACCAT GATTTGTGTA ACCTTGTCCA TCGACATCAC CGTCTGCGTG CTCAACGTGC    1020
ACTACAGAAC CCCGACGACA CACACAATGC CCTCATGGGT GAAGACTGTA TTCTTGAMCC    1080
TGCTCCCCAG GGTCATGTWC ATGACCAGGC CAACAAGCAA CGAGGGCAAC GCTCAGAAGC    1140
CGAGGCCCCT CTACGGTGCC GAGCTCTCAA ATCTGAATTG CTTCAGCCGC GCAGAGTCCA    1200
AAGGCTGCAA GGAGGGCTAC CCCTGCCAGG ACGGGATGTG TGGTTACTGC CACCACCGCA    1260
GGATAAAAAT CTCCAATTTC AGTGCTAACC TCACGAGAAG CTCTAGTTCT GAATCTGTTG    1320
ATGCTGTGCT GTCCCTCTCT GCTTTGTCAC CAGAAATCAA AGAAGCCATC CAAAGTGTCA    1380
AGTATATTGC TGAAAATATG AAAGCACAAA ATGAAGCCAA AGAGATTCAA GATGATTGGA    1440
AGTATGTTGC CATGGTGATT GATCGTATTT TTCTGTGGGT TTTCACCCTG GTGTGCATTC    1500
TAGGGACAGC AGGATTGTTT CTGCAACCCC TGATGGCCAG GGAAGATGCA TAAGCACTAA    1560
GCTGTGTGCC TGCCTGGGAG ACTTCCTTGT GTCAGGGCAG GAGGAGGCTG CTTCCTAGTA    1620
AGAACGTACT TTCTGTTATC AAGCTACCAG CTTT                                1654
```

(2) INFORMATION FOR SEQ ID NO:4:

(i) SEQUENCE CHARACTERISTICS:
        (A) LENGTH: 504 amino acids
        (B) TYPE: amino acid
        (D) TOPOLOGY: unknown (ii) MOLECULE TYPE: protein (xi) SEQUENCE DESCRIPTION: SEQ ID NO:4:

Met Gly Ser Gly Pro Leu Ser Leu Pro Leu Ala Leu Ser Pro Pro Arg
1               5                   10                  15

Leu Leu Leu Leu Leu Leu Ser Leu Leu Pro Val Ala Arg Ala Ser Glu
            20                  25                  30

Ala Glu His Arg Leu Phe Glu Arg Leu Phe Glu Asp Tyr Asn Glu Ile
            35                  40                  45

Ile Arg Pro Val Ala Asn Val Ser Asp Pro Val Ile Ile His Phe Glu
50                  55                  60

Val Ser Met Ser Gln Leu Val Lys Val Asp Glu Val Asn Gln Ile Met
65                  70                  75                  80

Glu Thr Asn Leu Trp Leu Lys Gln Ile Trp Asn Asp Tyr Lys Leu Lys
            85                  90                  95

Trp Asn Pro Ser Asp Tyr Gly Gly Ala Glu Phe Met Arg Val Pro Ala
            100                 105                 110

Gln Lys Ile Trp Lys Pro Asp Ile Val Leu Tyr Asn Asn Ala Val Gly
            115                 120                 125

Asp Phe Gln Val Asp Asp Lys Thr Lys Ala Leu Leu Lys Tyr Thr Gly
130                 135                 140

Glu Val Thr Trp Ile Pro Pro Ala Ile Phe Lys Ser Ser Cys Lys Ile
145                 150                 155                 160

Asp Val Thr Tyr Phe Pro Phe Asp Tyr Gln Asn Cys Thr Met Lys Phe
            165                 170                 175

Gly Ser Trp Ser Tyr Asp Lys Ala Lys Ile Asp Leu Val Leu Ile Gly
            180                 185                 190

Ser Ser Met Asn Leu Lys Asp Tyr Trp Glu Ser Gly Glu Trp Ala Ile
            195                 200                 205

Ile Lys Ala Pro Gly Tyr Lys His Asp Ile Lys Tyr Ser Cys Cys Glu
            210                 215                 220

Glu Ile Tyr Pro Asp Ile Thr Tyr Ser Leu Xaa Ile Arg Arg Leu Ser
225                 230                 235                 240

Leu Phe Tyr Thr Ile Xaa Leu Ile Ile Arg Trp Leu Ile Ile Ser Phe
            245                 250                 255

Ile Thr Val Val Val Ser Tyr Leu Pro Ser Asp Cys Gly Glu Lys Val
            260                 265                 270

Thr Leu Cys Ile Ser Val Leu Leu Ser Leu Thr Val Phe Leu Leu Val
            275                 280                 285

Ile Thr Glu Thr Ile Pro Ser Thr Ser Leu Val Ile Pro Leu Ile Gly
            290                 295                 300

Glu Tyr Leu Leu Xaa Thr Met Ile Cys Val Thr Leu Ser Ile Asp Ile
305                 310                 315                 320

Thr Val Cys Val Leu Asn Val His Tyr Arg Thr Pro Thr Thr His Thr
            325                 330                 335

Met Pro Ser Trp Val Lys Thr Val Phe Leu Xaa Leu Leu Pro Arg Val
            340                 345                 350

Met Xaa Met Thr Arg Pro Thr Ser Asn Glu Gly Asn Ala Gln Lys Pro
            355                 360                 365

Arg Pro Leu Tyr Gly Ala Glu Leu Ser Asn Leu Asn Cys Phe Ser Arg
            370                 375                 380

Ala Glu Ser Lys Gly Cys Lys Glu Gly Tyr Pro Cys Gln Asp Gly Met
385                 390                 395                 400

```
Cys Gly Tyr Cys His His Arg Arg Ile Lys Ile Ser Asn Phe Ser Ala
            405                 410                 415

Asn Leu Thr Arg Ser Ser Ser Glu Ser Val Asp Ala Val Leu Ser
        420                 425                 430

Leu Ser Ala Leu Ser Pro Glu Ile Lys Glu Ala Ile Gln Ser Val Lys
            435                 440                 445

Tyr Ile Ala Glu Asn Met Lys Ala Gln Asn Glu Ala Lys Glu Ile Gln
        450                 455                 460

Asp Asp Trp Lys Tyr Val Ala Met Val Ile Asp Arg Ile Phe Leu Trp
465                 470                 475                 480

Val Phe Thr Leu Val Cys Ile Leu Gly Thr Ala Gly Leu Phe Leu Gln
            485                 490                 495

Pro Leu Met Ala Arg Glu Asp Ala
            500
```

(2) INFORMATION FOR SEQ ID NO:5:

(i) SEQUENCE CHARACTERISTICS:
        (A) LENGTH: 2363 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 173..2056
        (D) OTHER INFORMATION: /product= "ALPHA-4 SUBUNIT"

(xi) SEQUENCE DESCRIPTION: SEQ ID NO:5:

```
GCGCTCGCTG CGGCGCCGCC GCCGCNCCGC GCGCCACAGG AGAAGGCGAN CCGGGCCCGG    60

CGGCCGAAGC GGCCCGCGAG GCGCGGGAGG CATGAAGTTG GGCGCGCACG GGCCTCGAAG   120

CGGCGGGGAG CCGGGAGCCG CCCGCATCTA GAGCCCGCGA GGTGCGTGCG CCATGGAGCT   180

AGGGGGCCCC GGAGCGCCGC GGCTGCTGCC GCCGCTGCTG CTGCTTCTGG GACCGGCCT    240

CCTGCGCGCC AGCAGCCATG TGGAGACCCG GGCCCACGCC GAGGAGCGGC TCCTGAAGAA   300

ACTCTTCTCC GGTTACAACA AGTGGTCCCG ACCCGTGGCC AACATCTCGG ACGTGGTCCT   360

CGTCCGCTTC GGCCTGTCCA TCGCTCAGCT CATTGACGTG GATGAGAAGA CCAGATGAT    420

GACCACGAAC GTCTGGGTGA AGCAGGAGTG GCACGACTAC AAGCTGCGCT GGGACCCAGC   480

TGACTATGAG AATGTCACCT CCATCCGCAT CCCCTCCGAG CTCATCTGGC GGCCGGACAT   540

CGCCCTCTAC AACAATGCTG ACGGGGACTT CGCGGCCACC CACCTGACCA AGGCCCACCT   600

GTTCCATGAC GGGCGGGTGC AGCGGACTCC CCCGGCCATT TACAAGAGCT CCTGCAGCAT   660

CGACGTCACC TTCTTCCCCT TCGACCAGCA GAACTGCACC ATGAAATTCG GCTCCTGGAC   720

CTACGACAAG GCCAAGATCG ACCTGGTGAA CATGCACAGC CGCGTGGACC AGCTGGACTT   780

CTGGGAGAGT GGCGAGTGGC TCATCTCGGA CGCCGTGGGC ACCTACAACA CCAGGAAGTA   840

CGAGTGCTGC GCCGAGATCT ACCCGGACAT CACCTATGCC TACGCCATCC GGCGGCTGCC   900

GCTCTTCTAC ACCATCAACC TCATCATCCC CTGGCTGCTC ATCTCCTGCC TCACCGCGCT   960

GGTCTTCTAC CTGCCCTCCG AGTGTGGCGA GAAGATCACG CTGTGCATCT CCGTGCTGCT  1020

GTCGCTCACC GTCTTCCTGC TGCTCATCAC CGAGATCATC CCGTCCACCT CACTGGTCAT  1080

CCCACTCATC GGCGAGTACC TGCTGTTCAC CATGATCTTC GTCACCCTGT CCATCGCCAT  1140

CACGGTCTTC GTGCTCAACG TGCACCACCG CTCGCCACGC ACGCACACCA TGCCCACCTG  1200
```

-continued

```
GGTACGCAGG GTCTTCCTGG ACATCGTGCC ACGCCTGCTC CTCATGAAGC GGCCGTCCGT      1260

GGTCAAGGAC AATTGCCGGC GGCTCATCGA GTCCATGCAT AAGATGGCCA GTGCCCCGCG      1320

CTTCTGGCCC GAGCCAGAAG GGGAGCCCCC TGCCACGAGC GGCACCCAGA GCCTGCACCC      1380

TCCCTCACCG TCCTTCTGCG TCCCCCTGGA TGTGCCGGCT GAGCCTGGGC CTTCCTGCAA      1440

GTCACCCTCC GACCAGCTCC CTCCTCAGCA GCCCCTGGAA GCTGAGAAAG CCAGCCCCCA      1500

CCCCTCGCCT GGACCCTGCC GCCCGCCCCA CGGCACCCAG GCACCAGGGC TGGCCAAAGC      1560

CAGGTCCCTC AGCGTCCAGC ACATGTCCAG CCCTGGCGAA GCGGTGGAAG GCGGCGTCCG      1620

GTGCCGGTCT CGGAGCATCC AGTACTGTGT TCCCCGAGAC GATGCCGCCC CCGAGGCAGA      1680

TGGCCAGGCT GCCGGCGCCC TGGCCTCTCG CAACAGCCAC TCGGCTGAGC TCCCACCCCC      1740

AGACCAGCCC TCTCCGTGCA AATGCACATG CAAGAAGGAG CCCTCTTCGG TGTCCCCGAG      1800

CGCCACGGTC AAGACCCGCA GCACCAAAGC GCCGCCGCCG CACCTGCCCC TGTCGCCGGC      1860

CCTGAGCCGG GCGGTGGAGG GCGTCCAGTA CATTGCAGAC CACCTGAAGG CCGAAGACAC      1920

AGACTTCTCG GTGAAGGAGG ACTGGAAGTA CGTGGCCATG GTCATCGACC GCATCTTCCT      1980

CTGGATGTTC ATCATCGTCT GCCTGCTGGG GACGGTGGGC CTCTTCCTGC CGCCCTGGCT      2040

GGCTGGCATG ATCTAGGAAG GGACCGGGAG CCTGCGTGGC CTGGGGCTGC CGYGCACGGG      2100

GCCAGCATCC ATGCGGCCGG CCTGGGGCCG GGCTGGCTTC TCCCTGGACT CTGTGGGGCC      2160

ACACGTTTGC CAAATTTTCC TTCCTGTTCT GTGTCTGCTG TAAGACGGCC TTGGACGGCG      2220

ACACGGCCTC TGGGGAGACC GAGTGTGGAG CTGCTTCCAG TTGGACTCTS GCCTCAGNAG      2280

GCAGCGGCTT GGAGCAGAGG TGGCGGTCGC CGCCTYCTAC CTGCAGGACT CGGGCTAAGT      2340

CCAGCTCTCC CCCTGCGCAG CCC                                             2363
```

(2) INFORMATION FOR SEQ ID NO:6:

(i) SEQUENCE CHARACTERISTICS:
        (A) LENGTH: 627 amino acids
        (B) TYPE: amino acid
        (D) TOPOLOGY: unknown (ii) MOLECULE TYPE: protein (xi) SEQUENCE DESCRIPTION: SEQ ID NO:6:

```
Met Glu Leu Gly Gly Pro Gly Ala Pro Arg Leu Leu Pro Pro Leu Leu
1               5                   10                  15

Leu Leu Leu Gly Thr Gly Leu Leu Arg Ala Ser Ser His Val Glu Thr
            20                  25                  30

Arg Ala His Ala Glu Glu Arg Leu Leu Lys Lys Leu Phe Ser Gly Tyr
        35                  40                  45

Asn Lys Trp Ser Arg Pro Val Ala Asn Ile Ser Asp Val Val Leu Val
    50                  55                  60

Arg Phe Gly Leu Ser Ile Ala Gln Leu Ile Asp Val Asp Glu Lys Asn
65                  70                  75                  80

Gln Met Met Thr Thr Asn Val Trp Val Lys Gln Glu Trp His Asp Tyr
                85                  90                  95

Lys Leu Arg Trp Asp Pro Ala Asp Tyr Glu Asn Val Thr Ser Ile Arg
            100                 105                 110

Ile Pro Ser Glu Leu Ile Trp Arg Pro Asp Ile Ala Leu Tyr Asn Asn
        115                 120                 125

Ala Asp Gly Asp Phe Ala Ala Thr His Leu Thr Lys Ala His Leu Phe
    130                 135                 140
```

-continued

```
His Asp Gly Arg Val Gln Arg Thr Pro Pro Ala Ile Tyr Lys Ser Ser
145                 150                 155                 160

Cys Ser Ile Asp Val Thr Phe Phe Pro Phe Asp Gln Gln Asn Cys Thr
            165                 170                 175

Met Lys Phe Gly Ser Trp Thr Tyr Asp Lys Ala Lys Ile Asp Leu Val
            180                 185                 190

Asn Met His Ser Arg Val Asp Gln Leu Asp Phe Trp Glu Ser Gly Glu
        195                 200                 205

Trp Leu Ile Ser Asp Ala Val Gly Thr Tyr Asn Thr Arg Lys Tyr Glu
    210                 215                 220

Cys Cys Ala Glu Ile Tyr Pro Asp Ile Thr Tyr Ala Tyr Ala Ile Arg
225                 230                 235                 240

Arg Leu Pro Leu Phe Tyr Thr Ile Asn Leu Ile Ile Pro Trp Leu Leu
                245                 250                 255

Ile Ser Cys Leu Thr Ala Leu Val Phe Tyr Leu Pro Ser Glu Cys Gly
            260                 265                 270

Glu Lys Ile Thr Leu Cys Ile Ser Val Leu Leu Ser Leu Thr Val Phe
            275                 280                 285

Leu Leu Leu Ile Thr Glu Ile Ile Pro Ser Thr Ser Leu Val Ile Pro
        290                 295                 300

Leu Ile Gly Glu Tyr Leu Leu Phe Thr Met Ile Phe Val Thr Leu Ser
305                 310                 315                 320

Ile Ala Ile Thr Val Phe Val Leu Asn Val His His Arg Ser Pro Arg
                325                 330                 335

Thr His Thr Met Pro Thr Trp Val Arg Arg Val Phe Leu Asp Ile Val
            340                 345                 350

Pro Arg Leu Leu Leu Met Lys Arg Pro Ser Val Val Lys Asp Asn Cys
        355                 360                 365

Arg Arg Leu Ile Glu Ser Met His Lys Met Ala Ser Ala Pro Arg Phe
    370                 375                 380

Trp Pro Glu Pro Glu Gly Glu Pro Pro Ala Thr Ser Gly Thr Gln Ser
385                 390                 395                 400

Leu His Pro Pro Ser Pro Ser Phe Cys Val Pro Leu Asp Val Pro Ala
                405                 410                 415

Glu Pro Gly Pro Ser Cys Lys Ser Pro Ser Asp Gln Leu Pro Pro Gln
            420                 425                 430

Gln Pro Leu Glu Ala Glu Lys Ala Ser Pro His Pro Ser Pro Gly Pro
        435                 440                 445

Cys Arg Pro Pro His Gly Thr Gln Ala Pro Gly Leu Ala Lys Ala Arg
450                 455                 460

Ser Leu Ser Val Gln His Met Ser Ser Pro Gly Glu Ala Val Glu Gly
465                 470                 475                 480

Gly Val Arg Cys Arg Ser Arg Ser Ile Gln Tyr Cys Val Pro Arg Asp
                485                 490                 495

Asp Ala Pro Glu Ala Asp Gly Gln Ala Gly Ala Leu Ala Ser
            500                 505                 510

Arg Asn Ser His Ser Ala Glu Leu Pro Pro Asp Gln Pro Ser Pro
        515                 520                 525

Cys Lys Cys Thr Cys Lys Lys Glu Pro Ser Ser Val Ser Pro Ser Ala
530                 535                 540

Thr Val Lys Thr Arg Ser Thr Lys Ala Pro Pro Pro His Leu Pro Leu
545                 550                 555                 560
```

```
Ser Pro Ala Leu Ser Arg Ala Val Glu Gly Val Gln Tyr Ile Ala Asp
                565                 570                 575

His Leu Lys Ala Glu Asp Thr Asp Phe Ser Val Lys Glu Asp Trp Lys
            580                 585                 590

Tyr Val Ala Met Val Ile Asp Arg Ile Phe Leu Trp Met Phe Ile Ile
            595                 600                 605

Val Cys Leu Leu Gly Thr Val Gly Leu Phe Leu Pro Pro Trp Leu Ala
        610                 615                 620

Gly Met Ile
625

(2) INFORMATION FOR SEQ ID NO:7:

(i) SEQUENCE CHARACTERISTICS:
        (A) LENGTH: 1828 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 155..1561
        (D) OTHER INFORMATION: /product= "ALPHA-5 SUBUNIT"

(xi) SEQUENCE DESCRIPTION: SEQ ID NO:7:
```

| | |
|---|---|
| CCCGGCGGGA GCTGTGGCGC GGAGCGGCCC CGCTGCTGCG TCTGCCCTCG TTTTGTCTCA | 60 |
| CGACTCACAC TCAGTGCTGC ATTCCCCAAG AGTTCGCGTT CCCCGCGCGG CGGTCGAGAG | 120 |
| GCGGCTGCCC GCGGTCCCGC GCGGGCGCGG GGCG ATG GCG GCG CGG GGG TCA | 172 |

```
                                      Met Ala Ala Arg Gly Ser
                                        1               5

GGG CCC CGC GCG CTC CGC CTG CTG CTC TTG GTC CAG CTG GTC GCG GGG    220
Gly Pro Arg Ala Leu Arg Leu Leu Leu Leu Val Gln Leu Val Ala Gly
             10                  15                  20

CGC TGC GGT CTA GCG GGC GCG GCG GGC GGC GCG CAG AGA GGA TTA TCT    268
Arg Cys Gly Leu Ala Gly Ala Ala Gly Gly Ala Gln Arg Gly Leu Ser
         25                  30                  35

GAA CCT TCT TCT ATT GCA AAA CAT GAA GAT AGT TTG CTT AAG GAT TTA    316
Glu Pro Ser Ser Ile Ala Lys His Glu Asp Ser Leu Leu Lys Asp Leu
     40                  45                  50

TTT CAA GAC TAC GAA AGA TGG GTT CGT CCT GTG GAA CAC CTG AAT GAC    364
Phe Gln Asp Tyr Glu Arg Trp Val Arg Pro Val Glu His Leu Asn Asp
 55                  60                  65                  70

AAA ATA AAA ATA AAA TTT GGA CTT GCA ATA TCT CAA TTG GTG GAT GTG    412
Lys Ile Lys Ile Lys Phe Gly Leu Ala Ile Ser Gln Leu Val Asp Val
                 75                  80                  85

GAT GAG AAA AAT CAG TTA ATG ACA ACA AAC GTC TGG TTG AAA CAG GAA    460
Asp Glu Lys Asn Gln Leu Met Thr Thr Asn Val Trp Leu Lys Gln Glu
             90                  95                 100

TGG ATA GAT GTA AAA TTA AGA TGG AAC CCT GAT GAC TAT GGT GGA ATA    508
Trp Ile Asp Val Lys Leu Arg Trp Asn Pro Asp Asp Tyr Gly Gly Ile
         105                 110                 115

AAA GTT ATA CGT GTT CCT TCA GAC TCT GTC TGG ACA CCA GAC ATC GTT    556
Lys Val Ile Arg Val Pro Ser Asp Ser Val Trp Thr Pro Asp Ile Val
     120                 125                 130

TTG TTT GAT AAT GCA GAT GGA CGT TTT GAA GGG ACC AGT ACG AAA ACA    604
Leu Phe Asp Asn Ala Asp Gly Arg Phe Glu Gly Thr Ser Thr Lys Thr
135                 140                 145                 150

GTC ATC AGG TAC AAT GGC ACT GTC ACC TGG ACT CCA CCG GCA AAC TAC    652
Val Ile Arg Tyr Asn Gly Thr Val Thr Trp Thr Pro Pro Ala Asn Tyr
```

```
                    155                 160                 165
AAA AGT TCC TGT ACC ATA GAT GTC ACG TTT TTC CCA TTT GAC CTT CAG    700
Lys Ser Ser Cys Thr Ile Asp Val Thr Phe Phe Pro Phe Asp Leu Gln
            170                 175                 180

AAC TGT TCC ATG AAA TTT GGT TCT TGG ACT TAT GAT GGA TCA CAG GTT    748
Asn Cys Ser Met Lys Phe Gly Ser Trp Thr Tyr Asp Gly Ser Gln Val
                185                 190                 195

GAT ATA ATT CTA GAG GAC CAA GAT GTA GAC AAG AGA GAT TTT TTT GAT    796
Asp Ile Ile Leu Glu Asp Gln Asp Val Asp Lys Arg Asp Phe Phe Asp
    200                 205                 210

AAT GGA GAA TGG GAG ATT GTG AGT GCA ACA GGG AGC AAA GGA AAC AGA    844
Asn Gly Glu Trp Glu Ile Val Ser Ala Thr Gly Ser Lys Gly Asn Arg
215                 220                 225                 230

ACC GAC AGC TGT TGC TGG TAT CCG TAT GTC ACT TAC TCA TTT GTA ATC    892
Thr Asp Ser Cys Cys Trp Tyr Pro Tyr Val Thr Tyr Ser Phe Val Ile
                235                 240                 245

AAG CGC CTG CCT CTC TTT TAT ACC TTG TTC CTT ATA ATA CCC TGT ATT    940
Lys Arg Leu Pro Leu Phe Tyr Thr Leu Phe Leu Ile Ile Pro Cys Ile
                250                 255                 260

GGG CTC TCA TTT TTA ACT GTA CTT GTC TTC TAT CTT CCT TCA AAT GAA    988
Gly Leu Ser Phe Leu Thr Val Leu Val Phe Tyr Leu Pro Ser Asn Glu
            265                 270                 275

GGT GAA AAG ATT TGT CTC TGC ACT TCA GTA CTT GTG TCT TTG ACT GTC   1036
Gly Glu Lys Ile Cys Leu Cys Thr Ser Val Leu Val Ser Leu Thr Val
        280                 285                 290

TTC CTT CTG GTT ATT GAA GAG ATC ATA CCA TCA TCT TCA AAA GTC ATA   1084
Phe Leu Leu Val Ile Glu Glu Ile Ile Pro Ser Ser Ser Lys Val Ile
295                 300                 305                 310

CCT CTA ATT GGA GAG TAT CTG GTA TTT ACC ATG ATT TTT GTG ACA CTG   1132
Pro Leu Ile Gly Glu Tyr Leu Val Phe Thr Met Ile Phe Val Thr Leu
                315                 320                 325

TCA ATT ATG GTA ACC GTC TTC GCT ATC AAC ATT CAT CAT CGT TCT TCC   1180
Ser Ile Met Val Thr Val Phe Ala Ile Asn Ile His His Arg Ser Ser
            330                 335                 340

TCA ACA CAT AAT GCC ATG GCG CCT TTG GTC CGC AAG ATA TTT CTT CAC   1228
Ser Thr His Asn Ala Met Ala Pro Leu Val Arg Lys Ile Phe Leu His
        345                 350                 355

ACG CTT CCC AAA CTG CTT TGC ATG AGA AGT CAT GTA GAC AGG TAC TTC   1276
Thr Leu Pro Lys Leu Leu Cys Met Arg Ser His Val Asp Arg Tyr Phe
    360                 365                 370

ACT CAG AAA GAG GAA ACT GAG AGT GGT AGT GGA CCA AAA TCT TCT AGA   1324
Thr Gln Lys Glu Glu Thr Glu Ser Gly Ser Gly Pro Lys Ser Ser Arg
375                 380                 385                 390

AAC ACA TTG GAA GCT GCG CTC AAT TCT ATT CGC TAC ATT ACA AGA CAC   1372
Asn Thr Leu Glu Ala Ala Leu Asn Ser Ile Arg Tyr Ile Thr Arg His
                395                 400                 405

ATC ATG AAG GAA AAT GAT GTC CGT GAG GTT GTT GAA GAT TGG AAA TTC   1420
Ile Met Lys Glu Asn Asp Val Arg Glu Val Val Glu Asp Trp Lys Phe
            410                 415                 420

ATA GCC CAG GTT CTT GAT CGG ATG TTT CTG TGG ACT TTT CTT TTC GTT   1468
Ile Ala Gln Val Leu Asp Arg Met Phe Leu Trp Thr Phe Leu Phe Val
        425                 430                 435

TCA ATT GTT GGA TCT CTT GGG CTT TTT GTT CCT GTT ATT TAT AAA TGG   1516
Ser Ile Val Gly Ser Leu Gly Leu Phe Val Pro Val Ile Tyr Lys Trp
    440                 445                 450

GCA AAT ATA TTA ATA CCA GTT CAT ATT GGA AAT GCA AAT AAG TGAAGCCTCC 1568
Ala Asn Ile Leu Ile Pro Val His Ile Gly Asn Ala Asn Lys
455                 460                 465

CAAGGGACTG AAGTATACAT TTAGTTAACA CACATATATC TGATGGCACC TATAAAATTA   1628
```

```
TGAAAATGTA AGTTATGTGT TAAATTTAGT GCAAGCTTTA ACAGACTAAG TTGCTAACCT      1688

CAATTTATGT TAACAGATGA TCCATTTGAA CAGTTGGCTG TATGACTGAA GTAATAACTG      1748

ATGAGATACA TTTGATCTTG TAAAAATAGC AAAATATTAT CTGAACTGGA CTAGTGAAAA      1808

ATCTAGTATT TGTATCCTGG                                                  1828
```

(2) INFORMATION FOR SEQ ID NO:8:

(i) SEQUENCE CHARACTERISTICS:
        (A) LENGTH: 468 amino acids
        (B) TYPE: amino acid
        (D) TOPOLOGY: linear (ii) MOLECULE TYPE: protein (xi) SEQUENCE DESCRIPTION: SEQ ID NO:8:

```
Met Ala Ala Arg Gly Ser Gly Pro Arg Ala Leu Arg Leu Leu Leu
 1               5                  10                  15

Val Gln Leu Val Ala Gly Arg Cys Gly Leu Ala Gly Ala Gly Gly
                20                  25                  30

Ala Gln Arg Gly Leu Ser Glu Pro Ser Ser Ile Ala Lys His Glu Asp
            35                  40                  45

Ser Leu Leu Lys Asp Leu Phe Gln Asp Tyr Glu Arg Trp Val Arg Pro
50                  55                  60

Val Glu His Leu Asn Asp Lys Ile Lys Ile Lys Phe Gly Leu Ala Ile
65                  70                  75                  80

Ser Gln Leu Val Asp Val Asp Glu Lys Asn Gln Leu Met Thr Thr Asn
                85                  90                  95

Val Trp Leu Lys Gln Glu Trp Ile Asp Val Lys Leu Arg Trp Asn Pro
            100                 105                 110

Asp Asp Tyr Gly Gly Ile Lys Val Ile Arg Val Pro Ser Asp Ser Val
            115                 120                 125

Trp Thr Pro Asp Ile Val Leu Phe Asp Asn Ala Asp Gly Arg Phe Glu
        130                 135                 140

Gly Thr Ser Thr Lys Thr Val Ile Arg Tyr Asn Gly Thr Val Thr Trp
145                 150                 155                 160

Thr Pro Pro Ala Asn Tyr Lys Ser Ser Cys Thr Ile Asp Val Thr Phe
                165                 170                 175

Phe Pro Phe Asp Leu Gln Asn Cys Ser Met Lys Phe Gly Ser Trp Thr
            180                 185                 190

Tyr Asp Gly Ser Gln Val Asp Ile Ile Leu Glu Asp Gln Asp Val Asp
            195                 200                 205

Lys Arg Asp Phe Phe Asp Asn Gly Glu Trp Glu Ile Val Ser Ala Thr
210                 215                 220

Gly Ser Lys Gly Asn Arg Thr Asp Ser Cys Cys Trp Tyr Pro Tyr Val
225                 230                 235                 240

Thr Tyr Ser Phe Val Ile Lys Arg Leu Pro Leu Phe Tyr Thr Leu Phe
                245                 250                 255

Leu Ile Ile Pro Cys Ile Gly Leu Ser Phe Leu Thr Val Leu Val Phe
            260                 265                 270

Tyr Leu Pro Ser Asn Glu Gly Glu Lys Ile Cys Leu Cys Thr Ser Val
            275                 280                 285

Leu Val Ser Leu Thr Val Phe Leu Leu Val Ile Glu Glu Ile Ile Pro
        290                 295                 300

Ser Ser Ser Lys Val Ile Pro Leu Ile Gly Glu Tyr Leu Val Phe Thr
```

```
                305                 310                 315                 320
Met Ile Phe Val Thr Leu Ser Ile Met Val Thr Val Phe Ala Ile Asn
                    325                 330                 335

Ile His His Arg Ser Ser Ser Thr His Asn Ala Met Ala Pro Leu Val
                340                 345                 350

Arg Lys Ile Phe Leu His Thr Leu Pro Lys Leu Leu Cys Met Arg Ser
            355                 360                 365

His Val Asp Arg Tyr Phe Thr Gln Lys Glu Glu Thr Glu Ser Gly Ser
        370                 375                 380

Gly Pro Lys Ser Ser Arg Asn Thr Leu Glu Ala Ala Leu Asn Ser Ile
385                 390                 395                 400

Arg Tyr Ile Thr Arg His Ile Met Lys Glu Asn Asp Val Arg Glu Val
                405                 410                 415

Val Glu Asp Trp Lys Phe Ile Ala Gln Val Leu Asp Arg Met Phe Leu
                420                 425                 430

Trp Thr Phe Leu Phe Val Ser Ile Val Gly Ser Leu Gly Leu Phe Val
            435                 440                 445

Pro Val Ile Tyr Lys Trp Ala Asn Ile Leu Ile Pro Val His Ile Gly
        450                 455                 460

Asn Ala Asn Lys
465

(2) INFORMATION FOR SEQ ID NO:9:

(i) SEQUENCE CHARACTERISTICS:
        (A) LENGTH: 1743 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 143..1627
        (D) OTHER INFORMATION: /product= "ALPHA-6 SUBUNIT"

(xi) SEQUENCE DESCRIPTION: SEQ ID NO:9:

CGGGTTTTGA TTTCTGAGAA GACACACACG GATTGCAGTG GGCTTCTGAT GATGTCAAGG      60

TTGGATGCAT GTGGCTGACT GATAGCTCTT TGTTTTCCAC AATCCTTTGC CTAGGAAAAA    120

GGAATCCAAG TGTGTTTTAA CC ATG CTG ACC AGC AAG GGG CAG GGA TTC CTT    172
                          Met Leu Thr Ser Lys Gly Gln Gly Phe Leu
                            1               5                  10

CAT GGG GGC TTG TGT CTC TGG CTG TGT GTG TTC ACA CCT TTC TTT AAA      220
His Gly Gly Leu Cys Leu Trp Leu Cys Val Phe Thr Pro Phe Phe Lys
                15                  20                  25

GGC TGT GTG GGC TGT GCA ACT GAG GAG AGG CTC TTC CAC AAA CTG TTT      268
Gly Cys Val Gly Cys Ala Thr Glu Glu Arg Leu Phe His Lys Leu Phe
            30                  35                  40

TCT CAT TAC AAC CAG TTC ATC AGG CCT GTG GAA AAC GTT TCC GAC CCT      316
Ser His Tyr Asn Gln Phe Ile Arg Pro Val Glu Asn Val Ser Asp Pro
        45                  50                  55

GTC ACG GTA CAC TTT GAA GTG GCC ATC ACC CAG CTG GCC AAC GTG GAT      364
Val Thr Val His Phe Glu Val Ala Ile Thr Gln Leu Ala Asn Val Asp
    60                  65                  70

GAA GTA AAC CAG ATC ATG GAA ACC AAT TTG TGG CTG CGT CAC ATC TGG      412
Glu Val Asn Gln Ile Met Glu Thr Asn Leu Trp Leu Arg His Ile Trp
75                  80                  85                  90

AAT GAT TAT AAA TTG CGC TGG GAT CCA ATG GAA TAT GAT GGC ATT GAG      460
```

```
                Asn Asp Tyr Lys Leu Arg Trp Asp Pro Met Glu Tyr Asp Gly Ile Glu
                                 95                 100                105

ACT CTT CGC GTT CCT GCA GAT AAG ATT TGG AAG CCC GAC ATT GTT CTC              508
Thr Leu Arg Val Pro Ala Asp Lys Ile Trp Lys Pro Asp Ile Val Leu
            110                 115                 120

TAT AAC AAT GCT GTT GGT GAC TTC CAA GTA GAA GGC AAA ACA AAA GCT              556
Tyr Asn Asn Ala Val Gly Asp Phe Gln Val Glu Gly Lys Thr Lys Ala
            125                 130                 135

CTT CTT AAA TAC AAT GGC ATG ATA ACC TGG ACT CCA CCA GCT ATT TTT              604
Leu Leu Lys Tyr Asn Gly Met Ile Thr Trp Thr Pro Pro Ala Ile Phe
        140                 145                 150

AAG AGT TCC TGC CCT ATG GAT ATC ACC TTT TTC CCT TTT GAT CAT CAA              652
Lys Ser Ser Cys Pro Met Asp Ile Thr Phe Phe Pro Phe Asp His Gln
155                 160                 165                 170

AAC TGT TCC CTA AAA TTT GGT TCC TGG ACG TAT GAC AAA GCT GAA ATT              700
Asn Cys Ser Leu Lys Phe Gly Ser Trp Thr Tyr Asp Lys Ala Glu Ile
                175                 180                 185

GAT CTT CTA ATC ATT GGA TCA AAA GTG GAT ATG AAT GAT TTT TGG GAA              748
Asp Leu Leu Ile Ile Gly Ser Lys Val Asp Met Asn Asp Phe Trp Glu
            190                 195                 200

AAC AGT GAA TGG GAA ATC ATT GAT GCC TCT GGC TAC AAA CAT GAC ATC              796
Asn Ser Glu Trp Glu Ile Ile Asp Ala Ser Gly Tyr Lys His Asp Ile
            205                 210                 215

AAA TAC AAC TGT TGT GAA GAG ATA TAC ACA GAT ATA ACC TAT TCT TTC              844
Lys Tyr Asn Cys Cys Glu Glu Ile Tyr Thr Asp Ile Thr Tyr Ser Phe
        220                 225                 230

TAC ATT AGA AGA TTG CCG ATG TTT TAC ACG ATT AAT CTG ATC ATC CCT              892
Tyr Ile Arg Arg Leu Pro Met Phe Tyr Thr Ile Asn Leu Ile Ile Pro
235                 240                 245                 250

TGT CTC TTT ATT TCA TTT CTA ACC GTG TTG GTC TTT TAC CTT CCT TCG              940
Cys Leu Phe Ile Ser Phe Leu Thr Val Leu Val Phe Tyr Leu Pro Ser
                255                 260                 265

GAC TGT GGT GAA AAA GTG ACG CTT TGT ATT TCA GTC CTG CTT TCT CTG              988
Asp Cys Gly Glu Lys Val Thr Leu Cys Ile Ser Val Leu Leu Ser Leu
            270                 275                 280

ACT GTG TTT TTG CTG GTC ATC ACA GAA ACC ATC CCA TCC ACA TCT CTG             1036
Thr Val Phe Leu Leu Val Ile Thr Glu Thr Ile Pro Ser Thr Ser Leu
            285                 290                 295

GTG GTC CCA CTG GTG GGT GAG TAC CTG CTG TTC ACC ATG ATC TTT GTC             1084
Val Val Pro Leu Val Gly Glu Tyr Leu Leu Phe Thr Met Ile Phe Val
        300                 305                 310

ACA CTG TCC ATC GTG GTG ACT GTG TTT GTG TTG AAC ATA CAC TAC CGC             1132
Thr Leu Ser Ile Val Val Thr Val Phe Val Leu Asn Ile His Tyr Arg
315                 320                 325                 330

ACC CCA ACC ACG CAC ACA ATG CCC AGG TGG GTG AAG ACA GTT TTC CTG             1180
Thr Pro Thr Thr His Thr Met Pro Arg Trp Val Lys Thr Val Phe Leu
                335                 340                 345

AAG CTG CTG CCC CAG GTC CTG CTG ATG AGG TGG CCT CTG GAC AAG ACA             1228
Lys Leu Leu Pro Gln Val Leu Leu Met Arg Trp Pro Leu Asp Lys Thr
            350                 355                 360

AGG GGC ACA GGC TCT GAT GCA GTG CCC AGA GGC TTG GCC AGG AGG CCT             1276
Arg Gly Thr Gly Ser Asp Ala Val Pro Arg Gly Leu Ala Arg Arg Pro
            365                 370                 375

GCC AAA GGC AAG CTT GCA AGC CAT GGG AAC CCC AGA CAT CTT AAA GAA             1324
Ala Lys Gly Lys Leu Ala Ser His Gly Glu Pro Arg His Leu Lys Glu
        380                 385                 390

TGC TTC CAT TGT CAC AAA TCA AAT GAG CTT GCC ACA AGC AAG AGA AGA             1372
Cys Phe His Cys His Lys Ser Asn Glu Leu Ala Thr Ser Lys Arg Arg
395                 400                 405                 410
```

```
TTA AGT CAT CAG CCA TTA CAG TGG GTG GTG GAA AAT TCG GAG CAC TCG      1420
Leu Ser His Gln Pro Leu Gln Trp Val Val Glu Asn Ser Glu His Ser
                415                 420                 425

CCT GAA GTT GAA GAT GTG ATT AAC AGT GTT CAG TTC ATA GCA GAA AAC      1468
Pro Glu Val Glu Asp Val Ile Asn Ser Val Gln Phe Ile Ala Glu Asn
            430                 435                 440

ATG AAG AGC CAC AAT GAA ACC AAG GAG GTA GAA GAT GAC TGG AAA TAC      1516
Met Lys Ser His Asn Glu Thr Lys Glu Val Glu Asp Asp Trp Lys Tyr
                445                 450                 455

GTG GCC ATG GTG GTG GAC AGA GTA TTT CTT TGG GTA TTT ATA ATT GTC      1564
Val Ala Met Val Val Asp Arg Val Phe Leu Trp Val Phe Ile Ile Val
        460                 465                 470

TGT GTA TTT GGA ACT GCA GGG CTA TTT CTA CAG CCA CTA CTT GGG AAC      1612
Cys Val Phe Gly Thr Ala Gly Leu Phe Leu Gln Pro Leu Leu Gly Asn
475                 480                 485                 490

ACA GGA AAA TCT TAAAATGTAT TTTCTTTTAT GTTCAGAAAT TTACAGACAC          1664
Thr Gly Lys Ser
            495

CATATTTGTT CTGCATTCCC TGCCACAAGG AAAGGAAAGC AAAGGCTTCC CACCCAAGTC    1724

CCCCATCTGC TAAAACCCG                                                 1743

(2) INFORMATION FOR SEQ ID NO:10:

(i) SEQUENCE CHARACTERISTICS:
        (A) LENGTH: 494 amino acids
        (B) TYPE: amino acid
        (D) TOPOLOGY: linear (ii) MOLECULE TYPE: protein (xi) SEQUENCE DESCRIPTION: SEQ ID NO:10:

Met Leu Thr Ser Lys Gly Gln Gly Phe Leu His Gly Gly Leu Cys Leu
  1               5                  10                  15

Trp Leu Cys Val Phe Thr Pro Phe Lys Gly Cys Val Gly Cys Ala
                 20                  25                  30

Thr Glu Glu Arg Leu Phe His Lys Leu Phe Ser His Tyr Asn Gln Phe
             35                  40                  45

Ile Arg Pro Val Glu Asn Val Ser Asp Pro Val Thr Val His Phe Glu
         50                  55                  60

Val Ala Ile Thr Gln Leu Ala Asn Val Asp Glu Val Asn Gln Ile Met
 65                  70                  75                  80

Glu Thr Asn Leu Trp Leu Arg His Ile Trp Asn Asp Tyr Lys Leu Arg
                 85                  90                  95

Trp Asp Pro Met Glu Tyr Asp Gly Ile Glu Thr Leu Arg Val Pro Ala
                100                 105                 110

Asp Lys Ile Trp Lys Pro Asp Ile Val Leu Tyr Asn Asn Ala Val Gly
            115                 120                 125

Asp Phe Gln Val Glu Gly Lys Thr Lys Ala Leu Leu Lys Tyr Asn Gly
        130                 135                 140

Met Ile Thr Trp Thr Pro Pro Ala Ile Phe Lys Ser Ser Cys Pro Met
145                 150                 155                 160

Asp Ile Thr Phe Phe Pro Phe Asp His Gln Asn Cys Ser Leu Lys Phe
                165                 170                 175

Gly Ser Trp Thr Tyr Asp Lys Ala Glu Ile Asp Leu Leu Ile Ile Gly
            180                 185                 190

Ser Lys Val Asp Met Asn Asp Phe Trp Glu Asn Ser Glu Trp Glu Ile
        195                 200                 205
```

```
Ile Asp Ala Ser Gly Tyr Lys His Asp Ile Lys Tyr Asn Cys Cys Glu
210                 215                 220

Glu Ile Tyr Thr Asp Ile Thr Tyr Ser Phe Tyr Ile Arg Arg Leu Pro
225                 230                 235                 240

Met Phe Tyr Thr Ile Asn Leu Ile Ile Pro Cys Leu Phe Ile Ser Phe
                245                 250                 255

Leu Thr Val Leu Val Phe Tyr Leu Pro Ser Asp Cys Gly Glu Lys Val
                260                 265                 270

Thr Leu Cys Ile Ser Val Leu Leu Ser Leu Thr Val Phe Leu Leu Val
        275                 280                 285

Ile Thr Glu Thr Ile Pro Ser Thr Ser Leu Val Val Pro Leu Val Gly
290                 295                 300

Glu Tyr Leu Leu Phe Thr Met Ile Phe Val Thr Leu Ser Ile Val Val
305                 310                 315                 320

Thr Val Phe Val Leu Asn Ile His Tyr Arg Thr Pro Thr Thr His Thr
                325                 330                 335

Met Pro Arg Trp Val Lys Thr Val Phe Leu Lys Leu Leu Pro Gln Val
                340                 345                 350

Leu Leu Met Arg Trp Pro Leu Asp Lys Thr Arg Gly Thr Gly Ser Asp
        355                 360                 365

Ala Val Pro Arg Gly Leu Ala Arg Arg Pro Ala Lys Gly Lys Leu Ala
370                 375                 380

Ser His Gly Glu Pro Arg His Leu Lys Glu Cys Phe His Cys His Lys
385                 390                 395                 400

Ser Asn Glu Leu Ala Thr Ser Lys Arg Arg Leu Ser His Gln Pro Leu
                405                 410                 415

Gln Trp Val Val Glu Asn Ser Glu His Ser Pro Glu Val Glu Asp Val
                420                 425                 430

Ile Asn Ser Val Gln Phe Ile Ala Glu Asn Met Lys Ser His Asn Glu
        435                 440                 445

Thr Lys Glu Val Glu Asp Asp Trp Lys Tyr Val Ala Met Val Val Asp
450                 455                 460

Arg Val Phe Leu Trp Val Phe Ile Ile Val Cys Val Phe Gly Thr Ala
465                 470                 475                 480

Gly Leu Phe Leu Gln Pro Leu Leu Gly Asn Thr Gly Lys Ser
                485                 490
```

(2) INFORMATION FOR SEQ ID NO:11:

(i) SEQUENCE CHARACTERISTICS:
        (A) LENGTH: 1876 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 73..1581
        (D) OTHER INFORMATION: /product= "ALPHA-7 SUBUNIT"

(xi) SEQUENCE DESCRIPTION: SEQ ID NO:11:

```
GGCCGCAGGC GCAGGCCCGG GCGACAGCCG AGACGTGGAG CGCGCCGGCT CGCTGCAGCT    60

CCGGGACTCA ACATGCGCTG CTCGCCGGGA GGCGTCTGGC TGGCGCTGGC CGCGTCGCTC   120

CTGCACGTGT CCCTGCAAGG CGAGTTCCAG AGGAAGCTTT ACAAGGAGCT GGTCAAGAAC   180

TACAATCCCT GGAGAGGCC CGTGGCCAAT GACTCGCAAC CACTCACCGT CTACTTCTCC   240
```

```
CTGAGCCTCC TGCAGATCAT GGACGTGGAT GAGAAGAACC AAGTTTTAAC CACCAACATT      300

TGGCTGCAAA TGTCTTGGAC AGATCACTAT TTACAGTGGA ATGTGTCAGA ATATCCAGGG      360

GTGAAGACTG TTCGTTTCCC AGATGGCCAG ATTTGGAAAC CAGACATTCT TCTCTATAAC      420

AGTGCTGATG AGCGCTTTGA CGCCACATTC CACACTAACG TGTTGGTGAA TTCTTCTGGG      480

CATTGCCAGT ACCTGCCTCC AGGCATATTC AAGAGTTCCT GCTACATCGA TGTACGCTGG      540

TTTCCCTTTG ATGTGCAGCA CTGCAAACTG AAGTTTGGGT CCTGGTCTTA CGGAGGCTGG      600

TCCTTGGATC TGCAGATGCA GGAGGCAGAT ATCAGTGGCT ATATCCCCAA TGGAGAATGG      660

GACCTAGTGG AATCCCCGG CAAGAGGAGT GAAAGGTTCT ATGAGTGCTG CAAAGAGCCC       720

TACCCCGATG TCACCTTCAC AGTGACCATG CGCCGCAGGA CGCTCTACTA TGGCCTCAAC      780

CTGCTGATCC CCTGTGTGCT CATCTCCGCC CTCGCCCTGC TGGTGTTCCT GCTTCCTGCA      840

GATTCCGGGG AGAAGATTTC CCTGGGGATA ACAGTCTTAC TCTCTCTTAC CGTCTTCATG      900

CTGCTCGTGG CTGAGATCAT GCCCGCAACA TCCGATTCGG TACCATTGAT AGCCCAGTAC      960

TTCGCCAGCA CCATGATCAT CGTGGGCCTC TCGGTGGTGG TGACGGTGAT CGTGCTGCAG     1020

TACCACCACC ACGACCCCGA CGGGGGCAAG ATGCCCAAGT GGACCAGAGT CATCCTTCTG     1080

AACTGGTGCG CGTGGTTCCT SCGAATGAAG AGGCCCGGGG AGGACAAGGT GCGCCCGGCC     1140

TGCCAGCACA AGCAGCGGCG CTGCAGCCTG GCCAGTGTGG AGATGAGCGC CGTGGCGCCG     1200

CCGCCCGCCA GCAACGGGAA CCTGCTGTAC ATCGGCTTCC GCGGCCTGGA CGGCGTGCAC     1260

TGTGTCCCGA CCCCCGACTC TGGGGTAGTG TGTGGCCGCA TGGCCTGCTC CCCCACGCAC     1320

GATGAGCACC TCCTGCACGG CGGGCAACCC CCCGAGGGGG ACCCGGACTT GGCCAAGATC     1380

CTGGAGGAGG TCCGCTACAT TGCCAATCGC TTCCGCTGCC AGGACGAAAG CGAGGCGGTC     1440

TGCAGCGAGT GGAAGTTCGC CGCCTGTGTG GTGGACCGCC TGTGCCTCAT GGCCTTCTCG     1500

GTCTTCACCA TCATCTGCAC CATCGGCATC CTGATGTCGG CTCCCAACTT CGTGGAGGCC     1560

GTGTCCAAAG ACTTTGCGTA CCACGCCTG GTTCTGTACA TGTGGAAAAC TCACAGATGG      1620

GCAAGGCCTT TGGCTTGGCG AGATTTGGGG GTGCTAATCC AGGACAGCAT TACACGCCAC     1680

AACTCCAGTG TTCCCTTCTG GCTGTCAGTC GTGTTGCTTA CGGTTTCTTT GTTACTTTAG     1740

GTAGTAGAAT CTCAGCACTT TGTTTCATAT TCTCAGATGG GCTGATAGAT ATCCTTGGCA     1800

CATCCGTACC ATCGGTCAGC AGGGCCACTG AGTAGTCATT TGCCCATTA GCCCACTGCC      1860

TGGAAAGCCC TTCGGA                                                     1876

(2) INFORMATION FOR SEQ ID NO:12:

(i) SEQUENCE CHARACTERISTICS:
        (A) LENGTH: 502 amino acids
        (B) TYPE: amino acid
        (D) TOPOLOGY: unknown (ii) MOLECULE TYPE: protein (xi) SEQUENCE DESCRIPTION: SEQ ID NO:12:

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
```

```
            50                  55                  60
Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
            115                 120                 125

Asn Val Leu Val Asn Ser Ser Gly His Cys Gln Tyr Leu Pro Pro Gly
            130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
                180                 185                 190

Asn Gly Glu Trp Asp Leu Val Gly Ile Pro Gly Lys Arg Ser Glu Arg
            195                 200                 205

Phe Tyr Glu Cys Cys Lys Glu Pro Tyr Pro Asp Val Thr Phe Thr Val
            210                 215                 220

Thr Met Arg Arg Arg Thr Leu Tyr Tyr Gly Leu Asn Leu Leu Ile Pro
225                 230                 235                 240

Cys Val Leu Ile Ser Ala Leu Ala Leu Leu Val Phe Leu Leu Pro Ala
                245                 250                 255

Asp Ser Gly Glu Lys Ile Ser Leu Gly Ile Thr Val Leu Leu Ser Leu
                260                 265                 270

Thr Val Phe Met Leu Leu Val Ala Glu Ile Met Pro Ala Thr Ser Asp
            275                 280                 285

Ser Val Pro Leu Ile Ala Gln Tyr Phe Ala Ser Thr Met Ile Ile Val
            290                 295                 300

Gly Leu Ser Val Val Val Thr Val Ile Val Leu Gln Tyr His His His
305                 310                 315                 320

Asp Pro Asp Gly Gly Lys Met Pro Lys Trp Thr Arg Val Ile Leu Leu
                325                 330                 335

Asn Trp Cys Ala Trp Phe Leu Arg Met Lys Arg Pro Gly Glu Asp Lys
                340                 345                 350

Val Arg Pro Ala Cys Gln His Lys Gln Arg Arg Cys Ser Leu Ala Ser
            355                 360                 365

Val Glu Met Ser Ala Val Ala Pro Pro Ala Ser Asn Gly Asn Leu
            370                 375                 380

Leu Tyr Ile Gly Phe Arg Gly Leu Asp Gly Val His Cys Val Pro Thr
385                 390                 395                 400

Pro Asp Ser Gly Val Val Cys Gly Arg Met Ala Cys Ser Pro Thr His
                405                 410                 415

Asp Glu His Leu Leu His Gly Gly Gln Pro Pro Glu Gly Asp Pro Asp
                420                 425                 430

Leu Ala Lys Ile Leu Glu Glu Val Arg Tyr Ile Ala Asn Arg Phe Arg
            435                 440                 445

Cys Gln Asp Glu Ser Glu Ala Val Cys Ser Glu Trp Lys Phe Ala Ala
            450                 455                 460

Cys Val Val Asp Arg Leu Cys Leu Met Ala Phe Ser Val Phe Thr Ile
465                 470                 475                 480
```

```
Ile Cys Thr Ile Gly Ile Leu Met Ser Ala Pro Asn Phe Val Glu Ala
            485                 490                 495

Val Ser Lys Asp Phe Ala
            500

(2) INFORMATION FOR SEQ ID NO:13:

(i) SEQUENCE CHARACTERISTICS:
        (A) LENGTH: 2448 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 265..1773
        (D) OTHER INFORMATION: /product= "BETA-2 SUBUNIT"

(xi) SEQUENCE DESCRIPTION: SEQ ID NO:13:

CTCCTCCCCC TCACCGTCCC AATTGTATTC CCTGGAAGAG CAGCCGGAAA AGCCTCCGCC         60

TGCTCATACC AGGATAGGCA AGAAGCTGGT TTCTCCTCGC AGCCGGCTCC CTGAGGCCCA        120

GGAACCACCG CGGCGGCCGG CACCACCTGG ACCCAGCTCC AGGCGGGCGC GGCTTCAGCA        180

CCACGGACAG CGCCCCACCC GCGGCCCTCC CCCCGGCGGC GCGCTCCAGC CGGTGTAGGC        240

GAGGCAGCGA GCTATGCCCG CGGC ATG GCC CGG CGC TGC GGC CCC GTG GCG          291
                           Met Ala Arg Arg Cys Gly Pro Val Ala
                             1               5

CTG CTC CTT GGC TTC GGC CTC CTC CGG CTG TGC TCA GGG GTG TGG GGT         339
Leu Leu Leu Gly Phe Gly Leu Leu Arg Leu Cys Ser Gly Val Trp Gly
 10              15                  20                  25

ACG GAT ACA GAG GAG CGG CTG GTG GAG CAT CTC CTG GAT CCT TCC CGC         387
Thr Asp Thr Glu Glu Arg Leu Val Glu His Leu Leu Asp Pro Ser Arg
             30                  35                  40

TAC AAC AAG CTT ATC CGC CCA GCC ACC AAT GGC TCT GAG CTG GTG ACA         435
Tyr Asn Lys Leu Ile Arg Pro Ala Thr Asn Gly Ser Glu Leu Val Thr
         45                  50                  55

GTA CAG CTT ATG GTG TCA CTG GCC CAG CTC ATC AGT GTG CAT GAG CGG         483
Val Gln Leu Met Val Ser Leu Ala Gln Leu Ile Ser Val His Glu Arg
     60                  65                  70

GAG CAG ATC ATG ACC ACC AAT GTC TGG CTG ACC CAG GAG TGG GAA GAT         531
Glu Gln Ile Met Thr Thr Asn Val Trp Leu Thr Gln Glu Trp Glu Asp
 75                  80                  85

TAT CGC CTC ACC TGG AAG CCT GAA GAG TTT GAC AAC ATG AAG AAA GTT         579
Tyr Arg Leu Thr Trp Lys Pro Glu Glu Phe Asp Asn Met Lys Lys Val
 90                  95                 100                 105

CGG CTC CCT TCC AAA CAC ATC TGG CTC CCA GAT GTG GTC CTG TAC AAC         627
Arg Leu Pro Ser Lys His Ile Trp Leu Pro Asp Val Val Leu Tyr Asn
             110                 115                 120

AAT GCT GAC GGC ATG TAC GAG GTG TCC TTC TAT TCC AAT GCC GTG GTC         675
Asn Ala Asp Gly Met Tyr Glu Val Ser Phe Tyr Ser Asn Ala Val Val
             125                 130                 135

TCC TAT GAT GGC AGC ATC TTC TGG CTG CCG CCT GCC ATC TAC AAG AGC         723
Ser Tyr Asp Gly Ser Ile Phe Trp Leu Pro Pro Ala Ile Tyr Lys Ser
         140                 145                 150

GCA TGC AAG ATT GAA GTA AAG CAC TTC CCA TTT GAC CAG CAG AAC TGC         771
Ala Cys Lys Ile Glu Val Lys His Phe Pro Phe Asp Gln Gln Asn Cys
 155                 160                 165

ACC ATG AAG TTC CGT TCG TGG ACC TAC GAC CGC ACA GAG ATC GAC TTG         819
Thr Met Lys Phe Arg Ser Trp Thr Tyr Asp Arg Thr Glu Ile Asp Leu
```

-continued

```
         170                 175                 180                 185
GTG CTG AAG AGT GAG GTG GCC AGC CTG GAC GAC TTC ACA CCT AGT GGT          867
Val Leu Lys Ser Glu Val Ala Ser Leu Asp Asp Phe Thr Pro Ser Gly
                    190                 195                 200

GAG TGG GAC ATC GTG GCG CTG CCG GGC CGG CGC AAC GAG AAC CCC GAC          915
Glu Trp Asp Ile Val Ala Leu Pro Gly Arg Arg Asn Glu Asn Pro Asp
                205                 210                 215

GAC TCT ACG TAC GTG GAC ATC ACG TAT GAC TTC ATC ATT CGC CGC AAG          963
Asp Ser Thr Tyr Val Asp Ile Thr Tyr Asp Phe Ile Ile Arg Arg Lys
            220                 225                 230

CCG CTC TTC TAC ACC ATC AAC CTC ATC ATC CCC TGT GTG CTC ATC ACC         1011
Pro Leu Phe Tyr Thr Ile Asn Leu Ile Ile Pro Cys Val Leu Ile Thr
        235                 240                 245

TCG CTA GCC ATC CTT GTC TTC TAC CTG CCA TCC GAC TGT GGC GAG AAG         1059
Ser Leu Ala Ile Leu Val Phe Tyr Leu Pro Ser Asp Cys Gly Glu Lys
250                 255                 260                 265

ATG ACG TTG TGC ATC TCA GTG CTG CTG GCG CTC ACG GTC TTC CTG CTG         1107
Met Thr Leu Cys Ile Ser Val Leu Leu Ala Leu Thr Val Phe Leu Leu
                270                 275                 280

CTC ATC TCC AAG ATC GTG CCT CCC ACC TCC CTC GAC GTG CCG CTC GTC         1155
Leu Ile Ser Lys Ile Val Pro Pro Thr Ser Leu Asp Val Pro Leu Val
                285                 290                 295

GGC AAG TAC CTC ATG TTC ACC ATG GTG CTT GTC ACC TTC TCC ATC GTC         1203
Gly Lys Tyr Leu Met Phe Thr Met Val Leu Val Thr Phe Ser Ile Val
            300                 305                 310

ACC AGC GTG TGC GTG CTC AAC GTG CAC CAC CGC TCG CCC ACC ACG CAC         1251
Thr Ser Val Cys Val Leu Asn Val His His Arg Ser Pro Thr Thr His
        315                 320                 325

ACC ATG GCG CCC TGG GTG AAG GTC GTC TTC CTG GAG AAG CTG CCC GCG         1299
Thr Met Ala Pro Trp Val Lys Val Val Phe Leu Glu Lys Leu Pro Ala
330                 335                 340                 345

CTG CTC TTC ATG CAG CAG CCA CGC CAT CAT TGC GCC CGT CAG CGC CTG         1347
Leu Leu Phe Met Gln Gln Pro Arg His His Cys Ala Arg Gln Arg Leu
                350                 355                 360

CGC CTG CGG CGA CGC CAG CGT GAG CGC GAG GGC GCT GGA GCC CTC TTC         1395
Arg Leu Arg Arg Arg Gln Arg Glu Arg Glu Gly Ala Gly Ala Leu Phe
                365                 370                 375

TTC CGC GAA GCC CCA GGG GCC GAC TCC TGC ACG TGC TTC GTC AAC CGC         1443
Phe Arg Glu Ala Pro Gly Ala Asp Ser Cys Thr Cys Phe Val Asn Arg
            380                 385                 390

GCG TCG GTG CAG GGG TTG GCC GGG GCC TTC GGG GCT GAG CCT GCA CCA         1491
Ala Ser Val Gln Gly Leu Ala Gly Ala Phe Gly Ala Glu Pro Ala Pro
        395                 400                 405

GTG GCG GGC CCC GGG CGC TCA GGG GAG CCG TGT GGC TGT GGC CTC CGG         1539
Val Ala Gly Pro Gly Arg Ser Gly Glu Pro Cys Gly Cys Gly Leu Arg
410                 415                 420                 425

GAG GCG GTG GAC GGC GTG CGC TTC ATC GCA GAC CAC ATG CGG AGC GAG         1587
Glu Ala Val Asp Gly Val Arg Phe Ile Ala Asp His Met Arg Ser Glu
                430                 435                 440

GAC GAT GAC CAG AGC GTG AGT GAG GAC TGG AAG TAC GTC GCC ATG GTG         1635
Asp Asp Asp Gln Ser Val Ser Glu Asp Trp Lys Tyr Val Ala Met Val
                445                 450                 455

ATC GAC CGC CTC TTC CTC TGG ATC TTT GTC TTT GTC TGT GTC TTT GGC         1683
Ile Asp Arg Leu Phe Leu Trp Ile Phe Val Phe Val Cys Val Phe Gly
            460                 465                 470

ACC ATC GGC ATG TTC CTG CAG CCT CTC TTC CAG AAC TAC ACC ACC ACC         1731
Thr Ile Gly Met Phe Leu Gln Pro Leu Phe Gln Asn Tyr Thr Thr Thr
        475                 480                 485

ACC TTC CTC CAC TCA GAC CAC TCA GCC CCC AGC TCC AAG TGAGGCCCTT         1780
```

```
Thr Phe Leu His Ser Asp His Ser Ala Pro Ser Ser Lys
490                 495                 500

CCTCATCTCC ATGCTCTTTC ACCCTGCCAC CCTCTGCTGC ACAGTAGTGT TGGGTGGAGG    1840

ATGGACGAGT GAGCTACCAG GAAGAGGGGC GCTGCCCCCA CAGATCCATC CTTTTGCTTC    1900

ATCTGGAGTC CCTCCTCCCC CACGCCTCCA TCCACACACA GCAGCTCCAA CCTGGAGGCT    1960

GGACCAACTG CTTTGTTTTG GCTGCTCTCC ATCTCTTGTA CCAGCCCAGG CAATAGTGTT    2020

GAGGAGGGGA GCAAGGCTGC TAAGTGGAAG ACAGAGATGG CAGAGCCATC CACCCTGAGG    2080

AGTGACGGGC AAGGGGCCAG GAAGGGGACA GGATTGTCTG CTGCCTCCAA GTCATGGGAG    2140

AAGAGGGGTA TAGGACAAGG GGTGGAAGGG CAGGAGCTCA CACCGCACCG GGCTGGCCTG    2200

ACACAATGGT AGCTCTGAAG GGAGGGGAAG AGAGAGGCCT GGGTGTGACC TGACACCTGC    2260

CGCTGCTTGA GTGGACAGCA GCTGGACTGG GTGGGCCCCA CAGTGGTCAG CGATTCCTGC    2320

CAAGTAGGGT TTAGCCGGGC CCCATGGTCA CAGACCCCTG GGGGAGGCTT CCAGCTCAGT    2380

CCCACAGCCC CTTGCTTCTA AGGGATCCAG AGACCTGCTC CAGATCCTCT TTCCCCACTG    2440

AAGAATTC                                                            2448

(2) INFORMATION FOR SEQ ID NO:14:

(i) SEQUENCE CHARACTERISTICS:
        (A) LENGTH: 502 amino acids
        (B) TYPE: amino acid
        (D) TOPOLOGY: linear (ii) MOLECULE TYPE: protein (xi) SEQUENCE DESCRIPTION: SEQ ID NO:14:

Met Ala Arg Arg Cys Gly Pro Val Ala Leu Leu Gly Phe Gly Leu
1               5                   10                  15

Leu Arg Leu Cys Ser Gly Val Trp Gly Thr Asp Thr Glu Glu Arg Leu
            20                  25                  30

Val Glu His Leu Leu Asp Pro Ser Arg Tyr Asn Lys Leu Ile Arg Pro
        35                  40                  45

Ala Thr Asn Gly Ser Glu Leu Val Thr Val Gln Leu Met Val Ser Leu
    50                  55                  60

Ala Gln Leu Ile Ser Val His Glu Arg Glu Gln Ile Met Thr Thr Asn
65                  70                  75                  80

Val Trp Leu Thr Gln Glu Trp Glu Asp Tyr Arg Leu Thr Trp Lys Pro
                85                  90                  95

Glu Glu Phe Asp Asn Met Lys Lys Val Arg Leu Pro Ser Lys His Ile
                100                 105                 110

Trp Leu Pro Asp Val Val Leu Tyr Asn Asn Ala Asp Gly Met Tyr Glu
        115                 120                 125

Val Ser Phe Tyr Ser Asn Ala Val Val Ser Tyr Asp Gly Ser Ile Phe
    130                 135                 140

Trp Leu Pro Pro Ala Ile Tyr Lys Ser Ala Cys Lys Ile Glu Val Lys
145                 150                 155                 160

His Phe Pro Phe Asp Gln Gln Asn Cys Thr Met Lys Phe Arg Ser Trp
                165                 170                 175

Thr Tyr Asp Arg Thr Glu Ile Asp Leu Val Leu Lys Ser Glu Val Ala
                180                 185                 190

Ser Leu Asp Asp Phe Thr Pro Ser Gly Glu Trp Asp Ile Val Ala Leu
        195                 200                 205

Pro Gly Arg Arg Asn Glu Asn Pro Asp Asp Ser Thr Tyr Val Asp Ile
```

-continued

```
            210                 215                 220
Thr Tyr Asp Phe Ile Ile Arg Arg Lys Pro Leu Phe Tyr Thr Ile Asn
225                 230                 235                 240

Leu Ile Ile Pro Cys Val Leu Ile Thr Ser Leu Ala Ile Leu Val Phe
                245                 250                 255

Tyr Leu Pro Ser Asp Cys Gly Glu Lys Met Thr Leu Cys Ile Ser Val
                260                 265                 270

Leu Leu Ala Leu Thr Val Phe Leu Leu Ile Ser Lys Ile Val Pro
                275                 280                 285

Pro Thr Ser Leu Asp Val Pro Leu Val Gly Lys Tyr Leu Met Phe Thr
                290                 295                 300

Met Val Leu Val Thr Phe Ser Ile Val Thr Ser Val Cys Val Leu Asn
305                 310                 315                 320

Val His His Arg Ser Pro Thr Thr His Thr Met Ala Pro Trp Val Lys
                325                 330                 335

Val Val Phe Leu Glu Lys Leu Pro Ala Leu Leu Phe Met Gln Gln Pro
                340                 345                 350

Arg His His Cys Ala Arg Gln Arg Leu Arg Leu Arg Arg Gln Arg
                355                 360                 365

Glu Arg Glu Gly Ala Gly Ala Leu Phe Phe Arg Glu Ala Pro Gly Ala
370                 375                 380

Asp Ser Cys Thr Cys Phe Val Asn Arg Ala Ser Val Gln Gly Leu Ala
385                 390                 395                 400

Gly Ala Phe Gly Ala Glu Pro Ala Pro Val Ala Gly Pro Gly Arg Ser
                405                 410                 415

Gly Glu Pro Cys Gly Cys Gly Leu Arg Glu Ala Val Asp Gly Val Arg
                420                 425                 430

Phe Ile Ala Asp His Met Arg Ser Glu Asp Asp Gln Ser Val Ser
                435                 440                 445

Glu Asp Trp Lys Tyr Val Ala Met Val Ile Asp Arg Leu Phe Leu Trp
450                 455                 460

Ile Phe Val Phe Val Cys Val Phe Gly Thr Ile Gly Met Phe Leu Gln
465                 470                 475                 480

Pro Leu Phe Gln Asn Tyr Thr Thr Thr Thr Phe Leu His Ser Asp His
                485                 490                 495

Ser Ala Pro Ser Ser Lys
                500
```

(2) INFORMATION FOR SEQ ID NO:15:

(i) SEQUENCE CHARACTERISTICS:
        (A) LENGTH: 1927 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 98..1474
        (D) OTHER INFORMATION: /product= "BETA-3 SUBUNIT"

(xi) SEQUENCE DESCRIPTION: SEQ ID NO:15:

```
TCGGAACCCC TGTATTTTCT TTTCAAAACC CCCTTTTCCA GTGGAAATGC TCTGTTGTTA      60

AAAAGGAAGA AACTGTCTTT CTGAAACTGA CATCACG ATG CTC CCA GAT TTT ATG      115
                                        Met Leu Pro Asp Phe Met
                                         1               5
```

-continued

```
CTG GTT CTC ATC GTC CTT GGC ATC CCT TCC TCA GCC ACC ACA GGT TTC      163
Leu Val Leu Ile Val Leu Gly Ile Pro Ser Ser Ala Thr Thr Gly Phe
            10                  15                  20

AAC TCA ATC GCC GAA AAT GAA GAT GCC CTC CTC AGA CAT TTG TTC CAA      211
Asn Ser Ile Ala Glu Asn Glu Asp Ala Leu Leu Arg His Leu Phe Gln
        25                  30                  35

GGT TAT CAG AAA TGG GTC CGC CCT GTA TTA CAT TCT AAT GAC ACC ATA      259
Gly Tyr Gln Lys Trp Val Arg Pro Val Leu His Ser Asn Asp Thr Ile
    40                  45                  50

AAA GTA TAT TTT GGA TTG AAA ATA TCC CAG CTT GTA GAT GTG GAT GAA      307
Lys Val Tyr Phe Gly Leu Lys Ile Ser Gln Leu Val Asp Val Asp Glu
55                  60                  65                  70

AAG AAT CAG CTG ATG ACA ACC AAT GTG TGG CTC AAA CAG GAA TGG ACA      355
Lys Asn Gln Leu Met Thr Thr Asn Val Trp Leu Lys Gln Glu Trp Thr
                75                  80                  85

GAC CAC AAG TTA CGC TGG AAT CCT GAT GAT TAT GGT GGG ATC CAT TCC      403
Asp His Lys Leu Arg Trp Asn Pro Asp Asp Tyr Gly Gly Ile His Ser
            90                  95                 100

ATT AAA GTT CCA TCA GAA TCT CTG TGG CTT CCT GAC ATA GTT CTC TTT      451
Ile Lys Val Pro Ser Glu Ser Leu Trp Leu Pro Asp Ile Val Leu Phe
        105                 110                 115

GAA AAT GCT GAC GGC CGC TTC GAA GGC TCC CTG ATG ACC AAG GTC ATC      499
Glu Asn Ala Asp Gly Arg Phe Glu Gly Ser Leu Met Thr Lys Val Ile
    120                 125                 130

GTG AAA TCA AAC GGA ACT GTT GTC TGG ACC CCT CCC GCC AGC TAC AAA      547
Val Lys Ser Asn Gly Thr Val Val Trp Thr Pro Pro Ala Ser Tyr Lys
135                 140                 145                 150

AGC TCC TGC ACC ATG GAC GTC ACG TTT TTC CCG TTC GAC CGA CAG AAC      595
Ser Ser Cys Thr Met Asp Val Thr Phe Phe Pro Phe Asp Arg Gln Asn
                155                 160                 165

TGC TCC ATG AAG TTT GGA TCC TGG ACT TAT GAT GGC ACC ATG GTT GAC      643
Cys Ser Met Lys Phe Gly Ser Trp Thr Tyr Asp Gly Thr Met Val Asp
            170                 175                 180

CTC ATT TTG ATC AAT GAA AAT GTC GAC AGA AAA GAC TTC TTC GAT AAC      691
Leu Ile Leu Ile Asn Glu Asn Val Asp Arg Lys Asp Phe Phe Asp Asn
        185                 190                 195

GGA GAA TGG GAA ATA CTG AAT GCA AAG GGG ATG AAG GGG AAC AGA AGG      739
Gly Glu Trp Glu Ile Leu Asn Ala Lys Gly Met Lys Gly Asn Arg Arg
    200                 205                 210

GAC GGC GTG TAC TCC TAT CCC TTT ATC ACG TAT TCC TTC GTC CTG AGA      787
Asp Gly Val Tyr Ser Tyr Pro Phe Ile Thr Tyr Ser Phe Val Leu Arg
215                 220                 225                 230

CGC CTG CCT TTA TTC TAT ACC CTC TTT CTC ATC ATC CCC TGC CTG GGG      835
Arg Leu Pro Leu Phe Tyr Thr Leu Phe Leu Ile Ile Pro Cys Leu Gly
                235                 240                 245

CTG TCT TTC CTA ACA GTT CTT GTG TTC TAT TTA CCT TCG GAT GAA GGA      883
Leu Ser Phe Leu Thr Val Leu Val Phe Tyr Leu Pro Ser Asp Glu Gly
            250                 255                 260

GAA AAA CTT TCA TTA TCC ACA TCG GTC TTG GTT TCT CTG ACA GTT TTC      931
Glu Lys Leu Ser Leu Ser Thr Ser Val Leu Val Ser Leu Thr Val Phe
        265                 270                 275

CTT TTA GTG ATT GAA GAA ATC ATC CCA TCG TCT TCC AAA GTC ATT CCT      979
Leu Leu Val Ile Glu Glu Ile Ile Pro Ser Ser Ser Lys Val Ile Pro
    280                 285                 290

CTC ATT GGA GAG TAC CTG CTG TTC ATC ATG ATT TTT GTG ACC CTG TCC     1027
Leu Ile Gly Glu Tyr Leu Leu Phe Ile Met Ile Phe Val Thr Leu Ser
295                 300                 305                 310

ATC ATT GTT ACC GTG TTT GTC ATT AAC GTT CAC CAC AGA TCT TCT TCC     1075
Ile Ile Val Thr Val Phe Val Ile Asn Val His His Arg Ser Ser Ser
```

-continued

```
                    315                 320                 325
ACG TAC CAC CCC ATG GCC CCC TGG GTT AAG AGG CTC TTT CTG CAG AAA     1123
Thr Tyr His Pro Met Ala Pro Trp Val Lys Arg Leu Phe Leu Gln Lys
                330                 335                 340

CTT CCA AAA TTA CTT TGC ATG AAA GAT CAT GTG GAT CGC TAC TCA TCC     1171
Leu Pro Lys Leu Leu Cys Met Lys Asp His Val Asp Arg Tyr Ser Ser
            345                 350                 355

CCA GAG AAA GAG GAG AGT CAA CCA GTA GTG AAA GGC AAA GTC CTC GAA     1219
Pro Glu Lys Glu Glu Ser Gln Pro Val Val Lys Gly Lys Val Leu Glu
    360                 365                 370

AAA AAG AAA CAG AAA CAG CTT AGT GAT GGA GAA AAA GTT CTA GTT GCT     1267
Lys Lys Lys Gln Lys Gln Leu Ser Asp Gly Glu Lys Val Leu Val Ala
375                 380                 385                 390

TTT TTG GAA AAA GCT GCT GAT TCC ATT AGA TAC ATT TCC AGA CAT GTG     1315
Phe Leu Glu Lys Ala Ala Asp Ser Ile Arg Tyr Ile Ser Arg His Val
                395                 400                 405

AAG AAA GAA CAT TTT ATC AGC CAG GTA GTA CAA GAC TGG AAA TTT GTA     1363
Lys Lys Glu His Phe Ile Ser Gln Val Val Gln Asp Trp Lys Phe Val
            410                 415                 420

GCT CAA GTT CTT GAC CGA ATC TTC CTG TGG CTC TTT CTG ATA GTG TCA     1411
Ala Gln Val Leu Asp Arg Ile Phe Leu Trp Leu Phe Leu Ile Val Ser
    425                 430                 435

GCA ACA GGC TCG GTT CTG ATT TTT ACC CCT GCT TTG AAG ATG TGG CTA     1459
Ala Thr Gly Ser Val Leu Ile Phe Thr Pro Ala Leu Lys Met Trp Leu
440                 445                 450

CAT AGT TAC CAT TAGGAATTTC AAAAGACATA AGTACTAAAT TACACCTTAG          1511
His Ser Tyr His
455

ACCTGACATC TGGCTATCAC ACAGACAGAA TCCAAATGCA TGTGCTTGTT CTACGAACCC   1571

CGAATGCGTT GTCTTTGTGG AAATGGAACA TCTCCTCATG GGAGAAACTC TGGTAAATGT   1631

GCTCATTTGT GGTTGCCATG AGAGTGAGCT GCTTTTAAAG AAAGTGGAGC CTCCTCAGAC   1691

CCCTGCCTTG GCTTTCCCAG ACATTCAGGG AGGGATCATA GGTCCAGGCT TGAGCTCACA   1751

TGTGGCCAGA GTGCACAAAA AGCTGTTGCT ACTTGGTGGA GGAACACCTC CTAGAAGCAG   1811

CAGGCCTCGG TGGTGGGGGA GGGGGGATTC ACCTGGAATT AAGGAAGTCT CGGTGTCGAG   1871

CTATCTGTGT GGGCAGAGCC TGGATCTCCC ACCCTGCACT GGCCTCCTTG GTGCCG       1927
```

(2) INFORMATION FOR SEQ ID NO:16:

(i) SEQUENCE CHARACTERISTICS:
        (A) LENGTH: 458 amino acids
        (B) TYPE: amino acid
        (D) TOPOLOGY: linear (ii) MOLECULE TYPE: protein (xi) SEQUENCE DESCRIPTION: SEQ ID NO:16:

```
Met Leu Pro Asp Phe Met Leu Val Leu Ile Val Leu Gly Ile Pro Ser
1               5                   10                  15

Ser Ala Thr Thr Gly Phe Asn Ser Ile Ala Glu Asn Glu Asp Ala Leu
            20                  25                  30

Leu Arg His Leu Phe Gln Gly Tyr Gln Lys Trp Val Arg Pro Val Leu
        35                  40                  45

His Ser Asn Asp Thr Ile Lys Val Tyr Phe Gly Leu Lys Ile Ser Gln
    50                  55                  60

Leu Val Asp Val Asp Glu Lys Asn Gln Leu Met Thr Thr Asn Val Trp
65                  70                  75                  80
```

```
Leu Lys Gln Glu Trp Thr Asp His Lys Leu Arg Trp Asn Pro Asp Asp
                85                  90                  95

Tyr Gly Gly Ile His Ser Ile Lys Val Pro Ser Glu Ser Leu Trp Leu
                100                 105                 110

Pro Asp Ile Val Leu Phe Glu Asn Ala Asp Gly Arg Phe Glu Gly Ser
                115                 120                 125

Leu Met Thr Lys Val Ile Val Lys Ser Asn Gly Thr Val Val Trp Thr
    130                 135                 140

Pro Pro Ala Ser Tyr Lys Ser Ser Cys Thr Met Asp Val Thr Phe Phe
145                 150                 155                 160

Pro Phe Asp Arg Gln Asn Cys Ser Met Lys Phe Gly Ser Trp Thr Tyr
                165                 170                 175

Asp Gly Thr Met Val Asp Leu Ile Leu Ile Asn Glu Asn Val Asp Arg
                180                 185                 190

Lys Asp Phe Phe Asp Asn Gly Glu Trp Glu Ile Leu Asn Ala Lys Gly
                195                 200                 205

Met Lys Gly Asn Arg Arg Asp Gly Val Tyr Ser Tyr Pro Phe Ile Thr
    210                 215                 220

Tyr Ser Phe Val Leu Arg Arg Leu Pro Leu Phe Tyr Thr Leu Phe Leu
225                 230                 235                 240

Ile Ile Pro Cys Leu Gly Leu Ser Phe Leu Thr Val Leu Val Phe Tyr
                245                 250                 255

Leu Pro Ser Asp Glu Gly Glu Lys Leu Ser Leu Ser Thr Ser Val Leu
                260                 265                 270

Val Ser Leu Thr Val Phe Leu Leu Val Ile Glu Glu Ile Ile Pro Ser
                275                 280                 285

Ser Ser Lys Val Ile Pro Leu Ile Gly Glu Tyr Leu Leu Phe Ile Met
    290                 295                 300

Ile Phe Val Thr Leu Ser Ile Ile Val Thr Val Phe Val Ile Asn Val
305                 310                 315                 320

His His Arg Ser Ser Ser Thr Tyr His Pro Met Ala Pro Trp Val Lys
                325                 330                 335

Arg Leu Phe Leu Gln Lys Leu Pro Lys Leu Leu Cys Met Lys Asp His
                340                 345                 350

Val Asp Arg Tyr Ser Ser Pro Glu Lys Glu Ser Gln Pro Val Val
                355                 360                 365

Lys Gly Lys Val Leu Glu Lys Lys Gln Lys Gln Leu Ser Asp Gly
    370                 375                 380

Glu Lys Val Leu Val Ala Phe Leu Glu Lys Ala Ala Asp Ser Ile Arg
385                 390                 395                 400

Tyr Ile Ser Arg His Val Lys Lys Glu His Phe Ile Ser Gln Val Val
                405                 410                 415

Gln Asp Trp Lys Phe Val Ala Gln Val Leu Asp Arg Ile Phe Leu Trp
                420                 425                 430

Leu Phe Leu Ile Val Ser Ala Thr Gly Ser Val Leu Ile Phe Thr Pro
                435                 440                 445

Ala Leu Lys Met Trp Leu His Ser Tyr His
450                 455

(2) INFORMATION FOR SEQ ID NO:17:

(i) SEQUENCE CHARACTERISTICS:
        (A) LENGTH: 1915 base pairs
        (B) TYPE: nucleic acid
        (C) STRANDEDNESS: both
```

-continued

```
        (D) TOPOLOGY: both (ii) MOLECULE TYPE: cDNA (ix) FEATURE:
        (A) NAME/KEY: CDS
        (B) LOCATION: 87..1583
        (D) OTHER INFORMATION: /product= "BETA-4 SUBUNIT"

(xi) SEQUENCE DESCRIPTION: SEQ ID NO:17:

CCGGCGCTCA CTCGACCGCG CGGCTCACGG GTGCCCTGTG ACCCCACAGC GGAGCTCGCG      60
GCGGCTGCCA CCCGGCCCCG CCGGCCATGA GGCGCGCGCC TTCCCTGGTC CTTTTCTTCC     120
TGGTCGCCCT TTGCGGGCGC GGGAACTGCC GCGTGGCCAA TGCGGAGGAA AAGCTGATGG     180
ACGACCTTCT GAACAAAACC CGTTACAATA ACCTGATCCG CCCAGCCACC AGCTCCTCAC     240
AGCTCATCTC CATCAAGCTG CAGCTCTCCC TGGCCCAGCT TATCAGCGTG AATGAGCGAG     300
AGCAGATCAT GACCACCAAT GTCTGGCTGA ACAGGAATG GACTGATTAC CGCCTGACCT      360
GGAACAGCTC CCGCTACGAG GGTGTGAACA TCCTGAGGAT CCCTGCAAAG CGCATCTGGT     420
TGCCTGACAT CGTGCTTTAC AACAACGCCG ACGGGACCTA TGAGGTGTCT GTCTACACCA     480
ACTTGATAGT CCGGTCCAAC GGCAGCGTCC TGTGGCTGCC CCCTGCCATC TACAAGAGCG     540
CCTGCAAGAT TGAGGTGAAG TACTTTCCCT TCGACCAGCA GAACTGCACC CTCAAGTTCC     600
GCTCCTGGAC CTATGACCAC ACGGAGATAG ACATGGTCCT CATGACGCCC ACAGCCAGCA     660
TGGATGACTT TACTCCCAGT GGTGAGTGGG ACATAGTGGC CCTCCCAGGG AGAAGGACAG     720
TGAACCCACA AGACCCCAGC TACGTGGACG TGACTTACGA CTTCATCATC AAGCGCAAGC     780
CTCTGTTCTA CACCATCAAC CTCATCATCC CTGCGTGCT CACCACCTTG CTGGCCATCC      840
TCGTCTTCTA CCTGCCATCC GACTGCGGCG AGAAGATGAC ACTGTGCATC TCAGTGCTGC     900
TGGCACTGAC ATTCTTCCTG CTGCTCATCT CCAAGATCGT GCCACCCACC TCCCTCGATG     960
TGCCTCTCAT CGGCAAGTAC CTCATGTTCA CCATGGTGCT GGTCACCTTC TCCATCGTCA    1020
CCAGCGTCTG TGTGCTCAAT GTGCACCACC GCTCGCCCAG CACCCACACC ATGGCACCCT    1080
GGGTCAAGCG CTGCTTCCTG CACAAGCTGC CTACCTTCCT CTTCATGAAG CGCCCTGGCC    1140
CCGACAGCAG CCCGGCCAGA GCCTTCCCGC CCAGCAAGTC ATGCGTGACC AAGCCCGAGG    1200
CCACCGCCAC CTCCACCAGC CCCTCCAACT TCTATGGGAA CTCCATGTAC TTTGTGAACC    1260
CCGCCTCTGC AGCTTCCAAG CTCCAGCCG GCTCTACCCC GGTGGCTATC CCCAGGGATT     1320
TCTGGCTGCG GTCCTCTGGG AGGTTCCGAC AGGATGTGCA GGAGGCATTA GAAGGTGTCA    1380
GCTTCATCGC CCAGCACATG AAGAATGACG ATGAAGACCA GAGTGTCGTT GAGGACTGGA    1440
AGTACGTGGC TATGGTGGTG GACCGGCTGT TCCTGTGGGT GTTCATGTTT GTGTGCGTCC    1500
TGGGCACTGT GGGGCTCTTC CTGCCGCCCC TCTTCCAGAC CCATGCAGCT TCTGAGGGGC    1560
CCTACGCTGC CCAGCGTGAC TGAGGGCCCC CTGGTTGTG GGGTGAGAGG ATGTGAGTGG     1620
CCGGGTGGGC ACTTTGCTGC TTCTTTCTGG GTTGTGGCCG ATGAGGCCCT AAGTAAATAT    1680
GTGAGCATTG GCCATCAACC CCATCAAACC AGCCACAGCC GTGAACAGG CAAGGATGGG     1740
GGCCTGGCCT GTCCTCTCTG AATGCCTTGG AGGGATCCCA GGAAGCCCCA GTAGGAGGGA    1800
GCTTCAGACA GTTCAATTCT GGCCTGTCTT CCTTCCCTGC ACCGGGCAAT GGGGATAAAG    1860
ATGACTTCGT AGCAGCACCT ACTATGCTTC AGGCATGGTG CCGGCCTGCC TCTCC         1915

(2) INFORMATION FOR SEQ ID NO:18:

(i) SEQUENCE CHARACTERISTICS:
```

```
          (A) LENGTH: 498 amino acids
          (B) TYPE: amino acid
          (D) TOPOLOGY: unknown (ii) MOLECULE TYPE: protein (xi) SEQUENCE DESCRIPTION: SEQ ID NO:18:

Met Arg Arg Ala Pro Ser Leu Val Leu Phe Leu Val Ala Leu Cys
1               5                   10                  15

Gly Arg Gly Asn Cys Arg Val Ala Asn Ala Glu Glu Lys Leu Met Asp
            20                  25                  30

Asp Leu Leu Asn Lys Thr Arg Tyr Asn Asn Leu Ile Arg Pro Ala Thr
                35                  40                  45

Ser Ser Ser Gln Leu Ile Ser Ile Lys Leu Gln Leu Ser Leu Ala Gln
50                          55                  60

Leu Ile Ser Val Asn Glu Arg Glu Gln Ile Met Thr Thr Asn Val Trp
65                      70                  75                  80

Leu Lys Gln Glu Trp Thr Asp Tyr Arg Leu Thr Trp Asn Ser Ser Arg
                    85                  90                  95

Tyr Glu Gly Val Asn Ile Leu Arg Ile Pro Ala Lys Arg Ile Trp Leu
                100                 105                 110

Pro Asp Ile Val Leu Tyr Asn Asn Ala Asp Gly Thr Tyr Glu Val Ser
            115                 120                 125

Val Tyr Thr Asn Leu Ile Val Arg Ser Asn Gly Ser Val Leu Trp Leu
130                 135                 140

Pro Pro Ala Ile Tyr Lys Ser Ala Cys Lys Ile Glu Val Lys Tyr Phe
145                 150                 155                 160

Pro Phe Asp Gln Gln Asn Cys Thr Leu Lys Phe Arg Ser Trp Thr Tyr
                165                 170                 175

Asp His Thr Glu Ile Asp Met Val Leu Met Thr Pro Thr Ala Ser Met
            180                 185                 190

Asp Asp Phe Thr Pro Ser Gly Glu Trp Asp Ile Val Ala Leu Pro Gly
        195                 200                 205

Arg Arg Thr Val Asn Pro Gln Asp Pro Ser Tyr Val Asp Val Thr Tyr
210                 215                 220

Asp Phe Ile Ile Lys Arg Lys Pro Leu Phe Tyr Thr Ile Asn Leu Ile
225                 230                 235                 240

Ile Pro Cys Val Leu Thr Thr Leu Leu Ala Ile Leu Val Phe Tyr Leu
                245                 250                 255

Pro Ser Asp Cys Gly Glu Lys Met Thr Leu Cys Ile Ser Val Leu Leu
            260                 265                 270

Ala Leu Thr Phe Phe Leu Leu Leu Ile Ser Lys Ile Val Pro Pro Thr
        275                 280                 285

Ser Leu Asp Val Pro Leu Ile Gly Lys Tyr Leu Met Phe Thr Met Val
290                 295                 300

Leu Val Thr Phe Ser Ile Val Thr Ser Val Cys Val Leu Asn Val His
305                 310                 315                 320

His Arg Ser Pro Ser Thr His Thr Met Ala Pro Trp Val Lys Arg Cys
                325                 330                 335

Phe Leu His Lys Leu Pro Thr Phe Leu Phe Met Lys Arg Pro Gly Pro
            340                 345                 350

Asp Ser Ser Pro Ala Arg Ala Phe Pro Pro Ser Lys Ser Cys Val Thr
        355                 360                 365

Lys Pro Glu Ala Thr Ala Thr Ser Thr Ser Pro Ser Asn Phe Tyr Gly
370                 375                 380
```

-continued

```
Asn Ser Met Tyr Phe Val Asn Pro Ala Ser Ala Ala Ser Lys Ser Pro
385                 390                 395                 400

Ala Gly Ser Thr Pro Val Ala Ile Pro Arg Asp Phe Trp Leu Arg Ser
                405                 410                 415

Ser Gly Arg Phe Arg Gln Asp Val Gln Glu Ala Leu Glu Gly Val Ser
            420                 425                 430

Phe Ile Ala Gln His Met Lys Asn Asp Asp Glu Asp Gln Ser Val Val
        435                 440                 445

Glu Asp Trp Lys Tyr Val Ala Met Val Val Asp Arg Leu Phe Leu Trp
    450                 455                 460

Val Phe Met Phe Val Cys Val Leu Gly Thr Val Gly Leu Phe Leu Pro
465                 470                 475                 480

Pro Leu Phe Gln Thr His Ala Ala Ser Glu Gly Pro Tyr Ala Ala Gln
                485                 490                 495

Arg Asp
```

METHODS FOR IDENTIFYING AGONISTS AND ANTAGONISTS FOR HUMAN NEURONAL NICOTINIC ACETYLCHOLINE RECEPTORS

RELATED APPLICATIONS

This application is a continuation-in-part of U.S. application Ser. No. 08/149,503, filed Nov. 8, 1993, now abandoned; a continuation-in-part of U.S. application Ser. No. 08/028,031, filed Mar. 8, 1993, now abandoned; and a continuation-in-part of U.S. application Ser. No. 07/938,154, filed Nov. 30, 1992, now U.S. Pat. No. 5,981,193, which is a continuation-in-part of U.S. application Ser. No. 07/504,455, filed Apr. 3, 1990, now issued as U.S. Pat. No. 5,369,028, each of which is hereby incorporated by reference herein in their entirety.

FIELD OF THE INVENTION

This invention relates to assays employing DNA encoding human neuronal nicotinic acetylcholine receptor protein subunits, as well as the proteins themselves. In particular, human neuronal nicotinic acetylcholine receptor α-subunit-encoding DNA, α-subunit proteins, β-subunit-encoding DNA, β-subunit proteins, and combinations thereof are employed for the identification of agonists and antagonists of human neuronal nicotinic acetylcholine receptors.

BACKGROUND OF THE INVENTION

Ligand-gated ion channels provide a means for communication between cells of the central nervous system. These channels convert a signal (e.g., a chemical referred to as a neurotransmitter) that is released by one cell into an electrical signal that propagates along a target cell membrane. A variety of neurotransmitters ant neurotransmitter receptors exist in the central and peripheral nervous systems. Five families of ligand-gate receptors, including the nicotinic acetylcholine receptors (NAChRs) of neuromuscular and neuronal origins, have been identified (Stroud et al. (1990) Biochemistry 29:11009–11023). There is, however, little understanding of the manner in which the variety of receptors generates different responses to neurotransmitters or to other modulating ligands in different regions of the nervous system.

The nicotinic acetylcholine receptors (NAChRs) are multisubunit proteins of neuromuscular and neuronal origins. These receptors form ligand-gated ion channels that mediate synaptic transmission between nerve and muscle and between neurons upon interaction with the neurotransmitter acetylcholine (ACh). Since various nicotinic acetylcholine receptor (NAChR) subunits exist, a variety of NAChR compositions (i.e., combinations of subunits) exist. The different NAChR compositions exhibit different specificities for various ligands and are thereby pharmacologically distinguishable. Thus, the nicotinic acetylcholine receptors expressed at the vertebrate neuromuscular junction in vertebrate sympathetic ganglia and in the vertebrate central nervous system have been distinguished on the basis of the effects of various ligands that bind to different NAChR compositions. For example, the elapid α-neurotoxins that block activation of nicotinic acetylcholine receptors at the neuromuscular junction do not block activation of some neuronal nicotinic acetylcholine receptors that are expressed on several different neuron-derived cell lines.

Muscle NAChR is a glycoprotein composed of five subunits with the stoichiometry $(\alpha)_2\beta(\gamma$ or $\epsilon)\delta$. Each of the subunits has a mass of about 50–60 kilodaltons (kd) and is encoded by a different gene. The $(\alpha)_2\beta(\gamma$ or $\epsilon)\delta$ complex forms functional receptors containing two ligand binding sites and a ligand-gated transmembrane channel. Upon interaction with a cholinergic agonist, muscle nicotinic AChRs conduct sodium ions. The influx of sodium ions rapidly short-circuits the normal ionic gradient maintained across the plasma membrane, thereby depolarizing the membrane. By reducing the potential difference across the membrane, a chemical signal is transduced into an electrical signal that signals muscle contraction at the neuromuscular junction.

Functional muscle nicotinic acetylcholine receptors have been formed with αβδγ subunits, αβδ subunits, αβδ subunits, αδγ subunits or αδ subunits, but not with only one subunit (see e.g., Kurosaki et al. (1987) FEBS Lett. 214: 253–258; Camacho et al. (1993) J. Neuroscience 13:605–613). In contrast, functional neuronal AChRs (nAChRs) can be formed from a subunits alone or combinations of α and β subunits. The larger a subunit is generally believed to be the ACh-binding subunit and the lower molecular weight β subunit is generally believed to be the structural subunit, although it has not been definitively demonstrated that the β subunit does not have the ability to bind ACh. Each of the subunits which participate in the formation of a functional ion channel are, to the extent they contribute to the structure of the resulting channel, "structural" subunits, regardless of their ability (or inability) to bind ACh. Neuronal AChRs (nAChRs), which are also ligand-gated ion channels, are expressed in ganglia of the autonomic nervous system and in the central nervous system (where they mediate signal transmission), in post-synaptic locations (where they modulate transmission), and in pre- and extra-synaptic locations (where they may have additional functions).

DNA encoding NAChRs has been isolated from several sources. Based on the information available from such work, it has been evident for some time that NAChRs expressed in muscle, in autonomic ganglia, and in the central nervous system are functionally diverse. This functional diversity could be due, at least in part, to the large number of different NAChR subunits that exist. There is an incomplete understanding, however, of how and which NAChR subunits combine to generate unique NAChR subtypes, particularly in neuronal cells. Indeed, there is evidence that only certain NAChR subtypes may be involved in diseases such as Alzheimer's disease. Moreover, it is not clear whether NAChRs from analogous tissues or cell types are similar across species.

Accordingly, there is a need for the isolation and characterization of DNAs encoding each human neuronal NAChR subunit, recombinant cells containing such subunits and receptors prepared therefrom. In order to study the unction of human neuronal AChRs and to obtain disease-specific pharmacologically active agents, there is also a need to obtain isolated (preferably purified) human neuronal nicotinic AChRs, and isolated (preferably purified) human neuronal nicotinic AChR subunits. In addition, there is also a need to develop assays to identify such pharmacologically active agents.

The availability of such DNAs, cells, receptor subunits and receptor compositions will eliminate the uncertainty of speculating as to human nNAChR structure and function based on predictions drawn from non-human nNAChR data, or human or non-human muscle or ganglia NAChR data.

Therefore, it is an object herein to provide methods for screening compounds to identify compounds that modulate the activity of human neuronal AChRs.

BRIEF DESCRIPTION OF THE INVENTION

In accordance with the present invention, there are provided methods for identifying compounds which modulate the activity of NAChRs. Invention methods employ isolated DNAs encoding human alpha and beta subunits of neuronal NAChRs and the polypeptides encoded thereby.

Further in accordance with the present invention, there are provided recombinant human neuronal nicotinic AChR subunits, including $\alpha_2$, $\alpha_3$, $\alpha_4$, $\alpha_5$, $\alpha_6$, $\alpha_7$, $\beta_2$, $\beta_3$ and $\beta_4$ subunits, as well as methods for the production thereof. In addition, recombinant human neuronal nicotinic acetylcholine receptors containing at least one human neuronal nicotinic AChR subunit are also provided, as well as methods for the production thereof. Further provided are recombinant neuronal nicotinic AChRs that contain a mixture of one or more NAChR subunits encoded by a host cell, and one or more nNAChR subunits encoded by heterologous DNA or RNA (i.e., DNA or RNA as described herein that has been introduced into the host cell), as well as methods for the production thereof.

Plasmids containing DNA encoding the above-described subunits are also provided. Recombinant cells containing the above-described DNA, mRNA or plasmids are also provided herein. Such cells are useful, for example, for replicating DNA, for producing human NAChR subunits and recombinant receptors, and for producing cells that express receptors containing one or more human subunits.

The DNA, mRNA, vectors, receptor subunits, receptor subunit combinations and cells provided herein permit production of selected neuronal nicotinic AChR receptor subtypes and specific combinations thereof, as well as antibodies to said receptor subunits. This provides a means to prepare synthetic or recombinant receptors and receptor subunits that are substantially free of contamination from many other receptor proteins whose presence can interfere with analysis of a single NAChR subtype. The availability of desired receptor subtypes makes it possible to observe the effect of a drug substance on a particular receptor subtype and to thereby perform initial in vitro screening of the drug substance in a test system that is specific for humans and specific for a human neuronal nicotinic AChR subtype.

The availability of subunit-specific antibodies makes possible the application of the technique of immunohistochemistry to monitor the distribution and expression density of various subunits (e.g., in normal vs diseased brain tissue). Such antibodies could also be employed for diagnostic and therapeutic applications.

The ability to screen drug substances in vitro to determine the effect of the drug on specific receptor compositions should permit the development and screening of receptor subtype-specific or disease-specific drugs. Also, testing of single receptor subunits or specific receptor subtype combinations with a variety of potential agonists or antagonists provides additional information with respect to the function and activity of the individual subunits and should lead to the identification and design of compounds that are capable of very specific interaction with one or more of the receptor subunits or receptor subtypes. The resulting drugs should exhibit fewer unwanted side effects than drugs identified by screening with cells that express a variety of subtypes.

Further in relation to drug development and therapeutic treatment of various disease states, the availability of DNAs encoding human nNAChR subunits enables identification of any alterations in such genes (e.g., mutations) which may correlate with the occurrence of certain disease states. In addition, the creation of animal models of such disease states becomes possible, by specifically introducing such mutations into synthetic DNA sequences which can then be introduced into laboratory animals or in vitro assay systems to determine the effects thereof.

DETAILED DESCRIPTION OF THE INVENTION

Figure 1A:
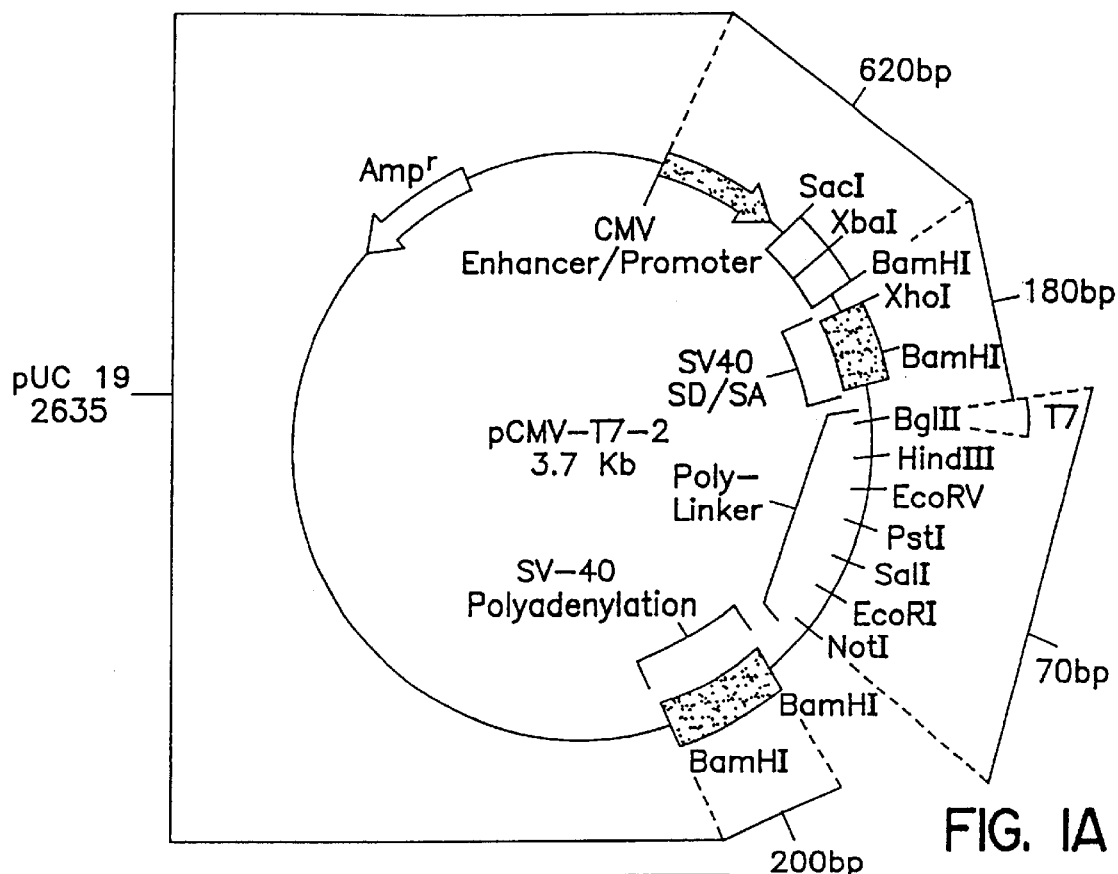
FIGS. 1A and 1B presents a restriction map of two pCMV promoter-based vectors, pCMV-T7-2 and pCMV-T7-3.

In accordance with the present invention, we have developed methods for identifying compounds which modulate the activity of NAChRs. Invention methods employ DNAs encoding human alpha and beta subunits of neuronal NAChRs, and the polypeptides encoded thereby. Specifically, screening employing DNAs encoding human $\alpha_2$, $\alpha_3$, $\alpha_4$, $\alpha_5$, $\alpha_6$, $\alpha_7$, $\beta_2$, $\beta_3$ and $\beta_4$ subunits of neuronal NAChRs is described herein.

As used herein, isolated (or substantially pure) as a modifier of DNA, RNA, polypeptides or proteins means that the DNA, RNA, polypeptides or proteins so designated have been separated from their in vivo cellular environments through the efforts of human beings. Thus as used herein, isolated (or substantially pure) DNA refers to DNAs purified according to standard techniques employed by those skilled in the art (see, e.g., Sambrook et al. (1989) *Molecular Cloning: A Laboratory Manual*, 2nd ed., Cold Spring Harbor Laboratory Press, Cold Spring Harbor, N.Y.).

Similarly, as used herein, "recombinant" as a modifier of DNA, RNA, polypeptides or proteins means that the DNA, RNA, polypeptides or proteins so designated hav, been prepared by the efforts of human beings, e.g., by cloning, recombinant expression, and the like. Thus as used herein, recombinant proteins, for example, refers to proteins produced by a recombinant host, expressing DNAs which have been added to that host through the efforts of human beings.

As used herein, a human alpha subunit gene is a gene that encodes an alpha subunit of a human neuronal nicotinic acetylcholine receptor. The alpha subunit is a subunit of the NAChR to which ACh binds. Assignment of the name "alpha" to a putative nNAChR subunit, according to Deneris et al. [Tips (1991) 12:34–40] is based on the conservation of adjacent cysteine residues in the presumed extracellular domain of the subunit that are the homologues of cysteines 192 and 193 of the Torpedo alpha subunit (see Noda et al. (1982) Nature 299:793–797). As used herein, an alpha subunit subtype refers to a human nNAChR subunit that is encoded by DNA that hybridizes under high stringency conditions to at least one of the nNAChR alpha subunit-encoding DNAs (or deposited clones) disclosed herein. An alpha subunit also binds to ACh under physiological conditions and at physiological concentrations and, in the optional presence of a beta subunit (i.e., some alpha subunits are functional alone, while others require the presence of a beta subunit), generally forms a functional AChR as assessed by methods described herein or known to those of skill in this art.

Also contemplated are alpha subunits encoded by DNAs that encode alpha subunits as defined above, but that by virtue of degeneracy of the genetic code do not necessarily hybridize to the disclosed DNA or deposited clones under specified hybridization conditions. Such subunits also form a functional receptor, as assessed by the methods described herein or known to those of skill in the art, generally with one or more beta subunit subtyped Typically, unless an alpha subunit is encoded by RNA that arises from alternative splicing (i.e., a splice variant), alpha-encoding DNA and the alpha subunit encoded thereby share substantial sequence homology with at least one of the alpha subunit DNAs (and proteins encoded thereby) described or deposited herein. It is understood that DNA or RNA encoding a splice variant may overall share less than 90% homology with the DNA or RNA provided herein, but include regions of nearly 100% homology to a DNA fragment or deposited clone described herein, and encode an open reading frame that includes start and stop codons and encodes a functional alpha subunit.

As used herein, a splice variant refers to variant NAChR subunit-encoding nucleic acid(s) produced by differential processing of primary transcript(s) of genomic DNA, resulting in the production of more than one type of mRNA. cDNA derived from differentially processed genomic DNA will encode NAChR subunits that have regions of complete amino acid identity and regions having different amino acid sequences. Thus, the same genomic sequence can lead to the production of multiple, related mRNAs and proteins. Both the resulting mRNAs and proteins are referred to herein as "splice variants".

Stringency of hybridization is used herein to refer to conditions under which polynucleic acid hybrids are stable. As known to those of skill in the art, the stability of hybrids is reflected in the melting temperature ($T_m$) of the hybrids. $T_m$ can be approximated by the formula:

$$81.5° C.-16.6(\log_{10}[Na^+])+0.41(\%G+C)-600/l,$$

where l is the length of the hybrids in nucleotides. $T_m$ decreases approximately 1–1.5° C. with every 1% decrease in sequence homology. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions. Thus, as used herein:

(1) HIGH STRINGENCY conditions, with respect to fragment hybridization, refer to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High is stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C.;

(2) MODERATE STRINGENCY conditions, with respect to fragment hybridization, refer to conditions equivalent to hybridization in 50% formamide, 5×Denhardt's solution, 5×SSPE, 0.2% SDS at 42° C., followed by washing in 0.2×SSPE, 0.2% SDS, at 65° C.;

(3) LOW STRINGENCY conditions, with respect to fragment hybridization, refer to conditions equivalent to hybridization in 10% formamide, 5×Denhardt's solution, 6×SSPE, 0.2% SDS, followed by washing in 1×SSPE, 0.2% SDS, at 50° C.; and (4) HIGH STRINGENCY conditions, with respect to oligonucleotide (i.e., synthetic DNA s about 30 nucleotides in length) hybridization, refer to conditions equivalent to hybridization in 10% formamide, 5×Denhardt's solution, 6×SSPE, 0.2% SDS at 42° C., followed by washing in 1×SSPE, and 0.2% SDS at 50° C.

It is understood that these conditions may be duplicated using a variety of buffers and temperatures and that they are not necessarily precise.

Denhardt's solution and SSPE (see, e.g., Sambrook, Fritsch, and Maniatis, in: *Molecular Cloning, A Laboratory Manual*, 2nd ed., Cold Spring Harbor Laboratory Press, 1989) are well known to those of skill in the art as are other suitable hybridization buffers. For example, SSPE is pH 7.4 phosphate-buffered 0.18M NaCl. SSPE can be prepared, for example, as a 20× stock solution by dissolving 175.3 g of NaCl, 27.6 g of $NaH_2PO_4$ and 7.4 g EDTA in 800 ml of water, adjusting the pH to 7.4, and then adding water to 1 liter. Denhardt's solution (see, Denhardt (1966) Biochem. Biophys. Res. Commun. 23:641) can be prepared, for example, as a 50× stock solution by mixing 5 g Ficoll (Type 400, Pharmacia LKB Biotechnology, INC., Piscataway N.J.), 5 g of polyvinylpyrrolidone, 5 g bovine serum albumin (Fraction V; Sigma, St. Louis Mo.) water to 500 ml and filtering to remove particulate matter.

As used herein, the phrase "substantial sequence homology" refers to nucleotide sequences which share at least about 90% identity, and amino acid sequences which typically share more than 95% amino acid identity. It is recognized, however, that proteins (and DNA or mRNA encoding such proteins) containing less than the above-described level of homology arising as splice variants or that are modified by conservative amino acid substitutions (or substitution of degenerate codons) are contemplated to be within the scope of the present invention.

The phrase "substantially the same" is used herein in reference to the nucleotide sequence of DNA, the ribonucleotide sequence of RNA, or the amino acid sequence of protein, that have slight and non-consequential sequence variations from the actual sequences disclosed herein. Species that are substantially the same are considered to be equivalent to the disclosed sequences and as such are within the scope of the appended claims. In this regard, "slight and non-consequential sequence variations" mean that sequences that are substantially the same as the DNA, RNA, or proteins disclosed and claimed herein are functionally equivalent to the human-derived sequences disclosed and claimed herein. Functionally equivalent sequences will function in substantially the same manner to produce substantially the same compositions as the human-derived nucleic acid and amino acid compositions disclosed and claimed herein. In particular, functionally equivalent DNAs encode human-derived proteins that are the same as those disclosed herein or that have conservative amino acid variations, such as substitution of a non-polar residue for another non-polar residue or a charged residue for a similarly charged residue. These changes include those recognized by those of skill in the art as those that do not substantially alter the tertiary structure of the protein.

As used herein, "$\alpha_2$ subunit DNA" refers to DNA that encodes a human neuronal nicotinic acetylcholine receptor subunit of the same name, and to DNA that hybridizes under conditions of high stringency to the DNA of SEQ ID No. 1, or to DNA that encodes the amino acid sequence set forth in SEQ ID No. 2. Typically, unless an $\alpha_2$ subunit arises as a splice variant, an $\alpha_2$ DNA shares substantial sequence homology (greater than about 90%) with the $\alpha_2$ DNA described herein. DNA or RNA encoding a splice variant may share less than 90% overall sequence homology with the DNA or RNA described herein, but such a splice variant would include regions of nearly 100% homology to the above-described DNA.

As used herein, "$\alpha_3$ subunit DNA" refers to DNA that encodes a neuronal subunit of the same name, and to DNA that hybridizes under conditions of high stringency to the DNA of SEQ ID No. 3, or to the DNA of deposited clone having ATCC Accession No. 68278, or to DNA that encodes the amino acid sequence set forth in SEQ ID No. 4. Typically, unless an $\alpha_3$ arises as a splice variant, an $\alpha_3$ DNA shares substantial sequence homology (greater than about 90%) with the $\alpha_3$ DNA described herein. DNA or RNA encoding a splice variant may share less than 90% overall sequence homology with the DNA or RNA provided herein, but such a splice variant would include regions of nearly 100% homology to the above described DNA.

As used herein, "$\alpha_4$ subunit DNA" refers to DNA encoding a neuronal nicotinic acetylcholine receptor subunit of the same name. Such DNA can be characterized in a number of ways, for example said DNA may encode the amino acid sequence set forth in SEQ. ID No. 6, or said DNA may encode the amino acid sequence encoded by clone HnAChRα4.2, deposited under ATCC Accession No. 69239, or the 5' nucleotides of said DNA may encode the amino acid sequence encoded by clone HnAChRα4.1, deposited under ATCC Accession No. 69152.

Presently preferred $\alpha_4$-encoding DNAs can be characterized as follows said DNA may hybridize to the coding sequence set forth in SEQ. ID No. 5 (preferably to substantially the entire coding sequence thereof, i.e., nucleotides 184–2067) under high stringency conditions, or said DNA may hybridize under high stringency conditions to the sequence (preferably to substantially the entire sequence) of the $\alpha_4$-encoding insert of clone HnAChRα4.2, deposited under ATCC Accession No. 69239, or the 5' nucleotides of said DNA may hybridize under high stringency conditions to the sequence of the $\alpha_4$-encoding insert of clone HnAChRα4.1, deposited under ATCC Accession No. 69152.

Especially preferred $\alpha_4$-encoding DNAs of the invention are characterized as follows DNA having substantially the same nucleotide sequence as the coding region set forth in SEQ. ID No. 5 (i.e., nucleotides 184–2067 thereof), or DNA having substantially the same nucleotide sequence as the $\alpha_4$-encoding insert of clone HnAChRα4.2, deposited under ATCC Accession No. 69239, or the 5' nucleotides of said DNA have substantially the same sequence as the $\alpha_4$-encoding insert of clone HnAChRα4.1, deposited under ATCC Accession No. 69152.

Typically, unless an $\alpha_4$ subunit arises as a splice variant, $\alpha_4$-encoding DNA will share substantial sequence homology (i.e., greater than about 90%), with the $\alpha_4$ DNAs described or deposited herein. DNA or RNA encoding a splice variant may share less than 90% overall sequence homology with the DNA or RNA provided herein, but such a splice variant would include regions of nearly 100% homology to the above-described DNAs.

As used herein, "$\alpha_5$ subunit DNA" refers to DNA that encodes a human neuronal nicotinic acetylcholine receptor subunit of the same name, and to DNA that hybridizes under conditions of high stringency to the DNA of SEQ ID No. 7, or to DNA that encodes the amino acid sequence set forth in SEQ ID No. 8. Typically, unless an as subunit arises as a splice variant, an $\alpha_5$ DNA shares substantial sequence homology (greater than about 90%) with the $\alpha_5$ DNA described herein. DNA or RNA encoding a splice variant may share less than 90% overall sequence homology with the DNA or RNA described herein, but such a splice variant would include regions of nearly 100% homology to the above-described DNA. Human $\alpha_5$ subunit DNA has been described in the art, for example, by Chini et al. (1992) Proc. Natl. Acad. Sci. USA 89:1572–1576.

As used herein, "$\alpha_6$ subunit DNA" refers to DNA that encodes a neuronal subunit of the same name, and to DNA that hybridizes under conditions of high stringency to the DNA of SEQ ID No. 9, or to DNA that encodes the amino acid sequence set forth in SEQ ID No. 10. Typically, unless an $\alpha_6$ arises as a splice variant, an $\alpha_6$ DNA shares substantial sequence homology (greater than about 90%) with the $\alpha_6$ DNA described herein. DNA or RNA encoding a splice variant may share less than 90% overall sequence homology with the DNA or RNA provided herein, but such a splice variant would include regions of nearly 100% homology to the above described DNA.

As used herein, "$\alpha_7$ subunit DNA" refers to DNA encoding a neuronal nicotinic acetylcholine receptor subunit of the same name. Such DNA can be characterized in a number of ways, for example, the nucleotides of said DNA may encode the amino acid sequence set forth in SEQ. ID No. 8. Presently preferred $\alpha_7$-encoding DNAs can be characterized as DNA which hybridizes under high stringency conditions to the coding sequence set forth in SEQ. ID No. 7 (preferably to substantially the entire coding sequence thereof, i.e., nucleotides 73–1581). Especially preferred $\alpha_7$-encoding DNAs of the invention are characterized as having substantially the same nucleotide sequence as the coding sequence set forth in SEQ. ID No. 7 (i.e., nucleotides 73–1581 thereof).

Typically, unless an $\alpha_7$ subunit arises as a splice variant, $\alpha_7$-encoding DNA will share substantial sequence homology (greater than about 90%) with the $\alpha_7$ DNAs described or deposited herein. DNA or RNA encoding a splice variant may share less than 90% overall sequence homology with the DNA or RNA provided herein, but such DNA would include regions of nearly 100% homology to the above-described DNA.

The $\alpha_7$ subunits derived from the above-described DNA are expected to bind to the neurotoxin α-bungarotoxin (α-bgtx). The activity of AChRs that contain $\alpha_7$ subunits should be inhibited upon interaction with α-bgtx. Amino acid residues 210 through 217, as set forth in SEQ ID No. 8, are believed to be important elements in the binding of α-bgtx (see, for example, Chargeaux et al. (1992) 13:299–301).

As used herein, a human beta subunit gene is a gene that encodes a beta subunit of a human neuronal nicotinic acetylcholine receptor. Assignment of the name "beta" to a putative nNAChR subunit, according to Deneris et al. supra, is based on the lack of adjacent cysteine residues (which are characteristic of alpha subunits). The beta subunit is frequently referred to as the structural NAChR subunit (although it is possible that beta subunits also have ACh binding properties). Combination of beta subunit(s) with appropriate alpha subunit(s) leads to the formation of a functional receptor. As used herein, a beta subunit subtype refers to a nNAChR subunit that is encoded by DNA that hybridizes under high stringency conditions to at least one of the nNAChR-encoding DNAs (or deposited clones) disclosed herein. A beta subunit forms a functional NAChR, as assessed by methods described herein or known to those of skill in this art, with appropriate alpha subunit subtype(s).

Also contemplated are beta subunits encoded by DNAs that encode beta subunits as defined above, but that by virtue of degeneracy of the genetic code do not necessarily hybridize to the disclosed DNA or deposited clones under the specified hybridization conditions. Such subunits also form functional receptors, as assessed by the methods described herein or known to those of skill in the art, in combination with appropriate alpha subunit subtype(s). Typically, unless a beta subunit is encoded by RNA that arises as a splice variant, beta-encoding DNA and the beta subunit encoded thereby share substantial sequence homology with the beta-encoding DNA and beta subunit protein described herein. It is understood that DNA or RNA encoding a splice variant may share less than 90% overall homology with the DNA or RNA provided herein, but such DNA will include regions of nearly 100% homology to the DNA described herein.

As used herein, "$\beta_2$ subunit DNA" refers to DNA that encodes a neuronal subunit of the same name and, to DNA that hybridizes under conditions of high stringency to the DNA of SEQ ID No. 13, or to the DNA of deposited clone HnAChR$\beta$2, having ATCC Accession No. 68279, or to DNA encoding the amino acid sequence set forth in SEQ ID No. 14. Typically, unless a $\beta_2$ subunit arises as a splice variant, a $\beta_2$ DNA shares substantial sequence homology (greater than about 90%) with the $\beta_2$ DNA described herein. DNA or RNA encoding a splice variant may share overall less than 90% homology with the DNA or RNA provided herein, but such a splice variant would include regions of nearly 100% homology to the above-described DNA.

As used herein, "$\beta_3$ subunit DNA" refers to DNA that encodes a neuronal subunit of the same name and, to DNA that hybridizes under conditions of high stringency to the DNA of SEQ ID No. 15, or to DNA encoding the amino acid sequence set forth in SEQ ID No. 16. Typically, unless a $\beta_3$ subunit arises as a splice variant, a $\beta_2$ DNA shares substantial sequence homology (greater than about 90%) with the $\beta_3$ DNA described herein. DNA or RNA encoding a splice variant may share overall less than 90% homology with the DNA or RNA provided herein, but such a splice variant would include regions of nearly 100% homology to the above-described DNA.

As used herein, "$\beta_4$ subunit DNA" refers to DNA encoding a neuronal nicotinic acetylcholine receptor subunit of the same name. Such DNA can be characterized in a number of ways, for example, the nucleotides of said DNA may encode the amino acid sequence set forth in SEQ. ID No. 18. Presently preferred $\beta_4$-encoding DNAs can be characterized as DNA which hybridizes under high stringency conditions to the coding sequence set forth in SEQ. ID No. 17 (preferably to substantially the entire coding sequence thereof, i.e., nucleotides 87–1583). Especially preferred $\beta_4$-encoding DNAs of the invention are characterized as having substantially the same nucleotide sequence as set forth in SEQ. ID No. 17.

Typically, unless a $\beta_4$ subunit arises as a splice variant, $\beta_4$-encoding DNA will share substantial sequence homology (greater than about 90%) with the $\beta_4$ DNAs described or deposited herein. DNA or RNA encoding a splice variant may share less than 90% overall sequence homology with the DNA or RNA provided herein, but such DNA would include regions of nearly 100% homology to the above-described DNA.

DNA encoding human neuronal nicotinic AChR alpha and beta subunits may be isolated by screening suitable human cDNA or human genomic libraries under suitable hybridization conditions with DNA disclosed herein (including nucleotides derived from any of SEQ ID Nos. 1, 3, 5, 7, 9, 11, 13, 15 or 17 or with any of the deposited clones referred to herein. Suitable libraries can be prepared from neuronal tissue samples, hippocampus tissue, or cell lines, such as the human neuroblastoma cell line IMR32 (ATCC Accession No. CCL127), and the like. The library is preferably screened with a portion of DNA including the entire subunit-encoding sequence thereof, or the library may be screened with a suitable probe.

As used herein, a probe is single-stranded DNA or RNA that has a sequence of nucleotides that includes at least 14 contiguous bases that are the same as (or the complement of) any 14 bases set forth in any of SEQ ID Nos. 1, 3, 5, 7, 9, 11, 13, 15 or 17 or in the subunit encoding DNA in any of the deposited clones described herein. Preferred regions from which to construct probes include 5' and/or 3' coding sequences, sequences predicted to encode transmembrane domains, sequences predicted to encode the cytoplasmic loop, signal sequences, acetylcholine (ACh) and $\alpha$-bungarotoxin ($\alpha$-bgtx) binding sites, and the like. Amino acids 210–220 are typically involved in ACh and $\alpha$-bgtx binding. The approximate amino acid residues which comprise such regions for other preferred probes are set forth in the following table:

| Subunit | Signal Sequence | TMD1 * | TMD2 | TMD3 | TMD4 | Cytoplasmic Loop |
|---|---|---|---|---|---|---|
| $\alpha_2$ | 1–55 | 264–289 | 297–320 | 326–350 | 444–515 | 351–443 |
| $\alpha_3$ | 1–30 | 240–265 | 273–296 | 302–326 | 459–480 | 327–458 |
| $\alpha_4$ | 1–33 | 241–269 | 275–289 | 303–330 | 593–618 | 594–617 |
| $\alpha_5$ | 1–22 | 250–275 | 282–304 | 310–335 | 422–437 | 336–421 |
| $\alpha_6$ | 1–30 | 240–265 | 272–294 | 301–326 | 458–483 | 327–457 |
| $\alpha_7$ | 1–23 | 229–256 | 262–284 | 290–317 | 462–487 | 318–461 |
| $\beta_2$ | 1–25 | 234–259 | 267–288 | 295–320 | 453–477 | 321–452 |
| $\beta_3$ | 1–20 | 232–258 | 265–287 | 293–318 | 421–446 | 319–420 |
| $\beta_4$ | 1–23 | 234–258 | 264–285 | 290–319 | 454–478 | 320–453 |

* TMD = transmembrane domain

Alternatively, portions of the DNA can be used as primers to amplify selected fragments in a particular library.

After screening the library, positive clones are identified by detecting a hybridization signal; the identified clones are characterized by restriction enzyme mapping and/or DNA sequence analysis, and then examined, by comparison with the sequences set forth herein or with the deposited clones described herein, to ascertain whether they include DNA encoding a complete alpha or beta subunit. If the selected clones are incomplete, they may be used to rescreen the same or a different library to obtain overlapping clones. If desired, the library can be rescreened with positive clones until overlapping clones that encode an entire alpha or beta subunit are obtained. If the library is a cDNA library, then the overlapping clones will include an open reading frame. If the library is genomic, then the overlapping clones may include exons and introns. In both instances, complete clones may be identified by comparison with the DNA and encoded proteins provided herein.

Complementary DNA clones encoding various subtypes of human nNAChR alpha and beta subunits have been isolated. Each subtype of the subunit appears to be encoded by a different gene. The DNA clones provided herein may be used to isolate genomic clones encoding each subtype and to isolate any splice variants by screening libraries prepared from different neural tissues. Nucleic acid amplification techniques, which are well known in the art, can be used to locate splice variants of human NAChR subunits. This is accomplished by employing oligonucleotides based on DNA sequences surrounding divergent sequence(s) as primers for amplifying human RNA or genomic DNA. Size and sequence determinations of the amplification products can reveal the existence of splice variants. Furthermore, isolation of human genomic DNA sequences by hybridization can yield DNA containing multiple exons, separated by introns, that correspond to different splice variants of transcripts encoding human NAChR subunits.

It has been found that not all subunit subtypes are expressed in all neural tissues or in all portions of the brain. Thus, in order to isolate cDNA encoding particular subunit subtypes or splice variants of such subtypes, it is preferable to screen libraries prepared from different neuronal or neural tissues. Preferred libraries for obtaining DNA encoding each subunit include: hippocampus to isolate human $\alpha_4$-, and $\alpha_5$-encoding DNA; IMR32 to isolate human $\alpha_3$-, $\alpha_5$-, $\alpha_7$- and $\beta_4$-encoding DNA, thalamus to isolate $\alpha_2$ and $\beta_2$-encoding DNA; and the like.

It appears that the distribution of expression of human neuronal nicotinic AChRs differs from the distribution of such receptors in rat. For example, RNA encoding the rat $\alpha_4$ subunit is abundant in rat thalamus, but is not abundant in rat hippocampus (see, e.g., Wada et al. (1989) J. Comp. Neurol. 284:314–335). No $\alpha_4$-encoding clones could be obtained, however, from a human thalamus library. Instead, human $\alpha_4$ clones were ultimately obtained from a human hippocampus library. Thus, the distribution of $\alpha_4$ nNAChR subunit in humans and rats appears to be quite different.

Rat $\alpha_3$ subunit appears to be a CNS-associated subunit that is abundantly expressed in the thalamus and weakly expressed in the brain stem (see, e.g., Boulter et al. (1986) Nature 319:368–374; Boulter et al. (1987) Proc. Natl. Acad. Sci. USA 84:7763–7767; and Wada et al. (1989) J. Comp. Neurol. 284:314–335). In efforts to clone DNA encoding the human nicotinic AChR $\alpha_3$ subunit, however, several human libraries, including a thalamus library, were unsuccessfully screened. Surprisingly, clones encoding human $\alpha_3$ subunit were ultimately obtained from a brain stem library and from IMR32 cells that reportedly express few, if any, functional nicotinic acetylcholine receptors (see, e.g., Gotti et al. ((1986) Biochem. Biophys. Res. Commun. 137: 1141–1147, and Clementi et al. (1986) J. Neurochem. 47: 291–297).

Rat $\alpha_7$ subunit transcript reportedly is abundantly expressed in the hippocampus (see Seguela et al. (1993) J. Neurosci. 13:596–604). Efforts to clone DNA encoding a human $\alpha_7$ subunit from a human hippocampus library ($1\times10^6$ recombinants) were unsuccessful. Surprisingly, clones encoding a human NAChR $\alpha_7$ subunit were ultimately obtained from an IMR32 cell cDNA library.

The above-described nucleotide sequences can be incorporated into vectors for further manipulation. As used herein, vector (or plasmid) refers to discrete elements that are used to introduce heterologous DNA into cells for either expression or replication thereof. Selection and use of such vehicles are well within the level of skill of the art.

An expression vector includes vectors capable of expressing DNAs that are operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome. Presently preferred plasmids for expression of invention AChR subunits in eukaryotic host cells, particularly mammalian cells, include SV40 promoter-based expression vectors, such as pZeoSV (Invitrogen, San Diego, Calif.) CMV promoter-based vectors such as pcDNA1, pcDNA3, pCEP4 (Inventrogen, San Diego, Calif.), and MMTV promoter-based vectors such as pMAMneo (Clontech, Inc.), and the like.

As used herein, a promoter region refers to a segment of DNA that controls transcription of DNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, and the like.

As used herein, the term "operatively linked" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove or alter 5' untranslated portions of the clones to remove extra, potential alternative translation initiation (i.e., start) codons or other sequences that interfere with or reduce expression, either at the level of transcription or translation. Alternatively, consensus ribosome binding sites (see, for example, Kozak (1991) J. Biol. Chem. 266:19867–19870) can be inserted immediately 5' of the start codon to enhance expression. The desirability of (or need for) such modification may be empirically determined.

As used herein, expression refers to the process by which polynucleic acids are transcribed into mRNA and translated into peptides, polypeptides, or proteins. If the polynucleic acid is derived from genomic DNA, expression may, if an appropriate eukaryotic host cell or organism is selected, include splicing of the mRNA.

Particularly preferred vectors for transfection of mammalian cells are the pSV2dhfr expression vectors, which contain the SV40 early promoter, mouse dhfr gene, SV40 polyadenylation and splice sites and sequences necessary for maintaining the vector in bacteria, cytomegalovirus (CMV) promoter-based vectors such as pcDNA1 (Invitrogen, San Diego, Calif.), and MMTV promoter-based vectors such as pMSG (Catalog No. 27-4506-01 from Pharmacia, Piscataway, N.J.).

Full-length DNAs encoding human neuronal NAChR subunits have been inserted into vector pCMV-T7, a pUC1- based mammalian cell expression vector containing the CMV promoter/enhancer, SV40 splice/donor sites located immediately downstream of the promoter, a polylinker downstream of the splice/donor sites, followed by an SV40 polyadenylation signal. Placement of NAChR subunit DNA between the CMV promoter and SV40 polyadenylation signal provides for constitutive expression of the foreign DNA in a mammalian host cell transfected with the construct. For inducible expression of human NAChR subunit-encoding DNA in a mammalian cell, the DNA can be inserted into a plasmid such as pMSG. This plasmid contains the mouse mammary tumor virus (MMTV) promoter for steroid-inducible expression of operatively associated foreign DNA. If the host cell does not express endogenous glucocorticoid receptors required for uptake of glucocorticoids (i.e., inducers of the MMTV promoter) into the cell, it is necessary to additionally transfect the cell with DNA encoding the glucocorticoid receptor (ATCC accession no. 67200). Full-length human DNA clones encoding human $\alpha_3$, $\alpha_4$, $\alpha_7$ $\beta_2$ and $\beta$ have also been subcloned into pIBI24 (International Biotechnologies, Inc., New Haven, Conn.) or pCMV-T7-2 for synthesis of in vitro transcripts.

In accordance with another embodiment of the present invention, there are provided cells containing the above-described polynucleic acids (i.e., DNA or mRNA). Such host cells as bacterial, yeast and mammalian cells can be used for replicating DNA and producing nAChR subunit(s). Methods for constructing expression vectors, preparing in vitro transcripts, transfecting DNA into mammalian cells, injecting oocytes, and performing electrophysiological and other analyses for assessing receptor expression and function as described herein are also described in PCT Application Nos. PCT/US91/02311, PCT/US91/05625 and PCT/US92/11090, and in co-pending U.S. application Ser. Nos. 07/504,455, 07/563,751 and 07/812,254. The subject matter of these applications are hereby incorporated by reference herein in their entirety.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g., Sambrook et al. (1989) *Molecular Cloning: A Laboratory Manual*, Second Edition, Cold Spring Harbor Laboratory Press). Heterologous DNA may be introduced into host cells by any method known to those of skill in the art, such as transfection with a vector encoding the heterologous DNA by $CaPO_4$ precipitation (see, e.g., Wigler et al. (1979) Proc. Natl. Acad. Sci. 76:1373–1376). Recombinant cells can then be cultured under conditions whereby the subunit(s) encoded by the DNA is (are) expressed. Preferred cells include mammalian cells (e.g., HEK 293, CHO and Ltk cells), yeast cells (e.g., methylotrophic yeast cells, such as *Pichia pastoris*), bacterial cells (e.g., *Escherichia coli*), and the like.

While the DNA provided herein may be expressed in any eukaryotic cell, including yeast cells (such as, for example, *P. pastoris* (see U.S. Pat. Nos. 4,882,279, 4,837,148, 4,929,555 and 4,855,231), *Saccharomyces cerevisiae, Candida tropicalis, Hansenula polyorpha*, and the like), mammalian expression systems, including commercially available systems and other such systems known to those of skill in the art, for expression of DNA encoding the human neuronal nicotinic AChR subunits provided herein are presently preferred. *Xenopus oocytes* are preferred for expression of RNA transcripts of the DNA.

In preferred embodiments, DNA is ligated into a vector, and introduced into suitable host cells to produce transformed cell lines that express a specific human nNAChR receptor subtype, or specific combinations of subtypes. The resulting cell lines can then be produced in quantity for reproducible quantitative analysis of the effects of drugs on receptor function. In other embodiments, mRNA may be produced by in vitro transcription of DNA encoding each subunit. This mRNA, either from a single subunit clone or from a combination of clones, can then be injected into Xenopus oocytes where the mRNA directs the synthesis of the human receptor subunits, which then form functional receptors. Alternatively, the subunit-encoding DNA can be directly injected into oocytes for expression of functional receptors. The transfected mammalian cells or injected oocytes may then be used in the methods of drug screening provided herein.

Cloned full-length DNA encoding any of the subunits of human neuronal nicotinic AChR may be introduced into a plasmid vector for expression in a eukaryotic cell. Such DNA may be genomic DNA or cDNA. Host cells may be transfected with one or a combination of plasmids, each of which encodes at least one human neuronal nicotinic AChR subunit.

Eukaryotic cells in which DNA or RNA may be introduced include any cells that are transfectable by such DNA or RNA or into which such DNA or RNA may be injected. Preferred cells are those that can be transiently or stably transfected and also express the DNA and RNA. Presently most preferred cells are those that can form recombinant or heterologous human neuronal nicotinic AChRs comprising one or more subunits encoded by the heterologous DNA. Such cells may be identified empirically or selected from among those known to be readily transfected or injected.

Exemplary cells for introducing DNA include cells of mammalian origin (e.g., COS cells, mouse L cells, Chinese hamster ovary (CHO) cells, human embryonic kidney cells, African green monkey cells and other such cells known to those of skill in the art), amphibian cells (e.g., *Xenopus laevis* oöcytes), yeast cells (e.g., *Saccharomiyces cerevisiae, Pichia pastoris*), and the like. Exemplary cells for expressing injected RNA transcripts include *Xenopus laevis* oöcytes. Cells that are preferred for transfection of DNA are known to those of skill in the art or may be empirically identified, and include HEK 293 (which are available from ATCC under accession #CRL 1573); Ltk⁻ cells (which are available from ATCC under accession #CCL1.3); COS-7 cells (which are available from ATCC under accession #CRL 1651); and DG44 cells (dhfr⁻ CHO cells; see, e.g., Urlaub et al. (1986) Cell. Molec. Genet. 12: 555). Presently preferred cells include DG44 cells and HEK 293 cells, particularly HEK 293 cells that have been adapted for growth in suspension and that can be frozen in liquid nitrogen and then thawed and regrown. HEK 293 cells are described, for example, in U.S. Pat. No. 5,024,939 to Gorman (see, also, Stillman et al. (1985) Mol. Cell. Biol. 5:2051–2060).

DNA may be stably incorporated into cells or may be transiently introduced using methods known in the art. Stably transfected mammalian cells may be prepared by transfecting cells with an expression vector having a selectable marker gene (such as, for example, the gene for thymidine kinase, dihydrofolate reductase, neomycin resistance, and the like), and growing the transfected cells under conditions selective for cells expressing the marker gene. To produce such cells, the cells should be transfected with a sufficient concentration of subunit-encoding nucleic acids to form human neuronal nicotinic AChRs that contain the human subunits encoded by heterologous DNA. The precise amounts and ratios of DNA encoding the subunits may be empirically determined and optimized for a particular combination of subunits, cells and assay conditions. Recombinant cells that express neuronal nicotinic AChR containing subunits encoded only by the heterologous DNA or RNA are especially preferred. Heterologous DNA may be maintained in the cell as an episomal element or may be integrated into chromosomal DNA of the cell. The resulting recombinant cells may then be cultured or subcultured (or passaged, in the case of mammalian cells) from such a culture or a subculture thereof. Methods for transfection, injection and culturing recombinant cells are known to the skilled artisan. Similarly, the human neuronal nicotinic AChR subunits may be purified using protein purification methods known to those of skill in the art. For example, antibodies or other ligands that specifically bind to one or more of the subunits may be used for affinity purification of the subunit or human neuronal nicotinic AChRs containing the subunits.

In accordance with one embodiment of the present invention, methods for producing cells that express human neuronal nicotinic AChR subunits and functional receptors are also provided. In one such method, host cells are transfected with DNA encoding at least one alpha subunit of a neuronal nicotinic acetylcholine receptor and at least one beta subunit of a neuronal nicotinic acetylcholine receptor. Using methods such as Northern blot or slot blot analysis, transfected cells that contain alpha and/or beta subunit encoding DNA or RNA can be selected. Transfected cells are also analyzed to identify those that express NAChR protein. Analysis can be carried out, for example, by measuring the ability of cells to bind acetylcholine, nicotine, or a nicotine agonist, compared to the nicotine binding ability of untransfected host cells or other suitable control cells, by electrophysiologically monitoring the currents through the cell membrane in response to a nicotine agonist, and the like.

In particularly preferred aspects, eukaryotic cells which contain heterologous DNAs express such DNA and form recombinant functional neuronal nicotinic AChR(s). In more preferred aspects, recombinant neuronal nicotinic AChR activity is readily detectable because it is a type that is absent from the untransfected host cell or is of a magnitude not exhibited in the untransfected cell. Such cells that contain recombinant receptors could be prepared, for example, by causing cells transformed with DNA encoding the human neuronal nicotinic AChR $\alpha_3$ and $\beta_4$ subunits to express the corresponding proteins. The resulting synthetic or recombinant receptor would contain only the $\alpha_3$ and $\beta_4$ nNAChR subunits. Such a receptor would be useful for a variety of applications, e.g., as part of an assay system free of the interferences frequently present in prior art assay systems employing non-human receptors or human tissue preparations. Furthermore, testing of single receptor subunits with a variety of potential agonists or antagonists would provide additional information with respect to the function and activity of the individual subunits. Such information may lead to the identification of compounds which are capable of very specific interaction with one or more of the receptor subunits. Such specificity may prove of great value in medical application.

Thus, DNA encoding one or more human neuronal nicotinic AChR subunits may be introduced into suitable host cells (e.g., eukaryotic or prokaryotic cells) for expression of individual subunits and functional NAChRs. Preferably combinations of alpha and beta subunits may be introduced into cells: such combinations include combinations of any one or more of all $\alpha_1$, $\alpha_2$, $\alpha_3$, $\alpha_4$, $\alpha_5$, $\alpha_6$ and $\alpha_7$ with $\beta_2$, $\beta_3$ or $\beta_4$. Sequence information for $\alpha_1$ is presented in Biochem. Soc. Trans. (1989) 17:219–220; sequence information for $\alpha_5$ is presented in Proc. Natl. Acad. Sci.USA (1992) 89:1572–1576; and sequence information for $\alpha_2$, $\alpha_3$, $\alpha_4$, $\alpha_5$, $\alpha_6$, $\alpha_7$, $\beta_2$, $\beta_3$ and $\beta_4$ is presented in the Sequence Listing provided herewith. It is recognized that some of the subunits may have ion transport function in the absence of additional subunits. For example, the $\alpha_7$ subunit is functional in the absence of any added beta subunit.

In certain embodiments, eukaryotic cells with heterologous human neuronal nicotinic AChRs are produced by introducing into the cell a first composition, which contains at least one RNA transcript that is translated in the cell into a subunit of a human neuronal nicotinic AChR. In preferred embodiments, the subunits that are translated include an alpha subunit of a human neuronal nicotinic AChR. More preferably, the composition that is introduced contains an RNA transcript which encodes an alpha subunit and also contains an RNA transcript which encodes a beta subunit of a human neuronal nicotinic AChR. RNA transcripts can be obtained from cells transfected with DNAs encoding human neuronal nicotinic acetylcholine receptor subunits or by in vitro transcription of subunit-encoding DNAs. Methods for in vitro transcription of cloned DNA and injection of the resulting mRNA into eukaryotic cells are well known in the art. Amphibian oocytes are particularly preferred for expression of in vitro transcripts of the human nNAChR DNA clones provided herein. See, for example, Dascal (1989) CRC Crit. Rev. Biochem. 22:317–387, for a review of the use of Xenopus oocytes to study ion channels.

Thus, stepwise introduction of DNA or RNA encoding one or more alpha and/or one or more beta subtypes into cells is possible. The resulting cells may be tested by the methods provided herein or known to those of skill in the art to detect functional AChR activity. Such testing will allow the identification of combinations of alpha and beta subunit subtypes that produce functional AChRs, as well as individual subunits that produce functional AChRs. It is recognized that some of the subunits may have ion transport function in the absence of additional subunits, while others require a combination of two or more subunits in order to display ion transport function. For example, the $\alpha_7$ subunit is functional in the absence of any added beta subunit. Furthermore, some of the subunits may not form functional nAChRs alone or in combination, but instead may modulate the properties of other nAChR subunit combinations.

As used herein, activity of a human neuronal nicotinic AChR refers to any activity characteristic of an NAChR. Such activity can typically be measured by one or more in vitro methods, and frequently corresponds to an in vivo activity of a human neuronal nicotinic AChR. Such activity may be measured by any method known to those of skill in the art, such as, for example, measuring the amount of current which flows through the recombinant channel in response to a stimulus.

Methods to determine the presence and/or activity of human neuronal nicotinic AChRs include assays that measure nicotine binding, $^{86}$Rb ion-flux, $Ca^{2+}$ influx, the electrophysiological response of cells, the electrophysiological response of oocytes transfected with RNA from the cells, and the like. In particular, methods are provided herein for the measurement or detection of an AChR-mediated response upon contact of cells containing the DNA or mRNA with a test compound.

As used herein, a recombinant or heterologous human neuronal nicotinic AChR refers to a receptor that contains one or more subunits encoded by heterologous DNA that has been introduced into and expressed in cells capable of expressing receptor protein. A recombinant human neuronal nicotinic AChR may also include subunits that are produced by DNA endogenous to the host cell. In certain embodiments, recombinant or heterologous human neuronal nicotinic AChR may contain only subunits that are encoded by heterologous DNA.

As used herein, heterologous or foreign DNA and RNA are used interchangeably and refer to DNA or RNA that does not occur naturally as part of the genome of the cell in which it is present or to DNA or RNA which is found in a location or locations in the genome that differ from that in which it occurs in nature. Typically, heterologous or foreign DNA and RNA refers to DNA or RNA that is not endogenous to the host cell and has been artificially introduced into the cell. Examples of heterologous DNA include DNA that encodes a human neuronal nicotinic AChR subunit, DNA that encodes RNA or proteins that mediate or alter expression of endogenous DNA by affecting transcription, translation, or other regulatable biochemical processes, and the like. The cell that expresses heterologous DNA may contain DNA encoding the same or different expression products. Heterologous DNA need not be expressed and may be integrated into the host cell genome or maintained episomally.

Recombinant receptors on recombinant eukaryotic cell surfaces may contain one or more subunits encoded by the DNA or mRNA encoding human neuronal nicotinic AChR subunits, or may contain a mixture of subunits encoded by the host cell and subunits encoded by heterologous DNA or MRNA. Recombinant receptors may be homogeneous or may be a mixture of subtypes. Mixtures of DNA or mRNA encoding receptors from various species, such as rats and humans, may also be introduced into the cells. Thus, a cell can be prepared that expresses recombinant receptors containing only $\alpha_3$ and $\beta_4$ subunits, or any other combination of alpha and beta subunits provided herein. For example, $\alpha_4$ and/or $\alpha_7$ subunits can be co-expressed with $\beta_2$ and/or $\beta_4$ receptor subunits; similarly, $\beta_4$ subunits can be co-expressed with $\alpha_2$, $\alpha_3$, $\alpha_4$, $\alpha_5$ and/or $\alpha_7$ receptor subunits. As noted previously, some of the nNAChR subunits may be capable of forming functional receptors in the absence of other subunits, thus co-expression is not always required to produce functional receptors.

As used herein, a functional neuronal nicotinic AChR is a receptor that exhibits an activity of neuronal nicotinic AChRs as assessed by any in vitro or in vivo assay disclosed herein or known to those of skill in the art. Possession of any such activity that may be assessed by any method known to those of skill in the art and provided herein is sufficient to designate a receptor as functional. Methods for detecting NAChR protein and/or activity include, for example, assays that measure nicotine binding, $^{86}$Rb ion-flux, $Ca^{2+}$ influx, the electrophysiological response of cells containing heterologous DNA or mRNA encoding one or more receptor subunit subtypes, and the like. Since all combinations of alpha and beta subunits may not form functional receptors, numerous combinations of alpha and beta subunits should be tested in order to fully characterize a particular subunit and cells which produce same. Thus, as used herein, "functional" with respect to a recombinant or heterologous human neuronal nicotinic AChR means that the receptor channel is able to provide for and regulate entry of human neuronal nicotinic AChR-permeable ions, such as, for example, $Na^+$, $K^+$, $Ca^{2+}$ or $Ba^{2+}$, in response to a stimulus and/or bind ligands with affinity for the receptor. Preferably such human neuronal nicotinic AChR activity is distinguishable, such as by electrophysiological, pharmacological and other means known to those of skill in the art, from any endogenous nicotinic AChR activity that may be produced by the host cell.

In accordance with a particular embodiment of the present invention, recombinant human neuronal nicotinic AChR-expressing mammalian cells or oocytes can be contacted with a test compound, and the modulating effect(s) thereof can then be evaluated by comparing the AChR-mediated response in the presence and absence of test compound, or by comparing the AChR-mediated response of test cells, or control cells (i.e., cells that do not express nNAChRs), to the presence of the compound.

As used herein, a compound or signal that "modulates the activity of a neuronal nicotinic AChR" refers to a compound or signal that alters the activity of NAChR so that activity of the NAChR is different in the presence of the compound or signal than in the absence of the compound or signal. In particular, such compounds or signals include agonists and antagonists. The term agonist refers to a substance or signal, such as ACh, that directly or indirectly activates receptor function; and the term antagonist refers to a substance that directly or indirectly interferes with receptor function. Typically, the effect of an antagonist is observed as a blocking of activation by an agonist. Antagonists include competitive and non-competitive antagonists. A competitive antagonist (or competitive blocker) interacts with or near the site specific for the agonist (e.g., ligand or neurotransmitter) for the same or closely situated site. A non-competitive antagonist or blocker inactivates the functioning of the receptor by interacting with a site other than the site that interacts with the agonist.

As understood by those of skill in the art, assay methods for identifying compounds that modulate human neuronal nicotinic AChR activity (e.g., agonists and antagonists) generally require comparison to a control. One type of a "control" cell or "control" culture is a cell or culture that is treated substantially the same as the cell or culture exposed to the test compound, except the control culture is not exposed to test compound. For example, in methods that use voltage clamp electrophysiological procedures, the same cell can be tested in the presence and absence of test compound, by merely changing the external solution bathing the cell. Another type of "control" cell or "control" culture may be a cell or a culture of cells which are identical to the transfected cells, except the cells employed for the control culture do not express functional human neuronal nicotinic AChRs. In this situation, the response of test cell to test compound is compared to the response (or lack of response) of receptor-negative (control) cell to test compound, when cells or cultures of each type of cell are exposed to substantially the same reaction conditions in the presence of compound being assayed.

The functional recombinant human neuronal nicotinic AChR includes at least an alpha subunit, or an alpha subunit and a beta subunit of a human neuronal nicotinic AChR. Eukaryotic cells expressing these subunits have been prepared by injection of RNA transcripts and by transfection of DNA. Such cells have exhibited nicotinic AChR activity attributable to human neuronal nicotinic AChRs that contain one or more of the heterologous human neuronal nicotinic AChR subunits. For example, Xenopus laevis oocytes that had been injected with in vitro transcripts of the DNA encoding human neuronal nicotinic AChR $\alpha_3$ and $\beta_4$ subunits exhibited AChR agonist induced currents; whereas cells that had been injected with transcripts of either the $\alpha_3$ or $\beta_4$ subunit alone did not. In addition, HEK 293 cells that had been co-transfected with DNA encoding human neuronal NAChR $\alpha_3$ and $\beta_4$ subunits exhibited AChR agonist-induced increases in intracellular calcium concentration, whereas control HEK 293 cells (i.e., cells that had not been transfected with $\alpha_3$- and $\beta_4$-encoding DNA) did not exhibit any AChR agonist-induced increases in intracellular calcium concentration.

With respect to measurement of the activity of functional heterologous human neuronal nicotinic AChRs, endogenous AChR activity and, if desired, activity of AChRs that contain a mixture of endogenous host cell subunits and heterologous subunits, should, if possible, be inhibited to a significant extent by chemical, pharmacological and electrophysiological means.

DEPOSITS

The deposited clones have been deposited at the American Type Culture Collection (ATCC), 10801 University Boulevard, Manassas, Va. 20110-2209, under the terms of the Budapest Treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of the Treaty and Regulations and otherwise in compliance with the patent laws and regulations of the United States of America and all other nations or international organizations in which this application, or an application claiming priority of this application, is filed or in which any patent granted on any such application is granted. In particular, upon issuance of a U.S. patent based on this or any application claiming priority to or incorporating this application by reference thereto, all restrictions upon availability of the deposited material will be irrevocably removed.

The invention will now be described in greater detail with reference to the following non-limiting examples.

EXAMPLE 1

Preparation of Constructs for the Expression of Recombinant Human Neuronal Nicotinic AChR Subunits Isolated cDNAs encoding human neuronal nicotinic AChR subunits were incorporated into vectors for use in expressing the subunits in mammalian host cells and for use in generating in vitro transcripts of the DNAs to be expressed in Xenopus oocytes. Several different vectors were utilized in preparing the constructs as follows.

A. Construct for Expression of a Human nNAChR $\alpha_3$ Subunit

Figure 1B:
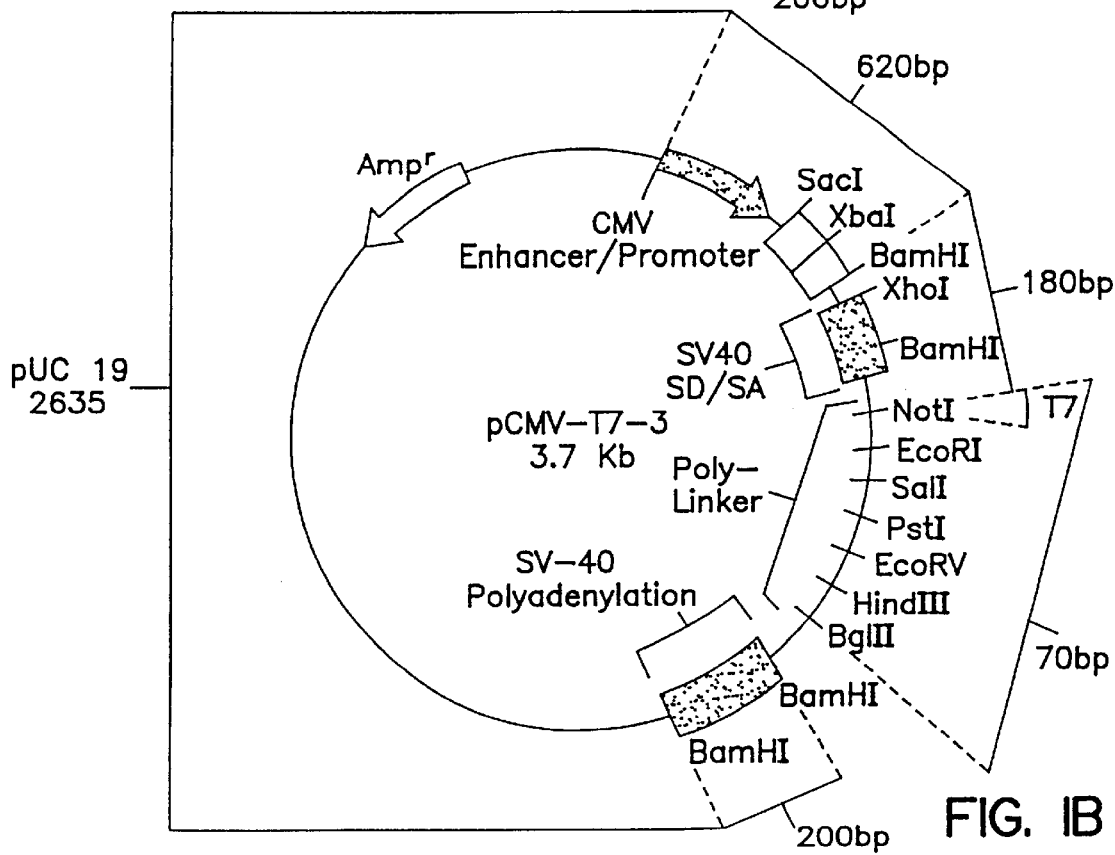

DNA encoding a human neuronal nicotinic AChR $\alpha_3$ subunit was subcloned into the pCMV-T7-2 general expression vector to create pCMV-KE$\alpha$3. Plasmid pCMV-T7-2 (see FIG. 1) is a pUC119-based vector that contains a CMV promoter/enhancer, SV40 splice donor/splice acceptor sites located immediately downstream of the promoter, a T7 bacteriophage RNA polymerase promoter positioned downstream of the SV40 splice sites, an SV40 polyadenylation signal downstream of the T7 promoter, and a polylinker between the T7 promoter and the polyadenylation signal. This vector thus contains all the regulatory elements required for expression of heterologous DNA in a mammalian host cell, wherein the heterologous DNA has been incorporated into the vector at the polylinker. In addition, because the T7 promoter is located just upstream of the polylinker, this plasmid can be used for synthesis of in vitro transcripts of heterologous DNA that has been subcloned into the vector at the polylinker. FIG. 1 also shows a restriction map of pCMV-T7-3. This plasmid is identical to pCMV-T7-2 except that the restriction sites in the polylinker are in the opposite order as compared to the order in which they occur in pCMV-T7-2.

A 1.7 kb SfiI (blunt-ended)/EcoRI DNA fragment containing nucleotides 27–1759 of SEQ ID No. 3 (i.e., the entire $\alpha_3$ subunit coding sequence plus 12 nucleotides of 5' untranslated sequence and 206 nucleotides of 3' untranslated sequence) was ligated to EcoRV/EcoRI-digested pCMV-T7-2 to generate pCMV-KE$\alpha$3. Plasmid pCMV-KE$\alpha$3 was used for expression of the $\alpha_3$ subunit in mammalian cells and for generating in vitro transcripts of the $\alpha_3$ subunit DNA.

B. Constructs for Expression of a Human nNAChR $\beta$ Subunit

A 1.9 kb EcoRI DNA fragment containing nucleotides 1–1915 of SEQ ID No. 11 (i.e., the entire $\alpha_4$ subunit coding sequence plus 86 nucleotides of 5' untranslated sequence and 332 nucleotides of 3' untranslated sequence) was ligated to EcoRI-digested pGEM7Zf(+) (Promega Catalog #P2251; Madison, Wis.). The resulting construct, KE$\beta$4.6/pGEM, contains the T7 bacteriophage RNA polymerase promoter in operative association with two tandem $\beta_4$ subunit DNA inserts (in the same orientation) and was used in generating in vitro transcripts of the DNA.

The same 1.9 kb EcoRI DNA fragment containing nucleotides 1–1915 of SEQ ID No. 11 was ligated as a single insert to EcoRI-digested pCMV-T7-3 to generate pCMV-KE$\beta$4. Plasmid pCMV-KE$\beta$4 was used for expression of the $\beta_4$ subunit in mammalian cells and for generating in vitro transcripts of the $\beta_4$ subunit DNA.

C. Constructs for Expression of a Human nNAChR $\alpha_7$ Subunit

Two pCMV-T7-2-based constructs were prepared for use in recombinant expression of a human neuronal nicotinic AChR $\alpha_7$ subunit. The first construct, pCMV-KE$\alpha$7.3, was prepared by ligating a 1.9 kb XhoI DNA fragment containing nucleotides 1–1876 of SEQ ID No. 7 (i.e., the entire $\alpha_7$ subunit coding sequence plus 72 nucleotides of 5' untranslated sequence and 295 nucleotides of 3' untranslated sequence) to SalI-digested pCMV-T7-3. The second construct, pCMV-KE$\alpha$7, was prepared by replacing the 5' untranslated sequence of the 1.9 kb XhoI $\alpha_7$ subunit DNA fragment described above with a consensus ribosome binding site (5'-GCCACC-3'; see Kozak (1987) Nucl. Acids Res. 15:8125–8148). The resulting modified fragment was ligated as a 1.8 kb BglII/XhoI fragment with BglII/SalI-digested pCMV-T7-2 to generate pCMV-KE$\alpha$7. Thus, in pCMV-KE$\alpha$7, the translation initiation codon of the coding sequence of the $\alpha_7$ subunit cDNA is preceded immediately by a consensus ribosome binding site.

D. Constructs for Expression of a Human nNAChR $\beta_2$ Subunit

DNA fragments encoding, portions of a human neuronal nicotinic AChR $\beta_2$ subunit were ligated together to generate a full-length $\beta_2$ subunit coding sequence contained in plasmid pIBI24 (International Biotechnologies, Inc. (IBI), New Haven, Conn.). The resulting construct, H$\beta$2.1F, contains nucleotides 1–2450 of SEQ ID No. 9 (i.e., the entire $\beta_2$ subunit coding sequence, plus 266 nucleotides of 5' untranslated sequence and 675 nucleotides of 3' untranslated sequence) in operative association with the T7 promoter. Therefore, H$\beta$2.1F was used for synthesis of in vitro transcripts from the $\beta_2$ subunit DNA.

Since the 5' untranslated sequence of the $\beta_2$ subunit DNA contains a potential alternative translation initiation codon (ATG) beginning 11 nucleotides upstream (nucleotides 256–258 in SEQ ID No. 9) of the correct translation initiation codon (nucleotides 267–269 in SEQ ID No. 9), and because the use of the upstream ATG sequence to initiate translation of the $\beta_2$ DNA would result in the generation of an inoperative peptide (because the upstream ATG is not in the correct reading frame), an additional $\beta_2$-encoding construct was prepared as follows. A 2.2 kb KspI/EcoRI DNA fragment containing nucleotides 262–2450 of SEQ ID No. 9 was ligated to pCMV-T7-2 in operative association with the T7 promoter of the plasmid to create pCMV-KE$\beta$2. The $\beta_2$ subunit DNA contained in pCMV-KE$\beta$2 retains only 5 nucleotides of 5' untranslated sequence upstream of the correct translation initiation codon.

EXAMPLE 2

Expression of Recombinant Human Nicotinic AChR in Oocytes

Xenopus oocytes were injected with in vitro transcripts prepared from constructs containing DNA encoding $\alpha_3$, $\alpha_7$, $\beta_2$ and $\alpha_4$ subunits. Electrophysiological measurements of the oocyte transmembrane currents were made using the two-electrode voltage clamp technique (see, e.g., Stuhmer (1992) *Meth. Enzymol.* 207:319–339).

1. Preparation of In Vitro Transcripts

Recombinant capped transcripts of pCMV-KE$\alpha$3, pCMV-KE$\beta$2, KE$\beta$4.6/pGEM and pCMV-KE$\beta$4 are synthesized from linearized plasmids using the mCAP RNA Capping Kit (Cat. #200350 from Stratagene, Inc., La Jolla, Calif.). Recombinant capped transcripts of pCMV-KE$\alpha$7, pCMV-KE$\alpha$7.3 and H$\beta$2.1F are synthesized from linearized plasmids using the MEGAscript T7 in vitro transcription kit according to the capped transcript protocol provided by the manufacturer (Catalog #1334 from AMBION, Inc., Austin, Tex.). Alternatively, recombinant capped transcripts of pcDNA3-KE$\alpha$6RBS and pcDNA3-KB$\beta$3RBS are synthesized from linearized plasmids using the mMessage and mMachine in vitro transcription kit according to the capped transcript protocol provided by the manufacturer (Catalog 1344 from AMBION, Inc., Austin, Tex.). The mass of each synthesized transcript is determined by UV absorbance and the integrity of each transcript was determined by electrophoresis through an agarose gel.

2. Electrophysiology

Xenopus oocytes were injected with either 12.5, 50 or 125 ng of human nicotinic AChR subunit transcript per oocyte. The preparation and injection of oocytes were carried out as described by Dascal (1987) in *Crit. Rev. Biochem.* 22:317–387. Two-to-six days following mRNA injection, the oocytes were examined using the two-electrode voltage clamp technique. The cells were bathed in Ringer's solution (115 mM NaCl, 2.5 mM KCl, 1.8 mM CaCl$_2$, 10 mM HEPES, pH 7.3) containing 1 $\mu$M atropine with or without 100 $\mu$M d-tubocurarine. Cells were voltage-clamped at –60 to –80 mV. Data were acquired with Axotape software at 2–5 Hz. The agonists acetylcholine (ACh), nicotine, and cytisine were added at concentrations ranging from 0.1 $\mu$M to 100 $\mu$M. The results of electrophysiological analyses of the oocytes are summarized in Table 1.

TABLE 1

| Template, ng RNA injected | Number of oocytes responding | Agonists | Current Amplitude |
|---|---|---|---|
| pCMV-KE$\alpha$3, 12.5 ng | 0 of 8 | ACh, Nicotine | |
| KE$\beta$4.6/pGEM, 12.5 ng | 0 of 9 | ACh, Nicotine | |
| pCMV-KE$\alpha$3, 12.5 ng + KE$\beta$4.6/pGEM, 12.5 ng | 4 of 5 | ACh, Nicotine | 20–550 nA |
| pCMV-KE$\alpha$3, 12.5 ng + KE$\beta$4.6/pGEM, 12.5 ng | 3 of 4 | ACh, Cytisine, Nicotine | 20–300 nA |
| pCMV-KE$\alpha$3, 125 ng + and pCMV-KE$\beta$4, 125 ng | 5 of 5 | ACh, Nicotine, Cytisine | 200–500 nA |
| pCMV-KE$\alpha$3, 125 ng + pCMV-KE$\beta$4, 125 ng | 6 of 6 | ACh, Nicotine, Cytisine | 100–400 nA |
| pCMV-KE$\alpha$7.3, 125 ng | 3 of 15 | ACh | ~20 nA |
| pCMV-KE$\alpha$7, 125 ng | 11 of 11 | ACh | 20–250 nA |
| pCMV-KE$\alpha$, 12.5 ng + pCMV-KE$\beta$2, 12.5 ng | 2 of 9 | ACh, Nicotine | <10 nA |
| pCMV-KE$\alpha$3, 125 ng + pCMV-KE$\beta$2, 125 ng | 0 of 9 | ACh, Nicotine | |
| pCMV-KE$\alpha$3, 125 ng + H$\beta$2.1F, 125 ng | 13 of 16 | ACh (100 $\mu$M) ACh (300 $\mu$M) | ~20 nA ~80 nA | a. Oocytes Injected with $\alpha_3$ and/or $\beta_4$ Transcripts

Oocytes that had been injected with 12.5 ng of the $\alpha_3$ transcript or 12.5 ng of the $\alpha_4$ transcript did not respond to application of up to 100 $\mu$M ACh, nicotine or cytisine. Thus, it appears that these subunits do not form functional homomeric nicotinic AChR channels. By contrast, oocytes injected with 12.5 or 125 ng of the $\alpha_3$ transcript and 12.5 ng or 125 ng of the $\beta_4$ transcript exhibited detectable inward currents in response to ACh, nicotine, and cytisine at the tested concentrations (0.1 $\mu$M to 10 $\mu$M). Some differences in the kinetics of the responses to cytisine compared to nicotine and ACh were observed. The relative potency of the agonists appeared to be cytisine>ACh>nicotine, which differs from the results of similar studies of oocytes injected with transcripts of the rat nicotinic AChR $\alpha_3$ and $\beta_4$ subunits (see, for example, Luetje et al. (1991) *J. Neurosci.* 11:837–845).

The responses to ACh and nicotine were reproducibly blocked by d-tubocurarine. For example, complete blockage of the response to ACh was observed in the presence of 100 $\mu$M d-tubocurarine. The inhibition appeared to be reversible. The responses to ACh, nicotine and cytisine were also at least partially blocked by 100 nM mecamylamine.

The current response of $\alpha_3$-$\beta_4$-injected oocytes to 10 $\mu$M ACh was also examined in terms of membrane voltage. In these experiments, voltage steps were applied to the cells in the presence of ACh. The graph of current vs. voltage appeared typical of responses observed for Na$^+$, K$^+$-permeable channels. For example, the zero current level (reversal potential) is less than –40 mV. The contribution of Ca$^{++}$ flux to the total current can be ascertained by varying the calcium concentration in the external medium and taking multiple current measurements at different holding potentials around the reversal potential. Such studies indicate that the channel carrying the current generated in response to ACh treatment of $\alpha_3$-$\beta_4$-injected oocytes is permeable to Na$^+$, K$^+$ and Ca$^{++}$.

b. Oocytes Injected with $\alpha_7$ Subunit Transcripts

As described in Example 1, two constructs were prepared for use in expressing the human neuronal nicotinic AChR $\alpha_7$ subunit. Plasmid pCMV-KE$\alpha$7.3 contains the $\alpha_7$ subunit coding sequence with 72 nucleotides of 5' untranslated sequence upstream of the translation initiation codon. Plasmid pCMV-KE$\alpha$7 contains the $\alpha_7$ subunit coding sequence devoid of any 5' untranslated sequence and further contains a consensus ribosome binding site immediately upstream of the coding sequence.

Oocytes injected with 125 ng of $\alpha_7$ transcript synthesized from pCMV-KE$\alpha$7 displayed inward currents in response to 10 or 100 $\mu$M ACh. This response was blocked by 100 $\mu$M d-tubocurarine.

Oocytes injected with 125 ng of $\alpha_7$ transcript synthesized from pCMV-KE$\alpha$7.3 exhibited ACh-induced currents that were substantially weaker than those of oocytes injected with $\alpha_7$ transcript synthesized from pCMV-KE$\alpha$7. These results indicate that human neuronal nicotinic AChR $\alpha_7$ subunit transcripts generated from $\alpha_7$ subunit DNA containing a ribosome binding site in place of 5' untranslated sequence may be preferable for expression of the $\alpha_7$ receptor in oocytes.

c. Oocytes Injected with $\alpha_3$ and $\beta_2$ Subunit Transcripts

As described in Example 1, two constructs were prepared for use in expressing the human neuronal nicotinic AChR $\beta_2$ subunit. Plasmid H$\beta$2.1F contains the $\beta_2$ subunit coding sequence with 266 nucleotides of 5' untranslated sequence upstream of the translation initiation codon. Plasmid pCMV-KE$\beta$2 contains the $\beta_2$ subunit coding sequence and only 5 nucleotides of 5' untranslated sequence upstream of the translation initiation codon.

Oocytes injected with transcripts of pCMV-KE$\alpha$3 and pCMV-KE$\beta$2 displayed no current in response to nicotinic AChR agonists. In contrast, oocytes injected with transcripts of pCMV-KE$\alpha$3 and H$\beta$2.1F displayed ~20 nA inward currents in response to 100 $\mu$M ACh and 80 nA inward currents in response to 300 $\mu$M ACh. The current response was blocked by 100 $\mu$M d-tubocurarine. These results indicate that human neuronal nicotinic AChR $\beta_2$ subunit transcripts generated from $\beta_2$ subunit DNA containing 5' untranslated sequence may be preferable to transcripts generated from $\beta_2$ DNA containing only a small portion of 5' untranslated sequence for expression of the $\alpha_3\beta_2$ receptors in oocytes.

EXAMPLE 3

Recombinant Expression of Human nNAChR Subunits in Mammalian Cells

Human embryonic kidney (HEK) 293 cells were transiently and stably transfected with DNA encoding human neuronal nicotinic AChR $\alpha_3$ and $\beta_4$, or $\alpha_7$ subunits. Transient transfectants were analyzed for expression of nicotinic AChR using various assays, e.g., electrophysiological methods, Ca$^{2+}$-sensitive fluorescent indicator-based assays and [$^{125}$I]-$\alpha$-bungarotoxin-binding assays.

1. Transient Transfection of HEK Cells

Two transient transfections were performed. In one transfection, HEK cells were transiently co-transfected with DNA encoding $\alpha_3$ (plasmid pCMV-KE$\alpha$3) and $\beta_4$ (plasmid pCMV-KE$\beta$4) subunits. In the other transfection, HEK cells were transiently transfected with DNA encoding the $\alpha_7$ subunit (plasmid pCMV-KE$\alpha$7). In both transfections, ~2× 10$^6$ HEK cells were transiently transfected with 18 $\mu$g of the indicated plasmid(s) according to standard CaPO$_4$ transfection procedures [Wigler et al. (1979) Proc. Natl. Acad. Sci. USA 76:1373–1376]. In addition, 2 $\mu$g of plasmid pCMV$\beta$gal (Clontech Laboratories, Palo Alto, Calif.), which contains the Escherichia coli $\beta$-galactosidase gene fused to the CMV promoter, were co-transfected as a reporter gene for monitoring the efficiency of transfection. The transfectants were analyzed for $\beta$-galactosidase expression by measurement of $\beta$-galactosidase activity [Miller (1972) Experiments in Molecular Genetics, pp.352–355, Cold Spring Harbor Press]. Transfectants can also be analyzed for $\beta$-galactosidase expression by direct staining of the product of a reaction involving $\beta$-galactosidase and the X-gal substrate [Jones (1986) EMBO 5:3133–3142].

The efficiency of transfection of HEK cells with pCMV-KE$\alpha$3/pCMV-KE$\beta$4 was typical of standard efficiencies, whereas the efficiency of transfection of HEK cells with pCMV-KE$\alpha$7 was below standard levels.

2. Stable Transfection of HEK Cells

HEK cells were transfected using the calcium phosphate transfection procedure [Current Protocols in Molecular Biology, Vol. 1, Wiley Inter-Science, Supplement 14, Unit 9.1.1–9.1.9 (1990)]. Ten-cm plates, each containing one-to-two million HEK cells were transfected with 1 ml of DNA/calcium phosphate precipitate containing 9.5 $\mu$g pCMV-KE$\alpha$3, 9.5 $\mu$g pCMV-KE$\beta$4 and 1 $\mu$g pSV2neo (as a selectable marker). After 14 days of growth in media containing 1 $\mu$g/ml G418, colonies had formed and were individually isolated by using cloning cylinders. The isolates were subjected to limiting dilution and screened to identify those that expressed the highest level of nicotinic AChR, as described below.

3. Analysis of Transfectants a. Fluorescent Indicator-based Assays

Activation of the ligand-gated nicotinic AChR by agonists leads to an influx of cations, including Ca$^{++}$, through the receptor channel. Ca$^{++}$ entry into the cell through the channel can induce release of calcium contained in intracellular stores. Monovalent cation entry into the cell through the channel can also result in an increase in cytoplasmic Ca$^{++}$ levels through depolarization of the membrane and subsequent activation of voltage-dependent calcium channels. Therefore, methods of detecting transient increases in intracellular calcium concentration can be applied to the analysis of functional nicotinic AChR expression. One method for measuring intracellular calcium levels relies on calcium-sensitive fluorescent indicators.

Calcium-sensitive indicators, such as fluo-3 (Catalog No. F-1241, Molecular Probes, Inc., Eugene, Oreg.), are available as acetoxymethyl esters which are membrane permeable. When the acetoxymethyl ester form of the indicator enters a cell, the ester group is removed by cytosolic esterases, thereby trapping the free indicator in the cytosol. Interaction of the free indicator with calcium results in increased fluorescence of the indicator; therefore, an increase in the intracellular Ca$^{2+}$ concentration of cells containing the indicator can be expressed directly as an increase in fluorescence. An automated fluorescence detection system for assaying nicotinic AChR has been described in commonly assigned pending U.S. patent application Ser. No. 07/812,254 and corresponding PCT Patent Application Ser. No. US92/11090.

HEK cells that were transiently or stably co-transfected with DNA encoding $\alpha_3$ and $\beta_4$ subunits were analyzed for expression of functional recombinant nicotinic AChR using the automated fluorescent indicator-based assay. The assay procedure was as follows.

Untransfected HEK cells (or HEK cells transfected with pCMV-T7-2) and HEK cells that had been co-transfected with pCMV-KEα3 and pCMV-KEβ4 were plated in the wells of a 96-well microtiter dish and loaded with fluo-3 by incubation for 2 hours at 20° C. in a medium containing 20 μM fluo-3, 0.2% Pluronic F-127 in HBS (125 mM NaCl, 5 mM KCl, 1.8 mM $CaCl_2$, 0.62 mM $MgSO_4$, 6 mM glucose, 20 mM HEPES, pH 7.4). The cells were then washed with assay buffer (i.e., HBS). The antagonist d-tubocurarine was added to some of the wells at a final concentration of 10 μM. The microtiter dish was then placed into a fluorescence plate reader and the basal fluorescence of each well was measured and recorded before addition of 200 μM nicotine to the wells. The fluorescence of the wells was monitored repeatedly during a period of approximately 60 seconds following addition of nicotine.

The fluorescence of the untransfected HEK cells (or HEK cells transfected with pCMV-T7-2) did not change after addition of nicotine. In contrast, the fluorescence of the co-transfected cells, in the absence of d-tubocurarine, increased dramatically after addition of nicotine to the wells. This nicotine-stimulated increase in fluorescence was not observed in co-transfected cells that had been exposed to the antagonist d-tubocurarine. These results demonstrate that the co-transfected cells express functional recombinant AChR that are activated by nicotine and blocked by d-tubocurarine.

b. α-Bungarotoxin binding assays

HEK293 cells transiently transfected with pCMV-KEα7 were analyzed for $[^{125}I]$-α-bungarotoxin (BgTx) binding. Both whole transfected cells and membranes prepared from transfected cells were examined in these assays. Rat brain membranes were included in the assays as a positive control.

Rat brain membranes were prepared according to the method of Hampson et al. (1987) J. Neurochem 49:1209. Membranes were prepared from the HEK cells transfected with pCMV-KEα7 and HEK cells transiently transfected with plasmid pUC19 only (negative control) according to the method of Perez-Reyes et al. (1989) Nature 340:233. Whole transfected and negative control cells were obtained by spraying the tissue culture plates with phosphate-buffered saline containing 0.1% (w/v) BSA. The cells were then centrifuged at low speed, washed once, resuspended in assay buffer (118 mM NaCl, 4.8 mM KCl, 2.5 mM $CaCl_2$, 1.2 mM $MgSO_4$, 20 mM HEPES, 0.1% (w/v)BSA, 0.05% (w/v) bacitracin and 0.5 mM PMSF, pH 7.5) and counted.

Specific binding of $[^{125}I]$-α-BgTx to rat brain membranes was determined essentially as described by Marks et al. (1982) Molec. Pharmacol. 22:554–564, with several modifications. The membranes were washed twice in assay buffer. The assay was carried out in 12×75 mm polypropylene test tubes in a total volume of 0.5 ml assay buffer. The membranes were incubated with 10 nM $[^{125}I]$-α-BgTx (New England Nuclear, Boston, Mass.) for one hour at 37° C. The assay mixtures were then centrifuged at 2300×g for 10 minutes at 4° C. The supernatant was decanted and the pellets were washed twice with 2 ml aliquots of ice-cold assay buffer. The supernatants were decanted again and the radioactivity of the pellets was measured in a γ-counter. Non-specific binding was determined in the presence of 1 μM unlabeled α-BgTx. Specific binding was determined by subtracting nonspecific binding from total binding. Specific binding of $[^{125}I]$-α-BgTx to membranes prepared from transfected and negative control cells was determined as described for determining specific binding to rat brain membranes except that the assay buffer did not contain BSA, bacitracin and PMSF. Specific binding of $[^{125}I]$-α-BgTx to transfected and negative control whole cells was determined basically as described for determining specific binding to rat brain membranes.

$[^{125}I]$-α-BgTx binding was evaluated as a function of membrane concentration and as a function of incubation time. [125I]-α-BgTx binding to rat brain membranes increased in a linear fashion with increasing amounts of membrane (ranging between 25–500 μg). The overall signal-to-noise ratio of binding (i.e., ratio of total binding to non-specific binding) was 3:1. Although some binding of $[^{125}I]$-α-BgTx to transfected cell membranes was detected, it was mostly non-specific binding and did not increase with increasing amounts of membrane. $[^{125}]$-α-BgTx binding to the transfectants and negative control cells appeared to be similar.

To monitor $[^{125}I]$-α-BgTx binding to rat brain membranes and whole transfected and negative control cells, 300 αg of membrane or 500,000 cells were incubated with 1 nM or 10 nM $[^{125}I]$-α-BgTx, respectively, at 37° C. for various times ranging from 0–350 min. Aliquots of assay mixture were transferred to 1.5 ml microfuge tubes at various times and centrifuged. The pellets were washed twice with assay buffer. $[^{125}I]$-α-BgTx binding to rat brain membranes increased with time and was maximal after three hours. The binding profiles of the transfected and negative control cells were the same and differed from that of rat brain membranes.

EXAMPLE 4

Characterization of Cell Lines Expressing nNAChRs

Recombinant cell lines generated by transfection with DNA encoding human neuronal nicotinic A ChRs, such as those described in Example 3, can be further characterized using one or more of the following methods.

A. Northern or Slot Blot Analysis for Expression of α- and/or β-subunit Encoding Messages Total RNA is isolated from ~1×10$^7$ cells and 10–15 μg of RNA from each cell type is used for Northern or slot blot hybridization analysis. The inserts from human neuronal NAChR-encoding plasmids can be nick-translated and used as probe. In addition, the β-actin gene sequence (Cleveland et al. (1980) Cell 20:95–105) can be nick-translated and used as a control probe on duplicate filters to confirm the presence or absence of RNA on each blot and to provide a rough standard for use in quantitating differences in α- or β-specific mRNA levels between cell lines. Typical Northern and slot blot hybridization and wash conditions are as follows:

hybridization in 5×SSPE, 5×Denhardt's solution, 50% formamide, at 42° C. followed by washing in 0.2× SSPE, 0.1% SDS, at 65° C.

B. Nicotine-binding Assay

Cell lines generated by transfection with human neuronal nicotinic AChR α- or α- and β-subunit-encoding DNA can be analyzed for their ability to bind nicotine, for example, as compared to control cell lines: neuronally-derived cell lines PC12 (Boulter et al., (1986), supra; ATCC #CRL1721) and IMR32 (Clementi et al. (1986); Int. J. Neurochem. 47:291–297; ATCC #CCL127), and muscle-derived cell line BC3H1 (Patrick, et al., (1977); J. Biol. Chem. 252:2143–2153). Negative control cells (i.e., host cells from which the transfectants were prepared) are also included in the assay. The assay is conducted as follows:

Just prior to being assayed, transfected cells are removed from plates by scraping. Positive control cells used are PC12, BC3H1, and IMR32 (which had been starved for fresh media for seven days). Control cell lines are removed by rinsing in 37° C. assay buffer (50 mM Tris/HCl, 1 mM MgCl$_2$, 2 mM CaCl$_2$, 120 mM NaCl, 3 mM EDTA, 2 mg/ml BSA and 0.1% aprotinin at pH7.4). The cells are washed and resuspended to a concentration of 1×10$^6$/250 µl. To each plastic assay tube is added 250 µl of the cell solution, 15 nM $^3$H-nicotine, with or without 1 mM unlabeled nicotine, and assay buffer to make a final volume of 500 µl. The assays for the transfected cell lines are incubated for 30 min at room temperature; the assays of the positive control cells are incubated for 2 min at 1° C. After the appropriate incubation time, 450 µl aliquots of assay volume are filtered through Whatman GF/C glass fiber filters which has been pretreated by incubation in 0.05% polyethyleneimine for 24 hours at 4° C. The filters are then washed twice, with 4 ml each wash, with ice cold assay buffer. After washing, the filters are dried, added to vials containing 5 ml scintillation fluid and radioactivity is measured.

C. $^{86}$Rb ion-flux Assay

The ability of nicotine or nicotine agonists and antagonists to mediate the influx of $^{86}$Rb into transfected and control cells has been found to provide an indication of the presence of functional AChRs on the cell surface. The $^{86}$Rb ion-flux assay is conducted as follows:

1. The night before the experiment, cells are plated at 2×10$^6$ per well (i.e., 2 ml per well) in a 6-well polylysine-coated plate.
2. The culture medium is decanted and the plate washed with 2 ml of assay buffer (50 mM HEPES, 260 mM sucrose, 5.4 mM KCl, 1.8 mM CaCl$_2$, 0.8 mM MgSO$_4$, 5.5. mM glucose) at room temperature.
3. The assay buffer is decanted and 1 ml of assay buffer, containing 3 µCi/ml $^{86}$Rb, with 5 mM ouabain and agonist or antagonist in a concentration to effect a maximum response, is added.
4. The plate is incubated on ice at 1° C. for 4 min.
5. The buffer is decanted into a waste container and each well was washed with 3 ml of assay buffer, followed by two washes of 2 ml each.
6. The cells are lysed with 2×0.5 ml of 0.2% SDS per well and transferred to a scintillation vial containing 5 ml of scintillation fluid.
7. The radioactivity contained in each vial is measured and the data calculated.

Positive control cells provided the following data in this assay:

|  | PC12 | | IMR32 | |
| --- | --- | --- | --- | --- |
|  | EC$_{50}$ | Maximum response | EC$_{50}$ | Maximum response |
| Agonist | | | | |
| nicotine | 52 µM | 2.1X$^a$ | 18 µM | 7.7X$^a$ |
| CCh* | 35 µM | 3.3X$^b$ | 230 µM | 7.6X$^c$ |
| cytisine | 57 µM | 3.6X$^d$ | 14 µM | 10X$^e$ |
| Antagonist | | | | |
| d-tubocurarine | 0.81 µM | | 2.5 µM | |
| mecamylamine | 0.42 µM | | 0.11 µM | |
| hexamethonium | nd$^f$ | | 22 µM | |
| atropine | 12.5 µM | | 43 µM | |

*CCh = carbamylcholine
$^a$200 µM nicotine
$^b$300 µM CCh
$^c$3 mM CCh
$^d$1 mM cytisine
$^e$100 µM cytisine
$^f$nd = not determined D. Electrophysiological Analysis of Mammalian Cells Transfected with Human Neuronal Nicotinic AChR Subunit-encodin DNA Electrophysiological measurements may be used to assess the activity of recombinant receptors or to assess the ability of a test compound to potentiate, antagonize or otherwise modulate the magnitude and duration of the flow of cations through the ligand-gated recombinant AChR. The function of the expressed neuronal AChR can be assessed by a variety of electrophysiological techniques, including two-electrode voltage clamp and patch clamp methods. The cation-conducting channel intrinsic to the AChR opens in response to acetylcholine (ACh) or other nicotinic cholinergic agonists, permitting the flow of transmembrane current carried predominantly by sodium and potassium ions under physiological conditions. This current can be monitored directly by voltage clamp techniques. In preferred embodiments, transfected mammalian cells or injected oocytes are analyzed electrophysiologically for the presence of AChR agonist-dependent currents.

While the invention has been described in detail with reference to certain preferred embodiments thereof, it will be understood that modifications and variations are within the spirit and scope of that which is described and claimed.

SUMMARY OF SEQUENCES

Sequence ID No. 1 is a nucleotide sequence encoding an α$_2$ subunit of human neuronal nicotinic acetylcholine receptor, and the deduced amino acid sequence thereof.

Sequence ID No. 2 is the amino acid sequence of the α$_2$ subunit of human neuronal nicotinic acetylcholine receptor set forth in Sequence ID No. 1.

Sequence ID No. 3 is a nucleotide sequence encoding an 3 subunit of human neuronal nicotinic acetylcholine receptor, and the deduced amino acid sequence thereof.

Sequence ID No. 4 is the amino acid sequence of the α$_3$ subunit of human neuronal nicotinic acetylcholine receptor set forth in Sequence ID No. 3.

Sequence ID No. 5 is a nucleotide sequence encoding an α$_4$ subunit of a human neuronal nicotinic acetylcholine receptor, and the deduced amino acid sequence thereof.

Sequence ID No. 6 is the amino acid sequence of the α$_4$ subunit of a human neuronal nicotinic acetylcholine receptor set forth in Sequence ID No. 5.

Sequence ID No. 7 is a nucleotide sequence encoding an α$_5$ subunit of human neuronal nicotinic acetylcholine receptor, and the deduced amino acid sequence thereof.

Sequence ID No. 8 is the amino acid sequence of the α$_5$ subunit of human neuronal nicotinic acetylcholine receptor set forth in Sequence ID No. 7.

Sequence ID No. 9 is a nucleotide sequence encoding an α₆ subunit of human neuronal nicotinic acetylcholine receptor, and the deduced amino acid sequence thereof.

Sequence ID No. 10 is the amino acid sequence of the α₆ subunit of human neuronal nicotinic acetylcholine receptor set forth in Sequence ID No. 9.

Sequence ID No. 11 is a nucleotide sequence encoding an α₇ subunit of human neuronal nicotinic acetylcholine receptor, and the deduced amino acid sequence thereof.

Sequence ID No. 12 is the amino acid sequence of the α₇ subunit of human neuronal nicotinic acetylcholine receptor set forth in Sequence ID No. 11.

Sequence ID No. 13 is a nucleotide sequence encoding a β₂ subunit of human neuronal nicotinic acetylcholine receptor, and the deduced amino acid sequence thereof.

Sequence ID No. 14 is the amino acid sequence of the β₂ subunit of human neuronal nicotinic acetylcholine receptor set forth in Sequence ID No. 13.

Sequence ID No. 15 is a nucleotide sequence encoding a β₃ subunit of human neuronal nicotinic acetylcholine receptor, and the deduced amino acid sequence thereof.

Sequence ID No. 16 is the amino acid sequence of the β₃ subunit of human neuronal nicotinic acetylcholine receptor set forth in Sequence ID No. 15.

Sequence ID No. 17 is a nucleotide sequence encoding β₄ subunit of human neuronal nicotinic acetylcholine receptor, and the deduced amino acid sequence thereof.

Sequence ID No. 18 is the amino acid sequence of the β₄ subunit of human neuronal nicotinic acetylcholine receptor set forth in Sequence ID No. 17.

That which is claimed:

1. A method for identifying compounds that are antagonists or agonists of human neuronal nicotinic acetylcholine receptors (nNAChRs), said method comprising:
   a) contacting recombinant cells with a test compound, wherein:
      the recombinant cells are produced by transfection with nucleic acid encoding at least one human nNAChR subunit;
      wherein the at least one subunit is an $\alpha_2$ subunit;
      the recombinant cells express an nNAChR comprising at least one human subunit encoded by the transfected nucleic acid; and
      the expressed nNAChR comprises at least one nNAChR $\alpha$ subunit; and
   b) measuring ion flux, the electrophysiological response of the cells, or binding of the test compound to the nNAChR, whereby agonist or antagonists of the nNAChR are identified, wherein;
      the $\alpha_2$ subunit comprises a sequence of amino acids having more than 95% identity with amino acid sequence set forth in SEQ ID No.2; or
      the $\alpha_2$ subunit is encoded by a sequence of nucleotides that hybridizes under conditions of high stringency with the complement of nucleotides 166–1755 set forth in SEQ ID No. 1 or shares at least about 90% identity to nucleotides 166–1755 in SEQ ID No: 1; or
      the $\alpha_2$ subunit is encoded by the nucleotides of 166–1755 of SEQ ID No. 1.

2. The method of claim 1, wherein the cells further comprise nucleic acid encoding a $\beta_2$ subunit that comprises the sequence of amino acids as set forth in SEQ ID NO:14.

3. The method of claim 1, wherein the cells further comprise nucleic acid encoding $\beta_3$ subunit that comprises a sequence of amino acids encoded by a sequence of nucleotides that hybridizes along its full length under conditions of high stringency to the entire coding sequence of nucleotides set forth in SEQ ID No. 15, or to the full length of a sequence of nucleotides encoding the amino acid sequence set forth in SEQ ID No. 16.

4. The method of claim 3, wherein said $\beta_3$ subunit comprises the sequence of amino acids as set forth in SEQ ID NO:16.

5. The method according to claim 3, wherein the $\beta_3$ subunit is encoded by a nucleic acid comprising the sequence of nucleotides set forth in SEQ ID No. 15.

6. The method according to claim 3, wherein the $\beta_3$ subunit comprises a sequence of amino acids encoded by a nucleic acid that hybridizes along its full length under conditions of high stringency to the coding sequence in the sequence of nucleotides set forth in SEQ ID No. 15.

7. The method according to claim 3, wherein the $\beta_3$ subunit comprises a sequence of amino acids encoded by a nucleic acid that hybridizes along its full length under conditions of high stringency to the full length of the sequence of nucleotides set forth in SEQ ID No. 15.

8. The method according to claim 3, wherein the $\beta_3$ subunit comprises a sequence of amino acids as set forth in SEQ ID No. 16.

9. The method according to claim 3, wherein the $\beta_3$ subunit comprises a sequence of amino acids encoded by the sequence of nucleotides as set forth in SEQ ID No. 15.

10. The method of claim 1, wherein the cells further comprise nucleic acid encoding $\beta_4$ subunit that comprises a sequence of amino acids encoded by a sequence of nucleotides that hybridizes along its full length under conditions of high stringency to the entire coding sequence of nucleotides set forth in SEQ ID No. 17, or to the full length of sequence of nucleotides encoding the amino acid sequence set forth in SEQ ID NO. 18.

11. The method of claim 10, wherein said $\beta_4$ subunit comprises the sequence of amino acids as set forth in SEQ ID NO:18.

12. The method according to claim 10, wherein the $\beta_4$ subunit is encoded by a nucleic acid comprising the sequence of nucleotides set forth in SEQ ID No. 17.

13. The method according to claim 10, wherein the $\beta_4$ subunit comprises a sequence of amino acids encoded by a nucleic acid that hybridizes along its full length under conditions of high stringency to the coding sequence in the sequence of nucleotides set forth in SEQ ID No. 17.

14. The method according to claim 10, wherein the $\beta_4$ subunit comprises a sequence of amino acids encoded by a nucleic acid that hybridizes along its full length under conditions of high stringency to the full length of the sequence of nucleotides set forth in SEQ ID No. 17.

15. The method according to claim 10, wherein the $\beta_4$ subunit comprises a sequence of amino acids as set forth in SEQ ID No. 18.

16. The method according to claim 10, wherein the $\beta_4$ subunit comprises a sequence of amino acids encoded by the sequence of nucleotides as set forth in SEQ ID No. 17.

17. The method of claim 1, wherein the recombinant cells are mammalian cells yeast cells or amphibian oocytes.

18. The method of claim 1, wherein:
the alteration in ion flux or the electrophysiological response of the cells is detected by comparing the measurements with measurements using control cells; and
the control cells are cells that do not express nNAChRs.

19. The method of claim 18, wherein ion flux of the cells is detected by $^{86}$Rb ion-flux, $Ca^{2+}$ influx, or electrophysiological response.

20. The method of claim 1, wherein:
the alteration in ion flux or the electrophysiological response of the cells is detected by comparing the measurements with measurements pads using control compounds; and
the control compounds are known agonists or antagonists of human nNAChRs.

21. The method of claim 1, wherein prior to or simultaneously with contacting the cells with a test compound the cells are contacted with a known nNAChR agonist.

22. The method of claim 21 that is a binding assay.

23. The method of claim 21, wherein the agonist is acetylcholine (ACh), nicotine, or cytisine.

24. The method of claim 21 that measures ion flux or the electrophysiological response of the cells.

25. The method of claim 1, wherein prior to or simultaneously with contacting the cells with a test compound the cells are contacted with a known nNAChR antagonist.

26. The method of claim 25 that is a binding assay.

27. The method of claim 25 that measures ion flux or the electrophysiological response of the cells.

28. The method of claim 1, wherein which is detected, wherein:
the recombinant cells further comprise a DNA encoding a reporter gene operatively linked to DNA encoding a transcriptional control element wherein the activity of the transcriptional control element is regulated by the human neuronal nicotinic acetylcholine receptor;
the reporter gene encodes a detectable gene product, wherein the detectable product is selected from the group consisting of mRNA and a polypeptide; and
the interaction of the test compound with the nNAChRs is measured by detecting the gene product encoded by the reporter gene.

29. The method of claim 1, wherein the cells further comprise nucleic acid encoding a $\beta_2$ subunit that comprises amino acids encoded by the DNA in a plasmid having all of the identifying characteristics of the plasmid depositeds ATCC No. 68279.

30. The method of claim 1, wherein the nucleic acid is DNA.

31. The method of claim 30, wherein the recombinant cells are mammalia cells.

32. The method of claim 1, wherein the nucleic acid is mRNA.

33. The method of claim 32, wherein the recombinant cells are amphibian oocytes.

34. The method according to claim 1, wherein the $\alpha_2$ subunit comprises a sequence of amino acids having more than 95% identity with amino acid sequence set forth in SEQ ID No. 2.

35. The method according to claim 1, wherein the α2 subunit is encoded by a sequence of nucleotides that hybridizes under conditions of high stringency with the complement of nucleotides 166–1755 set forth in SEQ ID No. 1 or shares at least about 90% identity to nucleotides 166–1755 in SEQ ID No: 1.

36. The method according to claim 1, wherein the $\alpha_2$ subunit is encoded by the nucleotides of 166–1755 of SEQ ID No. 1.

37. A method for identifying compounds that are antagonists or agonists of human neuronal nicotinic acetylcholine receptors (nNAChRs), said method comprising:
a) contacting recombinant cells with a test compound, wherein:
the recombinant cells comprise heterologous nucleic acid encoding at least one human nNAChR subunit;
express an nNAChR comprising at least one human subunit encoded by the heterologous nucleic acid wherein the at least one subunit is an $\alpha_2$ subunit; and
b) measuring ion flux, the electrophysiological response of the cells, or binding of the test compound to the nNAChR, whereby compounds that are agonists or antagonists of the nNAChR are identified, wherein said $\alpha_2$ subunit comprises the sequence of amino acids set forth in SEQ ID NO:2.

38. The method of claim 37, wherein the $\alpha_2$ subunit comprises amino acids encoded by the DNA in a plasmid having all of the identifying characteristics of the plasmid deposited as ATCC No. 68277.

39. The method of claim 37, wherein the cells further comprise nucleic acid encoding a $\beta_3$ subunit that comprises a sequence of amino acids encoded by a sequence of nucleotides that hybridizes along its full length under conditions of high stringency to the entire coding sequence of nucleotides set forth in SEQ ID No. 15, or to the full length of a sequence of nucleotides encoding the amino acid sequence set forth in SEQ ID No. 16.

40. The method of claim 37, wherein the cells further comprise nucleic acid encoding a $\beta_2$ subunit that comprises a sequence of amino acids encoded by a sequence of nucleotides that hybridizes along its full length under conditions of high stringency to the entire coding sequence of nucleotides set forth in SEQ ID No. 13, or to the full length of a sequence of nucleotides encoding the amino acid sequence set forth in SEQ ID No. 14.

41. The method of claim 37, wherein the cells further comprise nucleic acid encoding a $\beta_4$ subunit that comprises a sequence of amino acids encoded by a sequence of nucleotides that hybridizes along its full length under conditions of high stringency to the entire coding sequence of nucleotides set forth in SEQ ID No. 17, or to the full length of a sequence of nucleotides encoding the amino acid sequence set forth in SEQ ID No. 18.

42. The method of claim 37, wherein the recombinant cells are mammaliam cells, yeast cells or amphibian oocytes.

43. The method of claim 37, wherein:
the alteration in ion flux or the electrophysiological response of the cells is detected by comparing the measurements with measurements using control cells; and
control cells are cells that do not express nNAChRs.

44. The method of claim 37, wherein:
the alteration in ion flux or the electrophysiological response of the cells is detected by comparing the measurements with measurements using control compounds; and
control compounds are known agonists of antagonists of human nNAChRs.

45. The method of claim 37, wherein prior to or simultaneously with contacting the cells with a test compound the cells are contacted with a known nNAChR agonist.

46. The method of claim 37, wherein prior to or simultaneously with contacting the cells with a test compound the cells are contacted with a known nNAChR antagonist.

47. The method of claim 37, in which an agonist is detected, wherein:
the recombinant cells further comprise a DNA encoding a reporter gene operatively linked to DNA encoding a transcriptional control element wherein the activity of the transcriptional control element is regulated by the human neuronal nicotinic acetylcholine receptor;
the reporter gene encodes a detectable gene product, wherein the detectable product is selected from the group consisting of mRNA and a polypeptide; and
the interaction of the test compound with the nNAChRs is measured by detecting the gene product encoded by the reporter gene.

48. The method of claim 37, wherein: the nucleic acid is DNA.

49. The method of claim 37, wherein the nucleic acid is mRNA.

50. The method according to claim 37, wherein the $\alpha_2$ subunit comprises the sequence of amino acids set forth in SEQ ID NO:2.

51. A method for identifying compounds that are antagonists or agonists of human neuronal nicotinic acetylcholine receptors (nNAChRs), said method comprising:
a) contacting recombinant cells with a test compound, wherein:
the recombinant cells comprise heterologous nucleic acid encoding at least one human nNAChR subunit;
express an nNAChR comprising at least one human subunit encoded by the heterologous nucleic acid; and
the at least one human nNAChR subunit encoded by the heterologous nucleic acid is an $\alpha_3$ subunit; and
b) measuring ion flux, the electrophysiological response of the cells, or interaction of the test compound with the nNAChRs, whereby compounds that are agonists or antagonists of the nNAChR are identified, wherein:
the $\alpha_3$ subunit comprises a sequence of amino acids encoded by the $\alpha_3$-encoding nucleic acid that is isolated from a plasmid having all of the identifying characteristics of HnAChR$\alpha$3 deposited under ATCC Accession No. 68278; or
comprises the sequence of amino acids set forth in SEQ ID NO:4.

52. The method of claim 51, wherein said $\alpha_3$ subunit comprises the sequence of amino acids set forth in SEQ ID NO:4.

53. The method of claim 51, wherein the $\alpha_3$ subunit comprises amino acids encoded by the DNA in a plasmid having all of the identifying characteristics of the plasmid deposited as ATCC No. 68278.

54. The method of claim 51, wherein the cells further comprise nucleic acid encoding a $\beta_3$ subunit that comprises a sequence of amino acids encoded by a sequence of nucleotides that hybridizes along its full length under conditions of high stringency to the entire coding sequence of nucleotides set forth in SEQ ID No. 15, or to the full length of a sequence of nucleotides encoding the amino acid sequence set forth in SEQ ID No. 16.

55. The method of claim 51, wherein the cells further comprise nucleic acid encoding a $\beta_2$ subunit that comprises a sequence of amino acids encoded by a sequence of nucleotides that hybridizes along its full length under conditions of high stringency to the entire coding sequence of nucleotides set forth in SEQ ID No. 13, or to the full length of a sequence of nucleotides encoding the amino acid sequence set forth in SEQ ID No. 14.

56. The method of claim 51, wherein the cells further comprise nucleic acid encoding a $\beta_4$ subunit that comprises a sequence of amino acids encoded by a sequence of nucleotides that hybridizes along its full length under conditions of high stringency to the entire coding sequence of nucleotides set forth in SEQ ID No. 17, or to the full length of a sequence of nucleotides encoding the amino acid sequence set forth, in SEQ ID No. 18.

57. The method of claim 51, wherein the recombinant cells are mammalian, cells, yeast cells or amphibian oocytes.

58. The method of claim 51, wherein:
the alteration in ion flux or the electrophysiological response of the cells is detected by comparing the measurements with measurements using control cells; and
control cells are cells that do not express nNAChRs.

59. The method of claim 51, wherein:
the alteration in ion flux or the electrophysiological response of the cells is detected by comparing the measurements with measurements using control compounds; and
control compounds are known agonists or antagonists of human nNAChRs.

60. The method of claim 51, wherein prior to or simultaneously with contacting the cells with a test compound the cells are contacted with a known nNAChR agonist.

61. The method of claim 51, wherein prior to or simultaneously with contacting the cells with a test compound the cells are contacted with a known nNAChR antagonist.

62. The method of claim 51, in which an agonist is detected, wherein:
the recombinant cells further comprise a DNA encoding a reporter gene operatively linked to DNA encoding a transcriptional control element wherein the activity of the transcriptional control element is regulated by the human neuronal nicotinic acetylcholine receptor;
the reporter gene encodes a detectable gene product, wherein the detectable product is selected from the group consisting of mRNA and a polypeptide; and
the interaction of the test compound with the nNAChRs is measured by detecting the gene product encoded by the reporter gene.

63. The method of claim 51, wherein the nucleic acid is DNA.

64. The method of claim 51, wherein the nucleic acid is mRNA.

65. The method according to claim 51, wherein the $\alpha_3$ subunit comprises a sequence of amino acids encoded by the $\alpha_3$ encoding nucleic acid that is isolated from a plasmid having all of the identifying characteristics of HnAChR $\alpha$3 deposited under ATCC Accession No. 68278.

66. A method for identifying compounds that are antagonists or agonists of human neuronal nicotinic acetylcholine receptors (nNAChRs), said method comprising:
a) contacting recombinant cells with a test compound, wherein:
the recombinant cells comprise heterologous nucleic acid encoding at least one human nNAChR subunit;
express an nNAChR comprising at least one human subunit encoded by the heterologous nucleic acid; and b) measuring ion flux, the electrophysiological response of the cells, or interaction of the test compound with the nNAChRs, whereby compounds that are agonists or antagonists of the nNAChR are identified, wherein:

the $\alpha_4$ subunit is encoded by nucleic acid that hybridizes along its full length under conditions of high stringency to nucleic acid that encodes the sequence of amino acids set forth in SEQ ID No:6 or the $\alpha_4$ subunit comprises the sequence of amino acids encoded by $\alpha$4 subunit encoding nucleic acid in clone HnAChR $\alpha$4.2, deposited under ATCC Accession No. 69239; or the $\alpha_4$ subunit comprises the sequence of amino acids encoded by $\alpha$4 subunit encoding nucleic acid in clone HnAChR $\alpha$4.1, deposited under ATCC Accession No. 69152;

the $\alpha_4$ subunit is encoded by nucleic acid that hybridizes under conditions of high stringency to nucleotides 184–2067 of SEQ ID No. 5; or the $\alpha_4$ subunit is encoded by nucleic acid that hybridizes under conditions of high stringency to the entire $\alpha$4 encoding insert of clone HnAChR $\alpha$4.2deposited under ATCC Accession No. 69239.

67. The method of claim 66, wherein said $\alpha_4$ subunit comprises the sequence of amino acids set forth in SEQ ID NO:6.

68. The method of claim 66, wherein the cells further comprise nucleic acid encoding $\beta_3$ subunit that comprises a sequence of amino acids encoded by a sequence of nucleotides that hybridizes along its full length under conditions of high stringency to the entire coding sequence of nucleotides set forth in SEQ ID No. 15, or to the full length of a sequence of nucleotides encoding the amino acid sequence set forth in SEQ ID No. 16.

69. The method of claim 66, wherein the cells further comprise nucleic acid encoding a $\beta_2$ subunit that comprises a sequence of amino acids encoded by a sequence of nucleotides that hybridizes along its full length under conditions of high stringency to the entire coding sequence of nucleotides set forth in SEQ ID No. 13, or to the full length of a sequence of nucleotides encoding the amino acid sequence set forth in SEQ ID No. 14.

70. The method of claim 66, wherein the cells further comprise nucleic acid encoding a $\beta_4$ subunit that comprises a sequence of amino acids encoded by a sequence of nucleotides that hybridizes along its full length under conditions of high stringency to the entire coding sequence of nucleotides set forth in SEQ ID No. 17, or to the full length of a sequence of nucleotides encoding the amino acid sequence set forth in SEQ ID No. 18.

71. The method of claim 66, wherein the recombinant cells are mammalian cells, yeast cells or amphibian oöcytes.

72. The method of claim 66, wherein:
the alteration in ion flux or the electrophysiological response of the cells is detected by comparing the measurements with measurements using control cells; and
control cells are cells that do not express nNAChRs.

73. The method of claim 66, wherein:
the alteration in ion flux or the electrophysiological response of the cells is detected by comparing the measurements with measurements using control compounds; and
control compounds are known agonists or antagonists of human nNAChRs.

74. The method of claim 66, wherein prior to or simultaneously with contacting the cells with a test compound the cells are contacted with a known nNAChR agonist.

75. The method of claim 66, wherein prior to or simultaneously with contacting the cells with a test compound the cells are contacted with a known nNAChR agonist.

76. The method of claim 66, in which an agonist is detected, wherein:
the recombinant cells further comprise a DNA encoding a reporter gene operatively linked to DNA encoding a transcriptional control element wherein the activity of the transcriptional control element is regulated by the human neuronal nicotinic acetylcholine receptor;
the reporter gene encodes a detectable gene product, wherein the detectable product is selected from the group consisting of mRNA and a polypeptide; and
the interaction of the test compound with the nNAChRs is measured by detecting the gene product encoded by the reporter gene.

77. The method of claim 66, wherein the nucleic acid is DNA.

78. The method of claim 66, wherein the nucleic acid is mRNA.

79. The method according to claim 66, wherein the $\alpha_4$ subunit is encoded by a nucleic acid that hybridizes along its full length under conditions of high stringency to a nucleic acid that encodes the sequence of amino acids set forth in SEQ ID No:6.

80. The method according to claim 66, wherein the $\alpha_4$ subunit comprises the sequence of amino acids encoded by the $\alpha$4 subunit encoding nucleic acid in clone HnAChR $\alpha$4.2, deposited under ATCC Accession No. 69239.

81. The method according to claim 66, wherein the $\alpha_4$ subunit comprises the sequence of amino acids encoded by the $\alpha$4 subunit encoding nucleic acid in clone HnAChR $\alpha$4.1, deposited under ATCC Accession No. 69152.

82. The method according to claim 66, wherein the $\alpha_4$ subunit is encoded by a nucleic acid that hybridizes under conditions of high stringency to nuleotides 184–2067 of SEQ ID No. 5.

83. The method according to claim 66, wherein the $\alpha_4$ subunit is encoded by a nucleic acid that hybridizes under conditions of high stringency to the entire $\alpha$4 encoding insert of clone HnAChR $\alpha$4.2 deposited under ATCC Accession No. 69239.

84. The method according to claim 6, wherein the $\alpha_4$ subunit is encoded by a nucleic acid defined by nucleotides 184–2067 of SEQ ID No. 5.

85. A method for identifying compounds that are antagonists or agonists of human neuronal nicotinic acetylcholine receptors (nNAChRs), said method comprising:

a) contacting recombinant cells with a test compound, wherein:
the recombinant cells comprise heterologous nucleic acid encoding at least one human nNAChR subunit;
express an nNAChR comprising at least one human subunit encoded by the heterologous nucleic acid; and
the at least one human nNAChR subunit encoded by the heterologous nucleic acid is an $\alpha_6$ subunit; and b) measuring ion flux, the electrophysiological response of the cells or interaction of the test compound with the nNAChRs, whereby compounds that are agonists or antagonists of the nNAChR are identified, wherein:
the $\alpha_6$ subunit comprises a sequence of amino acids encoded by nucleic acid that hybridizes along its full length under conditions of high stringency to the coding sequence in the sequence of nucleotides set forth in SEQ ID No. 9,
or the $\alpha_6$ subunit comprises the sequence of amino acids sequence set forth in SEQ ID No. 10.

86. The method of claim 85, wherein said $\alpha_6$ subunit comprises the sequence of amino acids set forth in SEQ ID NO:10.

87. The method of claim 85, wherein the cells further comprise nucleic acid encoding $\beta_3$ subunit that comprises a sequence of amino acids encoded by a sequence of nucleotides that hybridizes along its full length under conditions of high stringency to the entire coding sequence of nucleotides set forth in SEQ ID No. 15, or to the full length of a sequence of nucleotides encoding the amino acid sequence set forth in SEQ ID No. 16.

88. The method of claim 85, wherein the cells further comprise nucleic acid encoding a $\beta_2$ subunit that comprises a sequence of amino acids encoded by a sequence of nucleotides that hybridizes along its full length under conditions of high stringency to the entire coding sequence of nucleotides set forth in SEQ ID No. 13, or to the full length of a sequence of nucleotides encoding the amino acid sequence set forth in SEQ ID No. 14.

89. The method of claim 85, wherein the cells further comprise nucleic acid encoding a $\beta_4$ subunit that comprises a sequence of amino acids encoded by a sequence of nucleotides that hybidizes along it full length under conditions of high stringency to the entire coding sequence of nucleotides set forth in SEQ ID No. 17, or to the full length of a sequence of nucleotides encoding the amino acid sequence set forth in SEQ ID No. 18.

90. The method of claim 85, wherein the recombinant cells are mammalian cells, yeast cells or amphibian oöcytes.

91. The method of claim 85, wherein:
the alteration in ion flux or the electrophysiological response of the cells is detected by comparing the measurements with measurements using control cells; and
control cells are cells that do not express nNAChRs.

92. The method of claim 85, wherein:
the alteration in ion flux or the electrophysiological response of the cells is detected by comparing the measurements with measurements using control compounds; and
control compounds are known agonists or antagonists of human nNAChRs.

93. The method of claim 85, wherein prior to or simultaneously with contacting the cells with a test compound the cells are contacted with a known nNAChR agonist.

94. The method of claim 85, wherein prior to or simultaneously with contacting the cells with a test compound the cells are contacted with a known nNAChR agonist.

95. The method of claim 85, which an agonist is detected, wherein:
the recombinant cells further comprise a DNA encoding a reporter gene operatively linked to DNA encoding a transcriptional control element wherein the activity of the transcriptional control element is regulated by the human neuronal nicotinic acetylcholine receptor;
the reporter gene encodes a detectable gene product, wherein the detectable product is selected from the group consisting of mRNA and a polypeptide; and
the interaction of the test compound with the nNAChRs is measured by detecting the gene product encoded by the reporter gene.

96. The method of claim 85, wherein the nucleic acid is DNA.

97. The method of claim 85, wherein the nucleic acid is mRNA.

98. The method according to claim 85, wherein the $\alpha_6$ subunit comprises a sequence of amino acids encoded by a nucleic acid that hybridizes along its full length under conditions of high stringency to the coding sequence in the sequence of nucleotides set forth in SEQ ID No. 9.

99. The method according to claim 85, wherein the $\alpha_6$ subunit comprises a sequence of amino acids as set forth SEQ ID No. 10.

100. The method according to claim 85, wherein the $\alpha_6$ subunit comprises a sequence of amino acids encoded by a nucleic acid comprising the coding sequence in the sequence of nucleotides set forth in SEQ ID No. 9.

101. A method for identifying compounds that are antagonists or agonists of human neuronal nicotinic acetylcholine receptors (nHAChRs), said method comprising:
a) contacting recombinant cells with a test compound, wherein:
the recombinant cells comprise heterologous nucleic acid encoding at least one human nNAChR subunit;
express an nNAChR comprising at least one human subunit encoded by the heterologous nucleic acid; and
the at least one human nNAChR subunit encoded by the heterologous nucleic acid is an $\alpha_7$ subunit and
b) measuring ion flux, the electrophysiological response of the cells, or interaction of the test compound with the nNAChRs, whereby compounds that are agonists or antagonists of the nNAChR are identified, wherein:
the $\alpha_7$ subunit comprises a sequence of amino acids encoded by nucleic acid that hybridizes along its full length under conditions of high stringency to the coding sequence in the sequence of nucleotides set forth in SEQ ID No. 11,
or the $\alpha_7$ subunit comprises the sequence of amino acid sequence set forth in SEQ ID No. 12.

102. A method according to claim 101 wherein said $\alpha_7$ subunit comprises the sequence of amino acids set forth in SEQ ID NO:12.

103. The method of claim 101, wherein the cells further comprise nucleic acid encoding $\beta_3$ subunit that comprises a sequence of amino acids encoded by a sequence of nucleotides that hybridizes along its full length under conditions of high stringency to the entire coding sequence of nucleotides set forth in SEQ ID No. 15, or to the full length of a sequence of nucleotides encoding the amino acid sequence set forth in SEQ ID No. 16.

104. The method of claim 101, wherein the cells further comprise nucleic acid encoding a $\beta_2$ subunit that comprises a sequence of amino acids encoded by a sequence of nucleotides that hybridizes along its full length under conditions of high stringency to the entire coding sequence of nucleotides set forth in SEQ ID No. 13, or to the full length of a sequence of nucleotides encoding the amino acid sequence set forth in SEQ ID No. 14.

105. The method of claim 101, wherein the cells further comprise nucleic acid encoding a $\beta_4$ subunit that comprises a sequence of amino acids encoded by a sequence of nucleotides that hybridizes along its full length under conditions of high stringency to the entire coding sequence of nucleotides set forth in SEQ ID No. 17, or to the full length of a sequence of nucleotides encoding the amino acid sequence set forth in SEQ ID No. 18.

106. The method of claim 101, wherein the recombinant cells are mammalian cells, yeast cells or amphibian oöcytes.

107. The method of claim 101, wherein:
the alteration in ion flux or the electrophysiological response of the cells is detected by comparing the measurements with measurements using control cells; and
control cells are cells that do not express nNAChRs.

108. The method of claim 102, wherein:
the alteration in ion flux or the electrophysiological response of the cells is detected by comparing the measurements with measurements using control compounds; and
control compounds are known agonists or antagonists of human nNAChRs.

109. The method of claim 101, wherein prior to or simultaneously with contacting the cells with a test compound the cells are contacted with a known nNAChR agonist.

110. The method of claim 101, wherein prior to or simultaneously with contacting the cells with a test compound the cells are contacted with a known nNAChR antagonist.

111. The method of claim 101, which an agonist is detected, wherein:
the recombinant cells further comprise a DNA encoding a reporter gene operatively linked to DNA encoding a transcriptional control element wherein the activity of the transcriptional control element is regulated by the human neuronal nicotinic acetylcholine receptor;
the reporter gene encodes a detectable gene product, wherein the detectable product is selected from the group consisting of mRNA and a polypeptide; and
the interaction of the test compound with the nNAChRs is measured by detecting the gene product encoded by the reporter gene.

112. The method of claim 101, wherein the nucleic acid is DNA.

113. The method of claim 101, wherein the nucleic acid is mRNA.

114. The method according to claim 101, wherein the $\alpha_7$ subunit comprises a sequence of amino acids encoded by a nucleic acid that hybridizes along its full length under conditions of high stringency to the coding sequence in the sequence of nucleotides set forth in SEQ ID No. 11.

115. The method according to claim 101, wherein the $\alpha_7$ subunit comprises a sequence of amino acids as set forth in SEQ ID No. 12.

116. The method according to claim 101, wherein the $\alpha_7$ subunit comprises a sequence of amino acids encoded by a nucleic acid comprising a sequence of nucleotides as set forth in SEQ ID No. 11.

117. The method according to claim 101, wherein the $\alpha_7$ subunit comprises a sequence of amino acids encoded by a nucleic acid comprising the coding sequence in the sequence of nucleotides set forth in SEQ ID No. 11.

118. A method for identifying compound that are antagonists or agonists of human neuronal nicotinic acetylcholine receptors (nNAChRs), said method comprising:
a) contacting recombinant cells with a test compound, wherein:
the recombinant cells comprise heterologous nucleic acid encoding at least one human nNAChR subunit;
express an nNAChR comprising at least one human subunit encoded by the heterologous nucleic acid; and
the at least one human nNAChR subunit encoded by the heterologous nucleic acid is an $\alpha_5$ subunit; and
b) measuring ion flux, the electrophysiological response of the cells, or binding of the test compound to the nNAChR, whereby compounds that are agonists or antagonists of the nNAChR are identified, wherein:
the $\alpha_5$ subunit comprises a sequence of amino acids encoded by nucleic acid that hybridizes along its full length under conditions of high stringency to the coding sequence in the sequence of nucleotides set forth in SEQ ID No. 7,
or the $\alpha_5$ subunit comprises the sequence of amino acid sequence set forth in SEQ ID No. 8.

119. The method of claim 118, wherein the cells further comprise nucleic acid encoding a $\beta_3$ subunit that comprises a sequence of amino acids encoded by a sequence of nucleotides that hybridizes along its full length under conditions of high stringency to the entire coding sequence of nucleotides set forth in SEQ ID No. 15, or to the full length of a sequence of nucleotides encoding the amino acid sequence set forth in SEQ ID No. 16.

120. The method of claim 118, wherein the cells further comprise nucleic acid encoding a $\beta_2$ subunit that comprises a sequence of amino acids encoded by a sequence of nucleotides that hybridizes along its full length under conditions of high stringency to the entire coding sequence of nucleotides set forth in SEQ ID No. 13, or to the full length of a sequence of nucleotides encoding the amino acid sequence set forth in SEQ ID No. 14.

121. The method of claim 118, wherein the cells further comprise nucleic acid encoding a $\beta_4$ subunit that comprises a sequence of amino acids encoded by a sequence of nucleotides that hybridizes along its full length under conditions of high stringency to the entire coding sequence of nucleotides set forth in SEQ ID No. 17, or to the full length of a sequence of nucleotides encoding the amino acid sequence set forth in SEQ ID No. 18.

122. The method of claim 118, wherein the recombinant cells are mammalian cells, yeast cells or amphibian oocytes.

123. The method of claim 118, wherein:
the alteration in ion flux or the electrophysiological response of the cells is detected by comparing the measurements with measurements using control cells; and
control cells are cells that do not express nNAChRs.

124. The method of claim 118, wherein:
the alteration in ion flux or the electrophysiological response of the cells is detected by comparing the measurements with measurements using control compounds; and
control compounds are known agonists or antagonists of human nNAChRs.

125. The method of claim 118, wherein prior to or simultaneously with contacting the cells with a test compound the cells are contacted with a known nNAChR agonist.

126. The method of claim 118, wherein prior to or simultaneously with contacting the cells with a test compound the cells are contacted with a known nNAChR antagonist.

127. The method of claim 118, which an agonist is detected, wherein:
the recombinant cells further comprise a DNA encoding a reporter gene operatively linked to DNA encoding a transcriptional control element wherein the activity of the transcriptional control element is regulated by the human neuronal nicotinic acetylcholine receptor;
the reporter gene encodes a detectable gene product, wherein the detectable product is selected from the group consisting of mRNA and a polypeptide; and
the interaction of the test compound with the nNAChRs is measured by detecting the gene product encoded by the reporter gene.

128. The method of claim 118, wherein the nucleic acid is DNA.

129. The method of claim 118, wherein the nucleic acid is mRNA.

130. The method according to claim 118, wherein the $\alpha_5$ subunit comprises a sequence of amino acids encoded by a nucleic acid that hybridizes along its full length under conditions of high stringency to the coding sequence in the sequence of nucleotides set forth in SEQ ID No. 7.

131. The method according to claim 118, wherein the $\alpha_5$ subunit comprises a sequence of amino acids as set forth in SEQ ID No. 8.

132. The method according to claim 118, wherein the $\alpha_5$ subunit comprises a sequence of amino acids encoded by a nucleic acid comprising a sequence of nucleotides as set forth in SEQ ID No. 7.

133. The method according to claim 118, wherein the $\alpha_5$ subunit comprises a sequence of amino acids encoded by a nucleic acid comprising the coding sequence in the sequence of nucleotides set forth in SEQ ID No. 7.

134. The method according to claim 118, wherein the $\alpha_5$ subunit is encoded by a nucleic acid comprising the sequence of nucleotides set forth in SEQ ID No. 7.

135. A method for identifying compounds that are antagonists or agonists of human neuronal nicotinic acetylcholine receptors (nNAChRs), said method comprising:
  a) contacting recombinant cells with a test compound, wherein:
    the recombinant cells comprise heterologous nucleic acid encoding at least one human nNAChR subunit;
    the recombinant cells express an nNAChR comprising at least one human subunit encoded by the heterologous nucleic acid;
    the heterologous nucleic acid encodes a $\beta_2$ subunit of a human nNAChR; and
    the expressed nNAChR comprises at least one nNAChR $\alpha$ subunit and the $\beta_2$ subunit; and
  (b) measuring ion flux, the electrophysiological response of the cells, or interaction of the test compound to the nNAChR, whereby compounds that are agonists or antagonists of the nNAChR are identified, wherein the $\beta_2$ subunit comprises the sequence of amino acids set forth in SEQ ID No. 14.

136. The method of claim 135, wherein the cells further comprise a heterologous nucleic acid encoding an additional subunit of nNAChR, wherein the additional nNAChR subunit is an $\alpha_2$ and comprises a sequence of amino acids having more than 95% identity with the amino acid sequence set forth in SEQ ID No. 2; or
  is encoded by a sequence of nucleotides that hybridizes under conditions of high stringency with the complement of nucleotides 166–1755 set forth in SEQ ID No 1 or shares at least about 90% identity to nucleotides 166–1755 in SEQ ID No: 1; or
  the $\alpha_2$ subunit comprises the sequence of amino acids set forth in SEQ. ID No: 2; or
  the $\alpha_2$ subunit is encoded by nucleotides 166–1755 of SEQ ID No: 1.

137. The method according to claim 136, wherein the $\alpha_2$ subunit comprises a sequence of amino acids having more than 95% identity with the amino acid sequence set forth in SEQ ID No.2.

138. The method according to claim 136, wherein the $\alpha_2$ subunit is encoded by a sequence of nucleotides that hybridizes under conditions of high stringency with the complement of nucleotides 166–1755 set forth in SEQ ID No. 1 or shares at least about 90% identity to nucleotides 166–1755 in SEQ ID No 1.

139. The method according to claim 136, wherein the $\alpha_2$ subunit is encoded by the nucleotides of 166–1755 of SEQ ID No. 1.

140. The method of claim 135, wherein the recombinant cells are mammalian cells, yeast cells or amphibian oocytes.

141. A method for identifying compounds that are antagonists or agonists of human neuronal nicotinic acetylcholine receptors (nNAChRs), said method comprising:
  a) contacting recombinant cells with a test compound, wherein:
    the recombinant cells comprise heterologous nucleic acid encoding at least one human nNAChR subunit; and
    the at least one human nNAChR subunit encoded by the heterologous nucleic acid is an $\alpha_3$ subunit, wherein:
    the $\alpha_3$ subunit comprises a sequence of amino acids encoded by the $\alpha_3$-encoding nucleic acid that is isolated from a plasmid having all of the identifying characteristics of HnAChR $\alpha_3$ deposited under ATCC Accession No. 68278; or comprises the sequence of amino acids set forth in SEQ ID No. 4; and
    the recombinant cells further comprise DNA encoding a reporter gene operatively linked to DNA encoding a transcriptional control element, wherein the activity of the transcriptional control element is regulated by the human neuronal nicotinic acetylcholine receptor;
    the reporter gene encodes a detectable gene product, wherein the detectable product is selected from the group consisting of mRNA and a polypeptide; and
  b) measuring transcription of the reporter gene by detecting the gene product, whereby compounds that are agonists or antagonists of the nNAChR are identified.

142. The method of claim 141, wherein the recombinant cells are mammalian cells, yeast cells or amphibian oocytes.

143. A method for identifying compounds that are antagonists or agonists of human neuronal nicotinic acetylcholine receptors (nNAChRs), said method comprising:
  a) contacting recombinant cells with a test compound, wherein:
    the recombinant cells comprise heterologous nucleic acid encoding at least one human nNAChR subunit;
    express an nNAChR comprising at least one human subunit encoded by the heterologous nucleic acid; and
    the at least one human nNAChR subunit encoded by the heterologous nucleic acids is an $\alpha_4$ subunit, wherein:
    the $\alpha_4$ subunit is encoded by nucleic acid that hybridizes along its full length under conditions of high stringency to a nucleic acid that encodes the sequence of amino acids set forth in SEQ ID No: 6;
    the $\alpha_4$ subunit is encoded by nucleic acid that hybridizes under conditions of high stringency to the entire $\alpha_4$ encoding insert of clone HnAChR$\alpha$4.2, deposited under ATCC Accession No. 69239;
    the $\alpha_4$ subunit comprises the sequence of amino acids encoded by $\alpha_4$ subunit encoding nucleic acid in cline HnAChR $\alpha$4.1, deposited under ATCC Accession No. 69152;
    the $\alpha_4$ subunit is encoded by the nucleic acid that hybridizes along it full length under conditions of high stringency to the entire length of nucleotides 184–2067 of SEQ ID No. 5; or
    the $\alpha_4$ subunit is encoded by nucleic acid that hybridizes under conditions of high stringency to the entire $\alpha_4$ encoding insert of clone HnAChR$\alpha$4.2, deposited under ATCC Accession No. 69239; and the recombinant cells further comprise DNA encoding a reporter gene operatively linked to DNA encoding a transcriptional control element, wherein the activity of the transcriptional control element is regulated by the human neuronal nicotinic acetylcholine receptor; and the reporter gene encodes a detectable gene product, wherein the detectable product is selected from the group consisting of mRNA and a polypeptide; and b) measuring transcription of the reporter gene by detecting the gene product, whereby compounds that are agonists or antagonists of the nNAChR are identified.

144. The method according to claim 143, wherein the $\alpha_4$ subunit is encoded by a nucleic acid that hybridizes along its full length under conditions of high stringency to a nucleic acid that encodes the sequence of amino acids set forth in SEQ ID No.6.

145. The method according to claim 143, wherein the $\alpha_4$ subunit comprises the sequence of amino acids encoded by the $\alpha_4$ subunit encoding nucleic acid in clone HnAChR $\alpha$4.2, deposited under ATCC Accession No. 69239.

146. The method according to claim 143, wherein the at subunit comprises the sequence of amino acids encoded by the $\alpha_4$ subunit encoding nucleic acid in clone HnAChR $\alpha$4.1, deposited under ATCC Accession No. 69152.

147. The method according to claim 143, wherein the $\alpha_4$ subunit is encoded by a nucleic acid that hybridizes under conditions of high stringency to nucleotides 184–2067 of SEQ ID No. 5.

148. The method according to claim 143, wherein the $\alpha_4$ subunit is encoded by a nucleic acid that hybridizes under conditions of high stringency to the entire $\alpha_4$ encoding insert of clone HnAChR $\alpha$4.2 deposited under ATCC Accession No. 69239.

149. The method according to claim 143, wherein the $\alpha_4$ subunit is encoded by a nucleic acid defined by nucleotides 184–2067 of SEQ ID No. 5.

150. A method for identifying compounds that are antagonists or agonists of human neuronal nicotinic acetylcholine receptors (nNAChRs), said method comprising:

a) contacting recombinant cells with a test compound, wherein:

the recombinant cells comprise heterologous nucleic acid encoding at least one human nNAChR subunit;

express an nNAChR comprising at least one human subunit encoded by the heterologous nucleic acid; and the at least one human nNAChR subunit encoded by the heterologous nucleic acid is an $\alpha_6$ subunit, wherein:

the $\alpha_6$ subunit comprises a sequence of amino acids encoded by nucleic acid that hybridizes along its full length under conditions of high stringency to the coding sequence in the sequence of nucleotides set forth in SEQ ID No. 9, or the $\alpha_6$ subunit comprises the sequence of amino acid sequence set forth in SEQ ID No. 10; and the recombinant cells further comprise DNA encoding a reporter gene operatively linked to DNA encoding a transcriptional control element, wherein the activity of the transcriptional control element is regulated by the human neuronal nicotinic acetylcholine receptor; and the reporter gene encodes a detectable gene product, wherein the detectable product is selected from the group consisting of mRNA and a polypeptide; and b) measuring transcription of the reporter gene by detecting the gene product, whereby compounds that are agonists or antagonists of the nNAChR are identified.

151. The method according to claim 150, wherein the $\alpha_6$ subunit comprises a sequence of amino acids encoded by a nucleic acid that hybirdizes along it full length under conditions of high stringencey to the coding sequence in the sequence of nucleotides set forth in SEQ ID No. 9.

152. The method according to claim 150, wherein the $\alpha_6$ subunit comprises a sequence of amino acids as set forth in SEQ ID No. 10.

153. The method according to claim 150, wherein the $\alpha_6$ subunit comprises a sequence of amino acids encoded by a nucleic acid comprises the coding sequence in the sequence of nucleotides set forth in SEQ ID No. 9.

154. A method for identifying compounds that are antagonists or agonists of human neuronal nicotinic acetylcholine receptors (nNAChRs), said method comprising:

a) contacting recombinant cells with a test compound, wherein:

the recombinant cells comprise heterologous nucleic acid encoding at least one human nNAChR subunit;

express an nNAChR comprising at least one human subunit encoded by the heterologous nucleic acid; and the at least one human nNAChR subunit encoded by the heterologous nucleic acid is an $\alpha_7$ subunit, wherein:

the $\alpha_7$ subunit comprises a sequence of amino acids encoded by nucleic acid that hybridizes along its full length under conditions of high stringency to the coding sequence in the sequence of nucleotides set forth in SEQ ID No. 11, or the $\alpha_7$ subunit comprises the sequence of amino acid sequence set forth in SEQ ID No. 12; and the recombinant cells further comprise DNA encoding a reporter gene operatively linked to DNA encoding a transcriptional control element, wherein the activity of the transcriptional control element is regulated by the human neuronal nicotinic acetylcholine receptor; and the reporter gene encodes a detectable gene product, wherein the detectable product is selected from the group consisting of mRNA and a polypeptide; and b) measuring transcription of the reporter gene by detecting the gene product, whereby compounds that are agonists or antagonists of the nNAChR are identified.

155. The method according to claim 154, wherein the $\alpha_7$ subunit comprises a sequence of amino acids encoded by a nucleic acid that hybridizes along its full length under conditions of high stringency to the coding sequence in the sequence of nucleotides set forth in SEQ ID No. 11.

156. The method according to claim 154, wherein the $\alpha_7$ subunit comprises a sequence of amino acids as set forth in SEQ ID No. 12.

157. The method according to claim 154, wherein the $\alpha_7$ subunit comprises a sequence of amino acids encoded by a nucleic acid comprising a sequence of nucleotides as set forth in SEQ ID No. 11.

158. The method according to claim 154, wherein the $\alpha_7$ subunit comprises a sequence of amino acids encoded by a nucleic acid comprising the coding sequence in the sequence of nucleotides set forth in SEQ ID No. 11.

159. A method for identifying compounds that are antagonists or agonists of human neuronal nicotinic acetylcholine receptors (nNAChRs), said method comprising:

a) contacting recombinant cells with a test compound, wherein:

the recombinant cells comprise heterologous nucleic acid encoding at least one human nNAChR subunit;

express an nNAChR comprising at least one human subunit encoded by the heterologous nucleic acid; and the at least one human nNAChR subunit encoded by the heterologous nucleic acid is an $\alpha_5$ subunit, wherein:

the $\alpha_5$ subunit comprises a sequence of amino acids encoded by a nucleic acid that hybridizes along its full length under conditions of high stringency to the coding sequence in the sequence of nucleotides set forth in SEQ ID No. 7, or the $\alpha_5$ subunit comprises the sequence of amino acid sequence set forth in SEQ ID No. 8; and the recombinant cells further comprise DNA encoding a reporter gene operatively linked to DNA encoding a transcriptional control element, wherein the activity of the transcriptional control element is regulated by the human neuronal nicotinic acetylcholine receptor; and the reporter gene encodes a detectable gene product, wherein the detectable product is selected from the group consisting of mRNA and a polypeptide; and b) measuring transcription of the reporter gene by detecting the gene product, whereby compounds that are agonists or antagonists of the nNAChR are identified.

160. The method according to claim 159, wherein the $\alpha_5$ subunit comprises a sequence of amino acids encoded by a nucleic acid that hybridizes along its full length under conditions of high stringency to the coding sequence in the sequence of nucleotides set forth in SEQ ID No. 7.

161. The method according to claim 159, wherein the $\alpha_5$ subunit comprises a sequence of amino acids as set forth in SEQ ID No. 8.

162. The method according to claim 159, wherein the $\alpha_5$ subunit comprises a sequence of amino acids encoded by a nucleic acid comprising a sequence of nucleotides as set forth in SEQ ID No. 7.

163. The method according to claim 159, wherein the $\alpha_5$ subunit comprises a sequence of amino acids encoded by a nucleic acid comprising the coding sequence in the sequence of nucleotides set forth in SEQ ID No. 7.

164. The method according to claim 159, wherein the $\alpha_5$ subunit is encoded by a nucleic acid comprising the sequence of nucleotides set forth in SEQ ID No. 7.

165. A method for identifying compounds that are antagonists or agonists of human neuronal nicotinic acetylcholine receptors (nNAChRs), said method comprising:

a) contacting recombinant cells with a test compound, wherein:

the recombinant cells comprise heterologous nucleic acid encoding at least one human nNAChR subunit;

express an nNAChR comprising at least one human subunit encoded by the heterologous nucleic acid; and the at least one human nNAChR subunit encoded by the heterologous nucleic acid is an $\alpha_2$ subunit, wherein:

the $\alpha_2$ subunit comprises a sequence of amino acids having more than 95% identity with amino acid sequence set forth in SEQ ID No. 2; or the $\alpha_2$ subunit is encoded by a sequence of nucleotides that hybridizes under conditions of high stringency with the complement of nucleotides 166–1755 set forth in SEQ ID No. 1 or shares at least about 90% identity to nucleotides 166–1755 in SEQ ID No:1; or $\alpha_2$ subunit comprises the sequence of amino acids set forth in SEQ ID NO:2; or the $\alpha_2$ subunit is encoded by the nucleotides 166–1755 of SEQ ID No. 1; and the recombinant cells further comprise DNA encoding a reporter gene operatively linked to DNA encoding a transcriptional control element, wherein the activity of the transcriptional control element is regulated by the human neuronal nicotinic acetylcholine receptor; and the reporter gene encodes a detectable gene product, wherein the detectable product is selected from the group consisting of mRNA and a polypeptide; and b) measuring transcription of the reporter gene by detecting the gene product, whereby compounds that are agonists or antagonists of the nNAChR are identified.

166. The method according to claim 165, wherein the $\alpha_2$ subunit comprises a sequence of amino acids having more than 95% idenity with the amino acid sequence set forth in SEQ ID No.2.

167. The method according to claim 165, wherein the $\alpha_2$ subunit is encoded by a sequence of nucleotides that hybridizes under conditions of high stringency with the complement of nucleotides 166–1755 set forth in SEQ ID No. 1 or shares at least about 90% identity to nucleotides 166–1755 in SEQ ID No. 1.

168. The method according to claim 165, wherein the $\alpha_2$ subunit is encoded by the nucleotides 166–1755 of SEQ ID No. 1.

* * * * *